United States Patent [19]

Unger et al.

[11] Patent Number: 5,733,572
[45] Date of Patent: *Mar. 31, 1998

[54] GAS AND GASEOUS PRECURSOR FILLED MICROSPHERES AS TOPICAL AND SUBCUTANEOUS DELIVERY VEHICLES

[75] Inventors: Evan C. Unger; Terry O. Matsunaga; David Yellowhair, all of Tucson, Ariz.

[73] Assignee: ImaRx Pharmaceutical Corp., Tucson, Ariz.

[*] Notice: The term of this patent shall not extend beyond the expiration date of Pat. No. 5,149,319.

[21] Appl. No.: 346,426

[22] Filed: Nov. 29, 1994

Related U.S. Application Data

[63] Continuation-in-part of Ser. No. 307,305, Sep. 16, 1994, Ser. No. 159,687, Nov. 30, 1993, Pat. No. 5,585,112, Ser. No. 160,232, Nov. 30, 1993, Pat. No. 5,542,935, and Ser. No. 159,674, Nov. 30, 1993, abandoned, said Ser. No. 159,687, Ser. No. 160,232, and Ser. No. 159,674, each is a continuation-in-part of Ser. No. 76,239, Jun. 11, 1993, Pat. No. 5,469,854, and Ser. No. 76,250, Jun. 11, 1993, Pat. No. 5,580,575, said Ser. No. 76,239, and Ser. No. 76,250, each is a continuation-in-part of Ser. No. 717,084, Jun. 18, 1991, Pat. No. 5,228,446, and Ser. No. 716,899, Jun. 18, 1991, abandoned, said Ser. No. 717,084, and Ser. No. 716,899, each is a continuation-in-part of Ser. No. 569,828, Aug. 20, 1990, Pat. No. 5,088,499, which is a continuation-in-part of Ser. No. 455,707, Dec. 22, 1989, abandoned.

[51] Int. Cl.[6] ................................. A61K 9/127
[52] U.S. Cl. ............. 424/450; 424/121; 424/9.321; 424/9.4; 424/489; 436/829
[58] Field of Search ................. 424/450, 1.21, 424/9.321, 9.4, 489; 436/829

[56] References Cited

U.S. PATENT DOCUMENTS

| | | | |
|---|---|---|---|
| 3,015,128 | 1/1962 | Sommerville et al. | 18/2.6 |
| 3,293,114 | 12/1966 | Kenaga et al. | 162/168 |
| 3,479,811 | 11/1969 | Walters | 57/153 |
| 3,488,714 | 1/1970 | Walters et al. | 161/161 |
| 3,532,500 | 10/1970 | Priest et al. | 96/91 |
| 3,594,326 | 7/1971 | Himmel et al. | 252/316 |
| 3,615,972 | 10/1971 | Morehouse et al. | 156/79 |
| 3,732,172 | 5/1973 | Herbig et al. | 252/316 |

(List continued on next page.)

FOREIGN PATENT DOCUMENTS

| | | |
|---|---|---|
| B-30351/89 | 3/1993 | Australia. |
| 0 107 559 | 5/1984 | European Pat. Off.. |
| 0 077 752 B1 | 3/1986 | European Pat. Off.. |
| 0 243 947 | 4/1987 | European Pat. Off.. |
| 0 231 091 | 8/1987 | European Pat. Off.. |
| 0 272 091 | 6/1988 | European Pat. Off.. |
| 0 320 433 A2 | 12/1988 | European Pat. Off.. |
| 0 324 938 | 7/1989 | European Pat. Off.. |
| 0 338 971 | 10/1989 | European Pat. Off.. |
| 357163 A1 | 3/1990 | European Pat. Off.. |

(List continued on next page.)

OTHER PUBLICATIONS

Miller, *Ultrasonics* (Sep. 1981), "Ultrasonic detection of resonant cavitation bubbles in a flow tube by their second–harmonic emissions," pp. 217–2274.

Dittrich, "Cardiac Muscle Ischemia and Infarction", *The Second Annual International Symposium on Contrast Agents in Diagnostic Ultrasound*, Atlantic City, NJ (May 7, 1996) (abstract).

Pantely, "Intravenous Contrast Echocardiography–Tissue Imaging & Quantification of Coronary Blood Flow", *The Second Annual International Symposium on Contrast Agents in Diagnostic Ultrasound*, Atlantic City, NJ (May 7, 1996) (abstract).

(List continued on next page.)

*Primary Examiner*—Gollamudi S. Kishore
*Attorney, Agent, or Firm*—Woodcock Washburn Kurtz Mackiewicz & Norris LLP

[57] ABSTRACT

Gas and gaseous precursor filled microspheres, and foams thereof, provide novel topical and subcutaneous delivery vehicles for various active ingredients, including drugs and cosmetics.

60 Claims, 2 Drawing Sheets

U.S. PATENT DOCUMENTS

| | | | |
|---|---|---|---|
| 3,873,564 | 3/1975 | Schneider et al. | 260/309.6 |
| 3,945,956 | 3/1976 | Garner | 260/2.5 B |
| 3,960,583 | 6/1976 | Netting et al. | 106/122 |
| 4,089,801 | 5/1978 | Schneider | 252/316 |
| 4,108,806 | 8/1978 | Cohrs et al. | 521/54 |
| 4,138,383 | 2/1979 | Rembaum et al. | 260/29.7 H |
| 4,162,282 | 7/1979 | Fulwyler et al. | 264/9 |
| 4,179,546 | 12/1979 | Garner et al. | 521/56 |
| 4,192,859 | 3/1980 | Mackaness et al. | 424/5 |
| 4,224,179 | 9/1980 | Schneider | 252/316 |
| 4,229,360 | 10/1980 | Schneider et al. | 260/403 |
| 4,276,885 | 7/1981 | Tickner et al. | 128/660 |
| 4,310,505 | 1/1982 | Baldeschwieler et al. | 424/1 |
| 4,310,506 | 1/1982 | Baldeschwieler et al. | 424/1 |
| 4,315,514 | 2/1982 | Drewes et al. | 128/653 |
| 4,331,654 | 5/1982 | Morris | 424/38 |
| 4,344,929 | 8/1982 | Bonsen et al. | 424/15 |
| 4,420,442 | 12/1983 | Sands | 264/13 |
| 4,421,562 | 12/1983 | Sands et al. | 106/75 |
| 4,426,330 | 1/1984 | Sears | 260/403 |
| 4,428,924 | 1/1984 | Millington | 424/4 |
| 4,442,843 | 4/1984 | Rasor et al. | 128/660 |
| 4,466,442 | 8/1984 | Hilmann et al. | 128/653 |
| 4,533,254 | 8/1985 | Cook et al. | 366/176 |
| 4,534,899 | 8/1985 | Sears | 260/403 |
| 4,540,629 | 9/1985 | Sands et al. | 428/402 |
| 4,544,545 | 10/1985 | Ryan | 424/1.1 |
| 4,549,892 | 10/1985 | Baker et al. | 65/21.4 |
| 4,569,836 | 2/1986 | Gordon . | |
| 4,572,203 | 2/1986 | Feinstein | 128/661 |
| 4,586,512 | 5/1986 | Do-huu et al. | 128/660 |
| 4,603,044 | 7/1986 | Geho et al. | 424/9 |
| 4,615,879 | 10/1986 | Runge et al. | 424/9 |
| 4,620,546 | 11/1986 | Aida et al. | 128/660 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,675,310 | 6/1987 | Chapman et al. | 514/6 |
| 4,681,119 | 7/1987 | Rasor et al. | 128/660 |
| 4,684,479 | 8/1987 | D'Arrigo | 252/307 |
| 4,689,986 | 9/1987 | Carson et al. | 73/19 |
| 4,718,433 | 1/1988 | Feinstein | 128/660 |
| 4,728,575 | 3/1988 | Gamble et al. | 428/402.2 |
| 4,728,578 | 3/1988 | Higgins et al. | 428/462 |
| 4,731,239 | 3/1988 | Gordon | 424/9 |
| 4,737,323 | 4/1988 | Martin et al. | 264/4.3 |
| 4,774,958 | 10/1988 | Feinstein | 128/660.01 |
| 4,775,522 | 10/1988 | Clark, Jr. | 424/9 |
| 4,776,991 | 10/1988 | Farmer et al. | 264/4.3 |
| 4,781,871 | 11/1988 | West, III et al. | 264/4.3 |
| 4,789,501 | 12/1988 | Day et al. | 252/645 |
| 4,790,891 | 12/1988 | Halliday et al. | 149/2 |
| 4,822,534 | 4/1989 | Lencki et al. | 264/4.3 |
| 4,830,858 | 5/1989 | Payne et al. | 424/450 |
| 4,844,882 | 7/1989 | Widder et al. | 424/9 |
| 4,863,717 | 9/1989 | Keana | 424/9 |
| 4,865,836 | 9/1989 | Long, Jr. | 424/5 |
| 4,877,561 | 10/1989 | Iga et al. | 264/4.3 |
| 4,893,624 | 1/1990 | Lele | 128/399 |
| 4,895,719 | 1/1990 | Radhakrishnan | 424/45 |
| 4,898,734 | 2/1990 | Mathiowitz et al. | 424/426 |
| 4,900,540 | 2/1990 | Ryan et al. | 424/9 |
| 4,921,706 | 5/1990 | Roberts et al. | 424/450 |
| 4,927,623 | 5/1990 | Long, Jr. | 424/5 |
| 4,938,947 | 7/1990 | Nicolau et al. | 424/1.1 |
| 4,957,656 | 9/1990 | Cerny et al. | 252/311 |
| 4,981,692 | 1/1991 | Popescu | 424/422 |
| 4,985,550 | 1/1991 | Charpiot et al. | 536/18.4 |
| 4,987,154 | 1/1991 | Long, Jr. | 514/772 |
| 4,993,415 | 2/1991 | Long | 128/653 A |
| 4,996,041 | 2/1991 | Arai et al. | 424/9 |
| 5,000,960 | 3/1991 | Wallach | 424/450 |
| 5,008,050 | 4/1991 | Cullis et al. | 264/4.3 |
| 5,013,556 | 5/1991 | Woodle et al. | 424/450 |
| 5,019,370 | 5/1991 | Jay et al. | 424/4 |
| 5,045,304 | 9/1991 | Schneider et al. | 424/9 |
| 5,049,388 | 9/1991 | Knight et al. | 424/450 |
| 5,078,994 | 1/1992 | Nair et al. | 424/501 |
| 5,088,499 | 2/1992 | Unger | 128/662.2 |
| 5,114,703 | 5/1992 | Wolf et al. | 424/5 |
| 5,123,414 | 6/1992 | Unger | 128/654 |
| 5,137,928 | 8/1992 | Erbel et al. | 521/56 |
| 5,141,738 | 8/1992 | Rasor | 424/2 |
| 5,147,631 | 9/1992 | Glajch et al. | 424/9 |
| 5,149,319 | 9/1992 | Unger | 604/22 |
| 5,171,755 | 12/1992 | Kaufman | 514/759 |
| 5,186,922 | 2/1993 | Shell et al. | 128/654 |
| 5,190,982 | 3/1993 | Erbel et al. | 521/56 |
| 5,194,266 | 3/1993 | Abra et al. | 424/450 |
| 5,195,520 | 3/1993 | Schlief et al. | 128/660.02 |
| 5,196,183 | 3/1993 | Yudelson et al. | 424/9 |
| 5,198,225 | 3/1993 | Meybeck et al. | 424/450 |
| 5,205,287 | 4/1993 | Erbel | 128/632 |
| 5,205,290 | 4/1993 | Unger | 128/653.4 |
| 5,209,720 | 5/1993 | Unger | 604/22 |
| 5,213,804 | 5/1993 | Martin et al. | 424/450 |
| 5,215,680 | 6/1993 | D'Arrigo | 252/307 |
| 5,219,538 | 6/1993 | Henderson et al. | 428/402.2 |
| 5,228,446 | 7/1993 | Unger | 128/662.02 |
| 5,230,882 | 7/1993 | Unger | 424/9 |
| 5,271,928 | 12/1993 | Schneider et al. | 424/9 |
| 5,281,408 | 1/1994 | Unger | 424/4 |
| 5,305,757 | 4/1994 | Unger et al. | 128/662.02 |
| 5,310,540 | 5/1994 | Giddey et al. | 424/9 |
| 5,315,997 | 5/1994 | Widder et al. | 128/653.3 |
| 5,316,771 | 5/1994 | Barenholtz et al. | 424/450 |
| 5,334,381 | 8/1994 | Unger | 424/9 |
| 5,344,930 | 9/1994 | Riess et al. | 544/84 |
| 5,350,571 | 9/1994 | Kaufman et al. | 424/9 |
| 5,352,435 | 10/1994 | Unger | 424/9 |
| 5,358,702 | 10/1994 | Unger | 424/9 |
| 5,362,478 | 11/1994 | Desai et al. | 424/9 |
| 5,380,519 | 1/1995 | Schneider et al. | 424/9 |
| 5,393,524 | 2/1995 | Quay | 424/9 |
| 5,409,688 | 4/1995 | Quay | 424/9 |
| 5,410,516 | 4/1995 | Uhlendorf et al. | 367/7 |
| 5,413,774 | 5/1995 | Schneider et al. | 424/9.51 |
| 5,425,366 | 6/1995 | Reinhardt et al. | 128/662.02 |
| 5,433,204 | 7/1995 | Olson | 128/661.08 |
| 5,445,813 | 8/1995 | Schneider et al. | 424/9.51 |
| 5,456,900 | 10/1995 | Unger | 424/9.4 |
| 5,469,854 | 11/1995 | Unger et al. | 128/662.02 |
| 5,470,582 | 11/1995 | Supersaxo et al. | 424/489 |
| 5,487,390 | 1/1996 | Cohen | 128/662.02 |
| 5,496,535 | 3/1996 | Kirkland | 424/9.37 |
| 5,498,421 | 3/1996 | Grinstaff et al. | 424/450 |
| 5,505,932 | 4/1996 | Grinstaff et al. | 424/9.3 |
| 5,527,521 | 6/1996 | Unger | 424/93 |
| 5,529,766 | 6/1996 | Klaveness et al. | 424/9.52 |
| 5,531,980 | 7/1996 | Schneider et al. | 424/9.52 |
| 5,536,489 | 7/1996 | Lohrmann et al. | 424/9.52 |
| 5,536,490 | 7/1996 | Klaveness et al. | 424/9.52 |
| 5,540,909 | 7/1996 | Schutt | 424/9.52 |
| 5,547,656 | 8/1996 | Unger | 424/9.4 |
| 5,552,133 | 9/1996 | Lambert et al. | 424/9.52 |
| 5,558,094 | 9/1996 | Quay | 128/662.02 |
| 5,558,853 | 9/1996 | Quay | 424/9.5 |
| 5,558,854 | 9/1996 | Quay | 424/9.52 |
| 5,558,855 | 9/1996 | Quay | 424/9.5 |
| 5,560,364 | 10/1996 | Porter | 128/662.02 |
| 5,562,893 | 10/1996 | Lohrmann | 424/9.52 |
| 5,567,413 | 10/1996 | Klaveness et al. | 424/9.51 |

| | | | |
|---|---|---|---|
| 5,567,414 | 10/1996 | Schneider et al. | 424/9.52 |
| 5,567,765 | 10/1996 | Moore et al. | 524/801 |
| 5,573,751 | 11/1996 | Quay | 424/9.52 |
| 5,595,723 | 1/1997 | Quay | 424/9.5 |
| 5,606,973 | 3/1997 | Lambert et al. | 128/662.02 |
| B1 4,229,360 | 11/1991 | Schneider et al. | 260/403 |

FOREIGN PATENT DOCUMENTS

| | | |
|---|---|---|
| 0 361 894 | 4/1990 | European Pat. Off. . |
| 0 216 730 | 1/1991 | European Pat. Off. . |
| 0 467 031 A2 | 5/1991 | European Pat. Off. . |
| 441468 A2 | 8/1991 | European Pat. Off. . |
| 0 357 164 B1 | 10/1991 | European Pat. Off. . |
| 0 458 745 A1 | 11/1991 | European Pat. Off. . |
| 0 314 764 B1 | 9/1992 | European Pat. Off. . |
| 0 554 213 A1 | 8/1993 | European Pat. Off. . |
| 0 727 225 A2 | 8/1996 | European Pat. Off. . |
| 62-286534 SHO | 12/1987 | Japan . |
| 63-60943 | 3/1988 | Japan . |
| 1044680 | 10/1966 | United Kingdom . |
| 2193095 | 2/1988 | United Kingdom . |
| 80/02365 | 11/1980 | WIPO . |
| 82/01642 | 5/1982 | WIPO . |
| 85/01161 | 3/1985 | WIPO . |
| 86/00238 | 1/1986 | WIPO . |
| 86/01103 | 2/1986 | WIPO . |
| 89/05040 | 6/1989 | WIPO . |
| 90/01952 | 3/1990 | WIPO . |
| 90/04384 | 5/1990 | WIPO . |
| 90/04943 | 5/1990 | WIPO . |
| 91/00086 | 1/1991 | WIPO . |
| 91/12823 | 9/1991 | WIPO . |
| 91/15244 | 10/1991 | WIPO . |
| 92/10166 | 6/1992 | WIPO . |
| 92/11873 | 7/1992 | WIPO . |
| 92/17212 | 10/1992 | WIPO . |
| 92/17213 | 10/1992 | WIPO . |
| 92/17436 | 10/1992 | WIPO . |
| 92/21382 | 12/1992 | WIPO . |
| 93/05819 | 1/1993 | WIPO . |
| 93/06869 | 4/1993 | WIPO . |
| 93/13809 | 7/1993 | WIPO . |
| 93/17718 | 9/1993 | WIPO . |
| 93/20802 | 10/1993 | WIPO . |
| WO 94/06477 | 3/1994 | WIPO . |
| 94/09829 | 5/1994 | WIPO . |
| 94/16739 | 8/1994 | WIPO . |
| 94/21302 | 9/1994 | WIPO . |
| 95/07072 | 3/1995 | WIPO . |
| WO 95/06518 | 3/1995 | WIPO . |
| 95/23615 | 9/1995 | WIPO . |
| WO 96/04018 | 2/1996 | WIPO . |
| WO 96/09793 | 4/1996 | WIPO . |
| 96/36286 | 11/1996 | WIPO . |

OTHER PUBLICATIONS

Schutt et al., "Osmotically Stabilized Microbubble Sonographic Contrast Agents", *Acad. Radiol.*, vol. 3, Suppl. 2, pp. S188–S190 (Aug. 1996).

Frézard, et al., "Permeability and stability in buffer and in human serum of fluorinated phospholipid–based liposomes", *Biochimica et Biophysica Acta*, 1192, pp. 61–70 (1994).

Frézard, et al., "Fluorinated Phospholipid–Based Vesicles as Potential Drug Carriers: Encapsulation/Sustaining of Drugs and Stability in Human Serum", *Art, Cells, Blood Subs., and Immob. Biotech.*, 22(4), pp. 1403–1408 (1994).

Ophir et al., "Contrast Agents in Diagnostic Ultrasound", *Ultrasound in Med. & Biol.*, vol. 15, No. 4, pp. 319–333 (1989).

Jacobs, "Intraocular gas measurement using A–scan Ultrasound", *Current Eye Research*, vol. 5, No. 8, pp. 575–578 (1986).

Moseley, et al., *Microbubbles: A Novel MR Susceptibility Contrast Agent*, Abstract, 1991 Napa, California Meeting of the Society for Magnetic Resonance in Medicine.

Ter–Pogossia *Tomography*, Kee, et al., n, "Physical Principles and Instrumentation", *Computed Body* eds., Raven Press, New York, Chapter 1, pp. 1–7 (1988).

Aronberg, "Techniques", *Computed Body Tomography*, Kee, et al., eds., Raven Press, New York, Chapter 2, pp. 9–36 (1988).

Mattrey et al., Gas Emulsions as Ultrasound Contrast Agents; Preliminary Results in Rabbits and Dogs, *Investigative Radiology*, vol. 29, Jun. Supp. 2, pp. S139–S141, 1994.

Meltzer et al., Transmission of Ultrasonic Contrast Through the Lungs, *Ultrasound in Med. & Biol.*, vol. 7, No. 4, 377–384, 1981.

Chang et al., "Semipermeable Aqueous Microcapsules", *Canadian J. of Phys. and Pharm.*, 1966, 44, 115–128.

Chang, "Semipermeable Microcapsules", *Science*, 1964, 146, 524–525.

Deasy, *Microencapsulation and Related Drug Processes*, 1983, vol. 20, Chs. 9 and 10, 195–240 (Marcel Dekker, Inc., NY).

Yeung et al., "Preparation of Microencapsulated Liposomes", *J. Microencapsulation*, 1988, 5, 331–337.

PR Newswire, Apr. 1, 1986.

Swanson et al., Chapter 22, "Enhancement Agents for Ultrasound: Fundamentals", *Pharmaceuticals in Medical Imaging*, pp. 682–687 (1990).

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, vol. 13, No. 3, pp. 568–574 (1994).

Thanassi, "Aminomalonic Acid: Spontaneous Decarboxylation and Reaction with 5–Deoxypyridoxal", *Biochemistry*, vol. 9, No. 3, pp. 525–532 (1970).

Stelmashok et al., *Koordinatsionnaya Khimiya*, vol. 3, No. 4, pp. 524–527 (1977) (Russian and English language versions).

Mayhew et al., "High–Pressure Continuous–Flow System for Drug Entrapment in Liposomes", *Methods in Enzymology*, vol. 149, pp. 64–77 (1987).

Mayhew et al., "Characterization of Liposomes Prepared Using a Microemulsifier", *Biochimica et Biophysica Acta*, vol. 775, pp. 169–174 (1984).

Hope et al., "Production of Large Unilamellar Vesicles by a Rapid Extrusion Procedure: Characterization of Size Distribution, Trapped Volume, and Ability to Maintain a Membrane Potential", *Biochimica et Biophysica Acta*, 812: 55–65 (1985).

Mayer et al., "Vesicles of Variable Size Produced by a Rapid Extrusion Procedure", *Biochimica et Biophysica Acta*, vol. 858, pp. 161–168 (1986).

Cheng, et al., "The Production and Evaluation of Contrast–Carrying Liposomes Made with an Automatic High Pressure System", *Investigative Radiology*, vol. 22, pp. 47–55 (1987).

Jain, et al., *Introduction to Biological Membranes*, Ch. 9, pp. 192–231 (J. Wiley and Sons, N.Y. 1980).

Sigel, H., ed., *Metal Ions in Biological Systems: Antibiotics and Their Complexes*, vol. 19 (Marcel Dekker, N.Y. 1985).

Nayer et al., "Generation of Large Unilamellar Vesicles From Long–chain Saturated Phosphatidylcholines by Extrusion Technique", *Biochimica et Biophysica Acta*, vol. 986, pp. 200–206 (1989).

Hope et al., "Generation of Multilamellar and Unilamellar Phospholipid Vesicles", *Chemistry and Physics of Lipids*, vol. 40, pp. 89–107 (1986).

Mattrey et al., "Perfluorochemicals as US Contrast Agents for Tumor–Imaging and Hepatosplenography: Preliminary Clinical Results", *Radiology*, vol. 163, pp. 339–343 (1987).

Mattrey et al., "Perfluoroctylbromide: A Liver/Spleen–Specific and Tumor Imaging Ultrasound Contrast Material", *Radiology*, vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570–575 (1987).

Feinstein et al., "Two–Dimensional Contrast Echocardiography, I: In Vitro Development and Quantitative Analysis of Echo Contrast Agents", *JACC*, vol. 3, No. 1, pp. 14–20 (1984).

Ten Cate et al., "Two–Dimensional Contrast Echocardiography, II: Transpulmonary Studies", *JACC*, vol. 3, No. 1, pp. 21–27 (1984).

Unger et al., "Hepatic Metastases: Liposomal Gd–DTPA–enhanced MR Imaging", *Radiology*, vol. 171, pp. 81–85 (1989).

Deamer et al., "Permeability of Lipid Bilayers to Water and Ionic Solutes", *Chemistry and Physics of Lipids*, vol. 40, pp. 167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts*, 87:34772q (1977).

Scarpa et al., "Cation Permeability of Liposomes as a Function of the Chemical Composition of the Lipid Bilayers", *Biochimica et Biophysica Acta*, vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta*, vol. 597, pp. 193–198 (1980).

Tilcock et al., "Liposomal Gd–DTPA: Preparation and Characterization of Relaxivity", *Radiology*, vol. 171, pp. 77–80 (1989).

Mann et al., "Formation of Iron Oxides in Unilamellar Vesicles", *Journal of Colloid and Interface Science*, vol. 122, No. 2, pp. 326–335 (1988).

Anderson et al., "Manganese (III) Complexes in Oxidative Decarboxylation of Acids", *J. Am. Chem. Soc.*, vol. 92, No. 8, pp. 2450–2460 (1970).

Muhlradt et al., "Vitamin B6 Analogs: An Improved Synthesis of 5–Deoxypyridoxal", *New Compounds*, vol. 10, pp. 129–130 (1967).

Chapman D., "Physiochemical Properties of Phospholipids and Lipid Water Systems", *Liposome Technology*, Gregoriadis, G., ed., vol. 1, pp. 1–19 (CRC Press, Boca Raton, FL, 1984).

Violante et al., "Particulate Suspensions as Ultrasonic Contrast Agents for Liver and Spleen", *Inv. Rad.*, vol. 23, pp. S294–S297, Sep. 1988.

Fritzsch et al., "Preclinical and Clinical Results with an Ultrasonic Contrast Agent", *Inv. Rad.*, vol. 23, pp. S302–S305, Sep. 1988.

Brochure, *Experience*, Sonicator™, Heat Systems–Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimethylammonium Methacrylate", *J. Am. Chem. Soc.*, vol. 108, pp. 2321–2327 (1986).

Regen, "Polymerized Vesicles", *J. Am. Chem. Soc.*, vol. 102, pp. 6638–6640 (1989).

Rose, A. and Rose, E., "The Condensed Chemical Dictionary", Reinhold Publishing, New York, pp. 728 and 743 (1966).

A.G. Belykh, *Fermakol Toksikol. (MOSC)*, vol. 44(3), pp. 322–326 (1981) (abstract).

J. Vion–Dury et al., *J. Pharmacol. Exper. Ther.*, vol. 250(3), pp. 1113–1118 (1989) (abstract).

M.R. Zalutsky et al., *Invest. Radiol.*, vol. 22(2), pp. 141–147 (1987) (abstract).

Crowe et al., *Archives of Biochemistry and Biophysics*, vol. 242, pp. 240–247 (1985).

Crowe et al., *Archives of Biochemistry and Biophysics*, vol. 220, pp. 477–484 (1983).

Dorland's Illustrated Medical Dictionary, p. 946, 27th ed. (W.B. Saunders Company, Philadelphia 1988).

*Liposome Technology*, Gregoriadis, G., ed., vol. I, pp. 1–18, 29–35, 51–65 and 79–107 (CRS Press Inc., Boca Raton, FL, 1984).

Madden et al., *Chemistry and Physics of Lipids*, vol. 53, pp. 37–46 (1990).

Sinkula et al., *J. Pharm. Sci.*, vol. 64, pp. 181–210 (1975).

Shiina et al., "Hyperthermiaby Low–frequency Synthesized Ultrasound", *IEEE Engineering*, pp. 879–880, vol. 2 (abstract).

McAvoy et al., *IEEE Engineering, Ultrasonics Symposium Proceedings*, vol. 2, pp. 677–1248 (abstract).

Chapman et al., "Biomembrane Phase Transitions", *J. Biol;. Chem.*, 1974, 249:2512–2521.

Hug et al., "Liposomes for the Transformation of Eukaryotic Cells", *Biochimica et Biophysica Acta*, 1991, 1097:1–17.

Marsh, *CRC Handbook of Lipid Bilayers* (CRC Press, Boca Raton, FL 1990) pp. 139–141.

Szoka et al., "Procedure for Preparation of Liposomes With Large Internal Aqueous Space . . . ", *Proc. Natl. Acad. Sci.* 1978, 75:4194–4198.

Acoustic Imaging; A15200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.*, 1965, 13:238–252.

Carson et al., *Ultrasound in Med. & Biol.* 3, 1978, 341–350.

Chiellini et al., *Polymers in Medicine II: Biomedical and Pharmaceutical Applications*, (Plenum Press, New York and London) pp. 387–396.

deGier et al., "Relations Between Liposomes and Biomembranes", *Annals of the New York Academy of Sciences*, 1978, 308:85–99.

Felgner et al., "Lipofection: A highly efficient, lipid–mediated DNA–transfection procedure", *Proc. Natl. Acad. Sci.*, 1987, 84:7413–7417.

Gabizon et al., "Liposome formulations with prolonged circulation time in blood and enhanced uptake by tumors", *Proc. Natl. Acad. Sci.*, 1988, 85:6949–6953.

Garelli, et al., *Biochimica et Biophysica Acta*, vol. 1127:41–48 (1992).

Kawai et al., "New Procedure for DNA Transfection with Polycation and Dimethyl Sulfoxide", *Molecular and Cellular Biology*, 1984, 4:1172–1174.

Kuo et al., "Metallocene Antitumor Agents. Solution and Solid–State Molybdenocene Coordination . . . ", *J. Am. Chem. Soc.*, 1991, 113:9027–9045.

*Mammalian Cell Biotechnology: A Practical Approach*, M. Butler, 1991 (Oxford University Press, New York), pp. 57–70.

Mathiowitz et al., "Photochemical Rupture of Microcapsules: A Model System", *Journal of Applied Polymer Science*, 1981, 26:809–822.

May et al., "Cationic Liposomes Enable Bovine Herpesvirus Type 2 DNA to Infect Cells", *Acta virol.*, 1991, 35:107.

Poznansky et al., "Biologica Approaches to the Controlled Delivery of Drugs: A Critical Review", *Pharmacol, Rev.*, 1984, 36:277–336.

Sato et al., "Recent Aspects in the Use of Liposomes in Biotechnology and Medicine", *Prog. Lipid Res.* 1992, 4:345–372.

Simons et al., "Antisense c–myb oligonucleotides inhibit intimal arterial smooth muscle cell accumulation in vivo", *Nature*, 1992, 359:67–70.

Thompson, Larry, "At Age 2, Gene Therapy Enters a Growth Phase", *Science* 1992, 258:744–746.

Trubetskoy et al., "Cationic liposomes enhance targeted delivery and expression of exogenous DNA . . . ", Biochimica et Biophysica Acta 1992, 131:311–313.

Umemura et al., "Studies on Sonodynamic Cancer Therapy", *IEEE*, 1992, O–7803–0785, pp. 354–355.

Williams, "Human Gene Therapy: Searching for Better Vectors", *ASM News* [American Society for Microbology] 1992, 58:67–69.

Woodle et al., "Versatility in lipid compositions showing prolonged circulation . . . ", *Biochimica et Biophysica Acta* 1992, 1105:193–200.

Zhou et al., "Targeted delivery of DNA by liposomes and polymers", *J. of Controlled Release* 1992, 19:269–274.

Mathiowitz et al., "Polyanhydride Microspheres as Drug Carriers", *Journal of Applied Polymer Science*, vol. 35, pp. 755–774 (1988).

Sankaram et al., "Cholesterol–Induced Fluid–Phase Immiscibility in Membranes", *Proc. Natl. Acad. Sci.*, vol. 88, pp. 8686–8690 (1991).

*Scientific Apparatus Catalog 92/93* (VWR Scientific, 1991), "Syringes", pp. 1511–1513; Filtration, Syringe Filters, pp. 766–768; Filtration, Membranes, pp. 750–753; Filtration, Filter Holders, p. 744.

Gramiak et al., *Radiology*, "Detection of Intracardiac Blood Flow by Pulsed Echo–Ranging", pp. 415–418 (1971).

Feigenbaum et al., *Circulation*, "Identification of Ultrasound Echoes from the Left Ventricle by Use of Intracardiac Injections of Indocyanine Green", vol. XL1, pp. 615–621 (1970).

Santaella, et al., *FEBS 13463*, "Extended In Vivo Blood Circulation Time of Fluorinated Liposomes", vol. 336, No. 3, pp. 481–484 (1993).

Kost, et al., *Polymers in Medicine II*, "Ultrasonic Modulated Drug Delivery Systems, pp. 387–396.

Brown and Langer, *Annual Review Medicine*, 1988, 39:221 29, Annual Review, Inc., "Transdermal Delivery of Drugs", pp. 221–229.

Ter–Pogossian, *Physical Principles and Instrumentation*, "Computed Body Tomography", Chapter 1, pp. 1–7.

• THERAPEUTIC AGENT(2)
○ GAS-FILLED MICROSPHERES(1)

ID
GAS AND GASEOUS PRECURSOR FILLED MICROSPHERES AS TOPICAL AND SUBCUTANEOUS DELIVERY VEHICLES

REFERENCE TO COPENDING APPLICATIONS

This application is a continuation-in-part of application U.S. Ser. No. 159,674, filed Nov. 30, 1993 now abandoned, which in turn is a continuation-in-part of applications U.S. Ser. No. 076,239, now U.S. Pat. No. 5,469,854 and U.S. Ser. No. 076,250 now U.S. Pat No. 5,580,575, both of which were filed Jun. 11, 1993, which in turn are continuation-in-parts of applications U.S. Ser. No. 717,084, now U.S. Pat. No. 5,228,446 and U.S. Ser. No. 716,899, now abandoned, both of which were filed Jun. 18, 1991, which in turn are continuation-in-parts of application U.S. Ser. No. 569,828, filed Aug. 20, 1990 now U.S. Pat. No. 5,088,499 which in turn is a continuation-in-part of application U.S. Ser. No. 455,707, filed Dec. 22, 1989, now abandoned.

This application is also a continuation-in-part of application U.S. Ser. No. 307,305, filed Sep. 16, 1994, pending, and applications U.S. Ser. No. 159,687, now U.S. Pat. No. 5,585,112 and U.S. Ser. No. 160,232, now U.S. Pat. No. 5,542,935 both of which were filed Nov. 30, 1993, which in turn are continuation-in-parts, respectively, of applications U.S. Ser. No. 076,239, now U.S. Pat. No. 5,469,854 and U.S. Ser. No. 076,250, now U.S. Pat. No. 5,580,575 both of which were filed Jun. 11, 1993.

Priority to each of these applications is hereby claimed, and the disclosures of each are hereby incorporated herein by reference in their entirety.

BACKGROUND OF THE INVENTION

1. Field of the Invention

The present invention relates to the field of methods and compositions for the topical administration of active ingredients, especially drugs and cosmetics, to a selected tissue of a patient, especially the skin. While topical administration will ordinarily and predominantly be administration to the skin of a patient, as used in the description herein of the present invention the term topical is not limited thereto, but includes administration to any and all tissue surfaces of a patient, whether external or internal. Thus, in addition to a patient's skin, other sites of topical administration include various mucosal membranes such as those of the eye, nose, rectum and vagina. Also included within the scope of the present invention is topical administration to the lungs, i.e., to the bronchi, bronchioli, and alveoli, either singly or collectively.

While administration is made topically to the desired tissue surface (that is, locally or directly to the tissue surface) absorption and transfer from the local place of administration to other areas or regions of the patient, especially systemically via the blood, may occur. Thus, while the topical application is local (for example, directly to the lungs or portions thereof), there may be systemic carryover, if desired, resulting in delivery of the drug to the various other regions of the patient's body. In certain situations, however, systemic carryover may not be necessary or desired, such as in the case of certain drugs for the treatment of bronchitis or asthma where topical application to the mucous membranes of the lungs may be all that is required.

The present invention also includes within the meaning of the term topical, the application of the compositions described further below to specific tissues of a patient which, although under ordinary circumstances are fully internal and not accessible to topical administration, may become exposed as a result of, e.g., surgery or trauma. Thus, it would be within the scope of the present invention to apply the compositions thereof to the exposed tissues of a heart during the course of open heart surgery.

The present invention is also directed to the administration of active ingredients subcutaneously, that is below the surface of the patient's tissue, especially skin, by injection. Subcutaneous injections permit the formation of depots (a below the surface repository) of active ingredients, allowing for a sustained release of the active ingredient into the patients system. While subcutaneous administration will ordinarily and predominantly be administration by injection underneath the skin of a patient, as used in the description herein of the present invention the term subcutaneous is not limited thereto, but includes administration by injection below any and all tissue surfaces of a patient, whether external or internal. Thus, in addition to a patient's skin, other sites of subcutaneous administration include underneath the surface of a patient's eye or heart outer membrane.

There is an ongoing need for improved methods and compositions in this field because topical and subcutaneous delivery of active ingredients, especially therapeutic agents, to a desired localized site of action can often be made at higher concentrations than would be possible systemically without encountering undesired side effects. Also, it is well recognized that most drugs and cosmetics are poorly absorbed, or even retained on the surface of the skin in the first place, where that is the site of topical or subcutaneous application. In the case of drugs, absorption by or below the surface of the skin is generally slow, and therefore, usually ineffective. In the case of cosmetics, particularly vitamins and their derivatives, and sun screen agents, it is difficult to prevent these compounds from being washed off the skin, just as it is similarly difficult to get these compounds to penetrate into the skin.

Topical and subcutaneous delivery of therapeutic agents can also have as its objective systemic administration to the patient of the agent in question, i.e., the raising of the plasma levels of the drug involved in the patient to which it is administered. Thus, the field of the present invention also includes methods and compositions for application of active ingredients to or below the skin for the purpose of achieving transdermal or systemic delivery of the active ingredient, i.e., supplying the active ingredient in a form for absorption through and below the skin into the bloodstream. It is also within the scope of the present invention to administer said compositions to mucosal and other tissues as described above, for the purpose of achieving transdermal or systemic administration of the active ingredient involved.

2. Brief Description of the Prior Art

A wide variety of topical and subcutaneous delivery systems have been developed in the prior art for delivering active ingredients such as drugs and cosmetics to various tissues of a patient, especially to the skin and through the skin via topical application. In order to improve the penetration of drugs and cosmetics into the skin, a variety of techniques and materials have been tried in the past. These include iontophoresis and ultrasound to improve penetration of drugs into the skin, and the use of formulations containing penetration enhancing compounds, surfactants, lipids and other aliphatic compounds, liposomes and niosomes. While all of these agents have to some extent appeared to increase the absorption of drugs and in some cases the efficacy of cosmetics, nothing yet developed has possessed the desired optimal characteristics. The most advanced formulations to date for skin delivery of drugs and cosmetics may be the liposomes or the niosomes, but these agents also suffer from several drawbacks. For example, it has been difficult to create stable, pharmaceutically acceptable formulations using them, and the active ingredients contained in them, as well as the lipid or aliphatic compounds from which they are made, may oxidize or hydrolyze during storage or be degraded even after they are applied to the skin.

Heretofore, in particular, aqueous-filled liposomes have been utilized to deliver drugs to the skin. Liposomes are vesicles composed of one or more concentric phospholipid layers, which are usually referred to as being uni-, oligo-, and multilamellar, and typically when they are filled with an aqueous solution of active ingredient, the interior space of the liposome is in equilibrium with gas on the outside of the liposomes, so that there is an exchange of oxygen across the liposome membrane. This results in oxidative degradation of the active ingredient encapsulated therein. Examples of drugs that can be oxygen sensitive are the fat-soluble Vitamins A, E, D, and K, water soluble vitamins such as Vitamin C, ferrous based salts, penam, cepham and monobactam antibiotics via hydrolysis, chemotherapeutic agents, and so forth.

There has been no appreciation in the art that it would be possible to prepare gas and gaseous precursor filled liposomes and foam as are made in accordance with the specific procedures of the present invention and that such microspheres and foams would possess significant advantages with respect to topical delivery of various active ingredients to the skin. Foaming has also been an incidental occurrence during prior art procedures for preparing liposomes and other microvesicles; however, there again has been no appreciation that it would be possible or even desirable to prepare gas and gaseous precursor filled liposomes and foam thereof of the present invention as vehicles for topical or subcutaneous delivery of various active ingredients.

For example, Ryan et al. U.S. Pat. No. 4,900,540 entitled "Lipisomes (sic) Containing Gas for Ultrasound Detection" suggests, with regard to liposomes containing gas and gaseous precursors, only that they can be utilized by being suspended in a physiologically acceptable liquid such as saline and administered parenterally and by other routes, for use as a diagnostic ultrasound contrast agent, none of which, however, is said to include such applications as topical administration to the skin.

Tickner et al. WO 80/02365 entitled "Ultrasonic Image Enhancement", provides a method of enhancing ultrasonic images of the blood stream of a patient by flowing therethrough a plurality of microbubbles having a surface membrane, such as gelatin, encapsulating a gas. However, it is preferred that the microbubbles be formed and dispersed in a medium having a chemical composition substantially identical to that of the membrane, and that it be gellable. Such compositions would, presumably, not be useful as foams; also there is clearly no intention to use the compositions in any topical or subcutaneous applications.

In *Proc. Natl. Acad. Sci. USA*, 75 (1978) 4194–4198, Szoka and Papahadjopoulos, in an article entitled "Procedure for preparation of liposomes with a large aqueous space and high capture by reverse-phase evaporation", describe sonication of a two-phase system followed by evaporation of solvent during which the system is seen to froth. However, this is followed by formation of a viscous gel and then an aqueous suspension, after which nonencapsulated material and residual organic solvent are removed. The liposomes produced are not gas and gaseous precursor filled, and moreover, there is no suggestion of the formation of a microsphere or foam for topical application. Similarly, Hug and Sleight, in *Biochimica et Biophysica Acta*, 1097 (1991) 1–17, describe reverse-phase evaporation encapsulation in which they recommend substituting rapid vortexing for sonication. However, as discussed above, gas and gaseous precursor filled liposomes are not being prepared, a merely transitory, intermediate step is involved, and the end product is not a stable foam.

Cerny et al. U.S. Pat. No. 4,957,656 entitled "Continuous Sonication Method for Preparing Protein Encapsulated Microbubbles", discloses an ultrasonic imaging agent produced by continuous sonication processing of an aqueous solution of heat-denaturable biocompatible protein, during which a gaseous fluid, preferably air, is added to the solution. During sonication, the air-containing solution is foamed in order to increase the formation and concentration of microbubbles, but such a foam is not regarded as desirable in the final product, since it is taught that the foam can then be easily dissipated, once the product is removed from the sonication chamber.

Different approaches have been taken in the prior art to overcoming the various factors which restrict the use of liposomes as practical carriers of biologically active compounds, e.g., the limited physical stability of aqueous dispersions of liposomes. Thus, Payne et al. in U.S. Pat. No. 4,830,858 describe a method for preparing a stable liposome precursor in the form of a mixture of spray-dried liposomal components which may be stored dry and reconstituted with water to form a liposomal preparation immediately prior to use. However, to date there has been no suggestion of the discovery of the present invention, i.e., that lipids and other compounds, as defined further below, may be used to formulate stable gas and gaseous precursor filled microspheres and foams with improved qualities for delivery of pharmaceutical and other active ingredients to such areas as the skin.

D'Arrigo U.S. Pat. Nos. 4,684,479 and 5,215,680 disclose gas-in-liquid emulsions and lipid-coated microbubbles, respectively, which are stable and said to be useful in several fields, including as contrast agents for echocardiography, and in the ultrasonic monitoring of local blood flow. However, there is no suggestion that these compositions would be useful for the topical or subcutaneous delivery of active ingredients.

Vanderipe, published PCT application WO 93/06869 also discloses the use of bubbles of gases and gas mixtures, including perfluorocarbons, as ultrasound imaging enhancement agents. However, these gas bubbles are not encapsulated and there is no suggestion of their use in topical or subcutaneous delivery of active ingredients.

Lanza et al. published PCT application WO 93/20802 discloses acoustically reflective oligolamellar liposomes for ultrasonic image enhancement, which are multilamellar liposomes with increased aqueous space between bilayers or have liposomes nested within bilayers in a nonconcentric fashion, and thus contain internally separated bilayers. Their use in monitoring a drug delivered in a liposome administered to a patient, is also described. However, there is no teaching of the stabilized gas and gaseous precursor filled microspheres or foams of the present invention or the use thereof in such applications as the topical delivery of active ingredients.

Widder et al. published European application EP-A-0 324 938 discloses stabilized microbubble-type ultrasonic imaging agents produced from heat-denaturable biocompatible protein, e.g., albumin, hemoglobin, and collagen. Again, however, use of such compositions for such applications as the topical delivery of active ingredients is not described.

There is also mentioned a presentation made by Moseley et al. in 1991 at the Society for Magnetic Resonance in Medicine meeting in San Francisco, Calif., which is summarized in an abstract entitled "Microbubbles: A Novel MR Susceptibility Contrast Agent". The microbubbles which are utilized comprise air coated with a shell of human albumin. The stabilized gas and gaseous precursor filled microspheres and foams of the present invention and the use thereof for such applications as the topical delivery of active ingredients is not, however, suggested.

Tei et al. unexamined patent application disclosure SHO 63-60943 discloses contrast agents for ultrasonic diagnosis comprising a perfluorocarbon emulsion with an emulsion particle size of 1-10 μm, in which the perfluorocarbon is preferable of 9-11 carbon atoms and the emulsifier may be, e.g., a phospholipid or a nonionic polymeric surfactant such as poly(oxyethylene)-poly(oxypropylene) copolymers. The emulsion may be prepared by utilizing a mixer. There is no suggestion, however, that these perfluorocarbon emulsions would be suitable for such applications as topical delivery of active ingredients.

Knight et al. U.S. Pat. No. 5,049,388 discloses small particle aerosol liposome and liposome-drug combinations for medical use, e.g., drug delivery to the respiratory tract by inhalation. However, there is no suggestion that these liposomes can be gas or gaseous precursor filled, and they are thus distinguishable from the stabilized gas and gaseous precursor filled microspheres and foams of the present invention.

SUMMARY OF THE INVENTION

In accordance with the present invention there is provided compositions comprising gas and/or gaseous precursor filled microspheres, wherein said microspheres further comprise an effective amount of an active ingredient for topical or subcutaneous application to a selected tissue of a patient. The active ingredients include drugs, especially peptides and other bioactive compounds, as well as cosmetics. The gas entrapped in said microspheres may serve to prevent oxidation and other forms of degradation of labile drugs, bioactive compounds and cosmetics. The gas may be, e.g., nitrogen or perfluoro-propane, but may also be derived from a gaseous precursor, e.g., perfluorooctylbromide, and the microspheres may be formed from, e.g., a biocompatible lipid or polymer. The lipid may be in the form of a monolayer or bilayer, and the mono- or bilayer lipids may be used to form a series of concentric mono- or bilayers. Thus, the lipid may be used to form a unilamellar liposome (comprised of one monolayer or bilayer lipid), an oligolamellar liposome (comprised of two or three monolayer or bilayer lipids) or a multilamellar liposome (comprised of more than three monolayer or bilayer lipids). Preferably, the biocompatible lipid is a phospholipid. The resultant gas or gaseous precursor filled microsphere composition, which often takes the form of a foam, provides a very creamy texture and skin penetration enhancing qualities for the topical or subcutaneous delivery of active ingredients such as pharmaceuticals and cosmetics.

The present invention also concerns a method for preparing gas and/or gasesous precursor filled lipid based microspheres comprising an active ingredient for topical or subcutaneous application to a selected tissue of a patient comprising the step of agitating an aqueous suspension of the biocompatible lipid (that is, the lipid stabilizing compound) in the presence of a gas and/or gaseous precursor, resulting in gas and/or gaseous precursor filled microspheres. The agitation step is desirably carried out at a temperature below the gel to liquid crystalline phase transition temperature of the lipid, in order to achieve a preferred end product. The active ingredient may be added to the aqueous suspension before agitation, or may be added after agitation; in both cases the active ingredient will be associated with the gas and gaseous precursor filled microsphere.

Where a gaseous precursor is used, the gaseous precursor filled microsphere composition is generally maintained at a temperature at which the gaseous precursor is liquid until administration to the patient. At the time of administration the temperature may, if desired, be raised to activate the gaseous precursor to form a gas and the resultant gas filled microsphere then topically or subcutaneously applied to the patient. Alternatively, the gaseous precursor filled microspheres may, if desired, be applied without raising the temperature, and the gaseous precursor allowed to form a gas as a result of the temperature of the tissue surface of the patient (e.g., the patient's skin). The composition may be agitated, if necessary, prior to administration.

In accordance with the present invention there is further provided a method for the topical or subcutaneous delivery of an active ingredient to a selected tissue of a patient comprising the step of topically or subcutaneously applying to said tissue of said patient gas and/or gaseous precursor filled microspheres, wherein said microspheres further comprise an effective amount of said active ingredient. The active ingredients include drugs, especially peptides and other bioactive compounds, as well as cosmetics.

DETAILED DESCRIPTION OF THE INVENTION

Figure 1A:
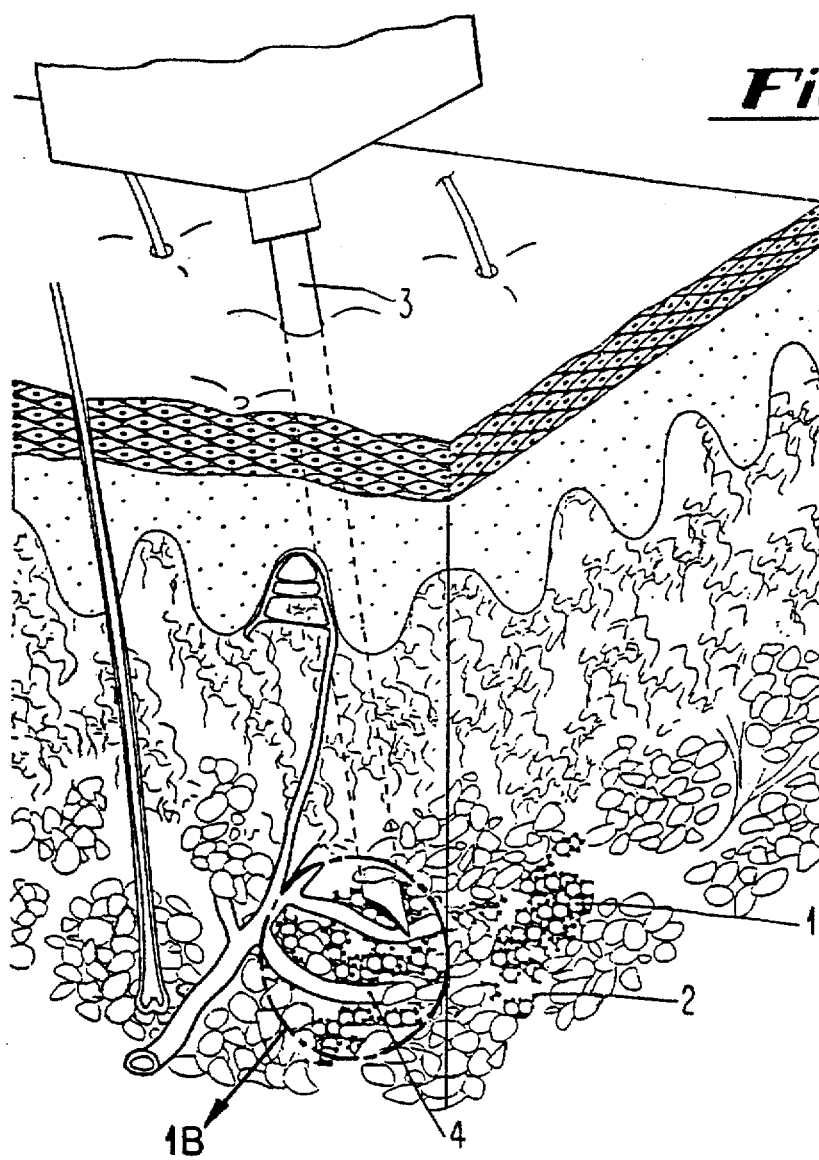
FIGS. 1A and B graphically illustrates the subcutaneous delivery of the gas filled microspheres and active ingredients of the present invention to the skin of a patient.

The present invention pertains to the use of microspheres filled with gas and/or gaseous precursors as vehicles for topical and subcutaneous administration. The microspheres are comprised of biocompatable lipids and/or polymers, which form a skin or membrane which encapsulates or surrounds (i.e., forms a cavity or void around) the gas or gaseous precursor. The lipids and/or polymers provide structural integrity to the microsphere, and give it functional duration for a useful period of time. The present invention more particularly relates to gas and gaseous precursor filled microspheres, wherein said microspheres further comprise an effective amount of an active ingredient for topical or subcutaneous application to a selected tissue of a human or animal patient to which said microsphere is applied. The resultant microsphere composition often takes the visual form of a foam, which is a matrix (aggregation or conglomoration) of microspheres in a liquid medium, and as such are referred to herein as foams or stabilized foams. If desired, the microspheres comprising the foam may be dispersed or separated, using any of a variety of means well known to those skilled in the art. Preferably, however, the microspheres are administered in the form of a foam.

The most useful stabilizing compounds for use in preparing the microsphere wall are typically those which have a hydrophobic/hydrophilic character which allows them to form bilayers, and thus microspheres, in the presence of a water based medium. Thus, water, saline or some other water based medium, often referred to hereafter as a diluent, may be an aspect of the gas and gaseous precursor filled microspheres of the present invention, where such bilayer forming compositions are used as the stabilizing compounds.

The stability of the resultant microspheres and foam of the present invention is attributable, at least in part, to the materials from which they are made. The stabilizing compound may, in fact, be a mixture of compounds which contribute various desirable attributes to the microspheres and foam. For example, compounds which assist in the dissolution or dispersion of the fundamental stabilizing compound have been found advantageous. It is not necessary to employ auxiliary stabilizing additives, although it is optional to do so, and such auxiliary stabilizing agents would be within the skill of the artisan to select, once instructed by the description of the present invention contained herein. The materials from which the microspheres and foam of the present invention are constructed are referred to herein generally as stabilizing compounds, which may be, e.g., biocompatible lipid and polymer materials, although other materials which are described in detail further below may also be used, as may some materials that can function either as basic stabilizing compounds, or as auxiliary stabilizing compounds.

As indicated, the microspheres of the present invention may encapsulate a gas, such as nitrogen or perfluoropropane, which is gaseous at temperatures well above and well below ambient room temperature, or the microspheres may encapsulate gaseous precursors, such as perfluorooctylbromide, which are liquid at ambient room temperature, but at the body temperature of a patient to which they have been administered, expand to form a gas.

Moreover, it is possible to utilize a gas and a gaseous precursor together. Indeed, a unique embodiment of the present invention results from the discovery that a perfluorocarbon gaseous precursor when combined with a gas to make the stabilized microspheres of the present invention, confers an added degree of stability not otherwise obtainable with the gas alone. Combinations of gases and combinations of gaseous precursors may also be employed to confer and additional degree of stability.

These microspheres and foam made with gaseous precursors have several advantages. First, as the gases generated from temperature sensitive gaseous precursors tend to be insoluble and relatively non-diffusible, these gases can be stabilized more readily for use as topical or subcutaneous delivery vehicles. Because the gases are relatively stable, less stabilizing compound is necessary than would be required for more soluble and diffusible gases such as nitrogen or air. In general, a thicker walled less gas permeable or diffusable skin or membrane of stabilizing compound, i.e., a thick walled microsphere, is necessary to stabilize gases such as air or nitrogen. While thick walled microspheres filled with air, nitrogen or other gases can be used as topical or subcutaneous delivery vehicles for various active ingredients, the thick walls of such microspheres may limit the effectiveness of the microspheres and foam compositions. With the gaseous precursors used in the present invention, most notably the perfluorocarbon gaseous precursors, the stabilizing compounds can be less rigid and the resulting microspheres can be thinner walled and easier to apply, yet still possess sufficient stabilizing compound to stabilize the gas.

The present invention provides microspheres and foam, and a method of using those microspheres and foam for the topical or subcutaneous delivery to a selected tissue of a patient of any one or more of a variety of active ingredients. However, it is also contemplated that the microspheres and foam, per se, may themselves be capable of fulfilling the role of active ingredients, particularly in regard to cosmetic agents and their properties. Thus, for example, it may be possible to use a gas and gaseous precursor filled microspheres and foam by themselves for the purpose of conferring lubricity or humectant properties to a selected tissue, provided, of course, that the lipid composition is chosen with a view toward obtaining such properties in the final product. Selection of the stabilizing compound for such purposes is well within the skill of the artisan familiar with both the desired properties, and the variety of properties existent in stabilizing compounds available for making the gas and gaseous precursor filled microspheres of the present invention.

Gases and Gaseous Precursors Employed

The microspheres of the invention encapsulate a gas and/or gaseous precursor. The term "gas filled and/or gaseous precursor filled", as used herein, means that the microspheres to which the present invention is directed, have an interior volume that is comprised of at least about 10% gas and gaseous precursor, preferably at least about 25% gas and gaseous precursor, more preferably at least about 50% gas and gaseous precursor, even more preferably at least about 75% gas and gaseous precursor, and most preferably at least about 9% gas and gaseous precursor.

Any of the various biocompatible gases and gaseous precursors may be employed in the gas and gaseous precursor filled microspheres of the present invention. Such gases include, for example, air, nitrogen, carbon dioxide, oxygen, argon, fluorine, xenon, neon, helium, or any and all combinations thereof. Likewise, various fluorinated gaseous compounds, such as various perfluorocarbon, hydrofluorocarbon, and sulfur hexafluoride gases may be utilized in the preparation of the gas filled microspheres and microsphere based foam.

Notwithstanding the requirement that the gas and gaseous precursor filled microspheres be made from stabilizing compounds, it is preferred that a rather highly stable gas be utilized as well. By highly stable gas is meant a gas selected from those gases which will have low solubility and diffusability in aqueous media. Gases such as perfluorocarbons are less diffusible and relatively insoluble and as such are easier to stabilize into the form of bubbles in aqueous media.

The use of gaseous precursors is an optional embodiment of the present invention. In particular, perfluorocarbons have been found to be suitable for use as gaseous precursors. As the artisan will appreciate, a given perfluorocarbon may be used as a gaseous precursor, i.e., in the liquid state when the microspheres used in the present invention are first made, or may be used as a gas directly, i.e., in the gas state, to make the gas and gaseous precursor filled microspheres. Whether such a perfluorocarbon is a gas or liquid depends, of course, on its liquid/gas phase transition temperature, or boiling point. For example, one of the more preferred perfluorocarbons is perfluoropentane, which has a liquid/gas phase transition temperature or boiling point of 27° C., which means that it will be a liquid at ordinary room temperature, but will become a gas in the environment of the human body, where the temperature will be above its liquid/gas phase transition temperature or boiling point. Thus, under normal circumstance, perfluoropentane is a gaseous precursor. As further examples, there is perfluorobutane and perflurohexane, the next closest homologs of perfluoropentane. The liquid/gas phase transition temperature of perfluorobutane is 4° C. and that of perfluorohexane is 57° C., making the former potentially a gaseous precursor, but probably more useful as a gas, while the latter would have to be a gaseous precursor, but under unusual circumstances, because of its high boiling point.

Another aspect of the present invention is the use of a perfluorocarbon which will be in the liquid state at the temperature of use of the microspheres of the present invention, to assist or enhance the stability of said gas and gaseous precursor filled microspheres. Such perfluorocarbons useful as additional stabilizing agents include perfluorooctylbromide (PFOB), perfluorodecalin, perfluorododecalin, perfluorooctyliodide, perfluorotripropylamine, and perfluorotributylamine. In general, perfluorocarbons over six carbon atoms in length will not be gaseous, i.e., in the gas state, but rather will be liquids, i.e., in the liquid state, at normal human body temperature. These compounds may, however, additionally be utilized in preparing the stabilized gas and gaseous precursor filled microspheres used in the present invention. Preferably this perfluorocarbon is perfluorohexane, which is in the liquid state at room temperature. The gas which is present may be, e.g., air or nitrogen, or may be derived from a gaseous precursor, which may also be a perfluorocarbon, e.g., perfluoropentane. In that case, the microspheres of the present invention would be prepared from a mixture of perfluorocarbons, which for the examples given, would be perfluoropentane and perfluorohexane. It is theorized that the liquid perfluorocarbon is situated at the interface between the gas and the membrane surface of the microsphere. There is thus formed a stabilizing layer of perfluorocarbon on the surface of, e.g., a biocompatible lipid used to form the microsphere, and this perfluorocarbon layer also serves the purpose of preventing the gas from diffusing through the microsphere membrane. A gaseous precursor, within the context of the present invention, is a liquid at the temperature of manufacture and/or storage, but becomes a gas at least at or during the time of use.

Thus, it has been discovered that a liquid perfluorocarbon, when combined with a gas ordinarily used to make the microspheres of the present invention, may confer an added degree of stability not otherwise obtainable with the gas alone. Thus, it is within the scope of the present invention to utilize a perfluorocarbon gaseous precursor, e.g., perfluoropentane, together with a perfluorocarbon which remains liquid after administration to a patient, i.e., whose liquid to gas phase transition temperature is above the body temperature of the patient.

Any biocompatible gas or gaseous precursor may be used to form the stabilized gas and gaseous precursor filled microspheres. By "biocompatible" is meant a gas or gaseous precursor which, when introduced into the tissues of a human patient, will not result in any degree of unacceptable toxicity, including allergenic responses and disease states, and preferably are inert. Such a gas or gaseous precursor should also be suitable for making gas and gaseous precursor filled microspheres and foam useful as topical or subcutaneous delivery agents, as described herein. Preferred biocompatible gases are air, argon, helium, nitrogen, xenon and neon. The most preferred gas is air. Additionally, paramagnetic gases or gases such as $^{17}O$ may also be used.

The gas and gaseous precursor filled microspheres becomes stabilized when the stabilizing compounds described herein are employed; and the size of the microspheres can then be adjusted for the particular intended topical or subcutaneous application end use, although there is frequently no criticality in this regard. In any event, the size of the gas and gaseous precursor filled microspheres can be adjusted, if desired, by a variety of procedures including microemulsification, vortexing, extrusion, filtration, sonication, homogenization, repeated freezing and thawing cycles, extrusion under pressure through pores of defined size, and similar methods.

As noted above, the embodiments of the present invention may also include, with respect to their preparation, formation and use, gaseous precursors that can be activated by temperature. Further below is set out a table listing a series of gaseous precursors which undergo phase transitions from liquid to gaseous states at close to normal body temperature (37° C.) and the size of the emulsified droplets that would be required to form a microbubble of a maximum size of 10 microns.

TABLE 1

Physical Characteristics of Gaseous Precursors and Diameter of Emulsified Droplet to Form a 10 μm Microsphere*

| Compound | Molecular Weight | Boiling Point (°C.) | Density | Diameter (μm) of emulsified droplet to make 10 micron microsphere |
|---|---|---|---|---|
| perfluoro pentane | 288.04 | 27.73 | 1.7326 | 2.9 |
| 1-fluorobutane | 76.11 | 32.5 | 6.7789 | 1.2 |
| 2-methyl butane (isopentane) | 72.15 | 27.8 | 0.6201 | 2.6 |
| 2-methyl 1-butene | 70.13 | 31.2 | 0.6504 | 2.5 |
| 2-methyl-2-butene | 70.13 | 38.6 | 0.6623 | 2.5 |
| 1-butene-3-yne-2-methyl | 66.10 | 34.0 | 0.6801 | 2.4 |
| 3-methyl-1-butyne | 68.12 | 29.5 | 0.6660 | 2.5 |
| octafluoro cyclobutane | 200.04 | −5.8 | 1.48 | 2.8 |
| decafluoro butane | 238.04 | −2 | 1.517 | 3.0 |
| hexafluoro ethane | 138.01 | −78.1 | 1.607 | 2.7 |

*Source: Chemical Rubber Company Handbook of Chemistry and Physics Robert C. Weast and David R. Lide, eds. CRC Press, Inc. Boca Raton, Florida. (1989–1990).

There is also set out below a list composed of potential gaseous precursors that may be used to form microspheres of defined size. However, the list is not intended to be limiting, since it is possible to use other gaseous precursors for that purpose. In fact, for a variety of different applications, virtually any liquid can be used to make gaseous precursors so long as it is capable of undergoing a phase transition to the gas phase upon passing through the appropriate temperature. Suitable gaseous precursors for use in the present invention are the following: hexafluoro acetone, isopropyl acetylene, allene, tetrafluoro-allene, boron trifluoride, isobutane, 1,2-butadiene, 2,3-butadiene, 1,3-butadiene, 1,2,3-trichloro-2-fluoro -1,3-butadiene, 2-methyl-1,3-butadiene, hexafluoro-1,3-butadiene, butadiyne, 1-fluoro-butane, 2-methyl-butane, decafluorobutane, 1-butene, 2-butene, 2-methyl-1-butene, 3-methyl -1-butene, perfluoro-1-butene, perfluoro-2-butene, 4-phenyl-3-butene-2-one, 2-methyl-1-butene-3-yne, butyl nitrate, 1-butyne, 2-butyne, 2-chloro-1,1,1,4,4,4-hexafluorobutyne, 3-methyl-1-butyne, perfluoro-2-butyne, 2-bromobutyraldehyde, carbonyl sulfide, crotononitrile, cyclobutane, methyl-cyclobutane, octafluoro-cyclobutane, perfluorocyclobutene, 3-chlorocyclopentene, octafluorocyclopentene, cyclopropane, 1,2-dimethylcyclopropane, 1,1-dimethylcyclopropane, 1,2-dimethylcyclopropane, ethylcyclopropane, methylcyclopropane, diacetylene, 3-ethyl-3-methyl diaziridine, 1,1,1-trifluorodiazoethane, dimethyl amine, hexafluorodimethylamine, dimethylethylamine, bis(dimethylphosphine)amine, perfluorohexane, 2,3-dimethyl-2-norbornane, perfluorodimethylamine, dimethyloxonium chloride, 1,3-dioxolane-2-one, 4-methyl-1,1,1,2-tetrafluoroethane, 1,1,1-trifluoroethane, 1,1,2,2-tetrafluoroethane, 1,1,2-trichloro-1,2,2-trifluoroethane, 1,1-dichloroethane, 1,1-dichloro-1,2,2,2-tetrafluoroethane, 1,2-difluoroethane, 1-chloro-1,1,2,2,2-pentafluoroethane, 2-chloro-1,1-difluoroethane, 1,1-dichloro-2-fluoroethane, 1-chloro-1,1,2,2-tetrafluoroethane, 2-chloro-1,1-difluoroethane, chloroethane, chloropentafluoroethane, dichlorotrifluoroethane, fluoroethane, hexafluoroethane, nitropentafluoroethane, nitrosopentafluoroethane, perfluoroethylamine, ethyl vinyl ether, 1,1-dichloroethane, 1,1-dichloro-1,2-difluoroethane, 1,2-difluoroethane, methane, trifluoromethanesulfonylchloride, trifluoromethanesulfonylfluoride, bromodifluoronitrosomethane, bromofluoromethane, bromochlorofluoromethane, bromotrifluoromethane, chlorodifluoronitromethane, chlorodinitromethane, chlorofluoromethane, chlorotrifluoromethane, chlorodifluoromethane, dibromodifluoromethane, dichlorodifluoromethane, dichlorofluoromethane, difluoromethane, difluoroiodomethane, disilanomethane, fluoromethane, iodomethane, iodotrifluoromethane, nitrotrifluoromethane, nitrosotrifluoromethane, tetrafluoromethane, trichlorofluoromethane, trifluoromethane, 2-methylbutane, methyl ether, methyl isopropyl ether, methyllactate, methylnitrite, methylsulfide, methyl vinyl ether, neon, neopentane, nitrogen ($N_2$), nitrous oxide, 1,2,3-nonadecane-tricarboxylic acid-2-hydroxytrimethylester, 1-nonene-3-yne, oxygen ($O_2$), 1,4-pentadiene, n-pentane, perfluoropentane, 4-amino-4-methylpentan-2-one, 1-pentene, 2-pentene (cis), 2-pentene (trans), 3-bromopent-1-ene, perfluoropent-1-ene, tetrachlorophthalic acid, 2,3,6-trimethylpiperidine, propane, 1,1,1,2,2,3-hexafluoropropane, 1,2-epoxypropane, 2,2-difluoropropane, 2-aminopropane, 2-chloropropane, heptafluoro-1-nitropropane, heptafluoro-1-nitrosopropane, perfluoropropane, propene, hexafluoropropane, 1,1,1,2,3,3-hexafluoro-2,3 dichloropropane, 1-chloropropane, chloropropane-(trans), 2-chloropropane, 3-fluoropropane, propyne, 3,3,3-trifluoropropyne, 3-fluorostyrene, sulfur hexafluoride, sulfur (di)-decafluoride($S_2F_{10}$), 2,4-diaminotoluene, trifluoroacetonitrile, trifluoromethyl peroxide, trifluoromethyl sulfide, tungsten hexafluoride, vinyl acetylene, vinyl ether, and xenon.

The perfluorocarbons, as already indicated, are preferred compositions for use as the gaseous precursors as well as additional stabilizing components. Included in such perfluorocarbon compositions are saturated perfluorocarbons, unsaturated perfluorocarbons, and cyclic perfluorocarbons. The saturated perfluorocarbons, which are usually perferred, have the formula $C_nF_{2n+2}$, where n is from 1 to 12, preferably 2 to 10, more preferably 4 to 8, and most preferably 5. Examples of suitable saturated perfluorocarbons are the following: tetrafluoromethane, hexafluoroethane, octafluoropropane, decafluorobutane, dodecafluoropentane, perfluorohexane, and perfluoroheptane. Cyclic perfluorocarbons, which have the formula $C_nF_{2n}$, where n is from 3 to 8, preferably 3 to 6, may also be preferred, and include, e.g., hexafluorocyclopropane, octafluorocyclobutane, and decafluorocyclopentane.

It is part of the present invention to optimize the utility of the microspheres by using gases of limited solubility. By limited solubility, is meant the ability of the gas to diffuse out of the microspheres by virtue of its solubility in the surrounding aqueous medium. A greater solubility in the aqueous medium imposes a gradient with the gas in the microsphere such that the gas will have a tendency to diffuse out of said microsphere. A lesser solubility in the aqueous milieu, will, on the other hand, decrease or eliminate the gradient between the microsphere and the interface such that the diffusion of the gas out of the microsphere will be impeded. Preferably, the gas entrapped in the microsphere has a solubility less than that of oxygen, i.e., 1 part gas in 32 parts water. See *Matheson Gas Data Book*, 1966, Matheson Company Inc. More preferably, the gas entrapped in the microsphere possesses a solubility in water less than that of air; and even more preferably, the gas entrapped in the microsphere contains a gas that possesses a solubility in water less than that of nitrogen.

Stabilizing Compounds

One or more stabilizing compounds are employed to form the microspheres, and to assure continued encapsulation of the gases or gaseous precursors. Even for relatively insoluble, non-diffusible gases such as perfluoropropane or sulfur hexafluoride, improved microsphere preparations are obtained when one or more stabilizing compounds are utilized in the formation of the gas and gaseous precursor filled microspheres and any resultant foam, for use in the topical and subcutaneous delivery of various active agents. These compounds maintain the stability and the integrity of the microspheres with regard to their size, shape and/or other attributes, The terms "stable" or "stabilized", as used herein, means that the microspheres and/or foam formed thereby are substantially resistant to degradation, i.e., are resistant to the loss of microsphere structure or encapsulated gas or gaseous precursor for a useful period of time. Typically, the microspheres and/or foam of the invention have a good shelf life, often retaining at least about 90 percent by volume of its original foam structure for a period of at least about two or three weeks under normal ambient conditions, although it is preferred that this period be at least a month, more at least preferably two months, even more preferably at least six months, still more preferably eighteen months, and most preferably three years. Thus, the gas and gaseous precursor filled microspheres and foam typically have a good shelf life, sometimes even under adverse conditions, such as temperatures and pressures which are above or below those experienced under normal ambient conditions.

The stability of the microspheres and foam used in the present invention is attributable to at least in part to the materials from which said microspheres and foam are made, and it is often not necessary to employ additional stabilizing additives, although it is optional and often preferred to do so; and such additional stabilizing agents and their characteristics are explained in more detail herein. The materials from which the microspheres used in the present invention are constructed are preferably biocompatible lipid or polymer materials, and of these, the biocompatible lipids are especially preferred. In addition, because of the ease of formulation, i.e., the ability to produce the microspheres or foam just prior to administration, these microspheres and foam may be conveniently made on site.

The lipids and polymers employed in preparing the microspheres of the invention are biocompatible. By "biocompatible" is meant a lipid or polymer which, when introduced into the tissues of a human patient, will not result in any degree of unacceptable toxicity, including allergenic responses and disease states. Preferably the lipids or polymers are inert.

Biocompatible Lipids

For the biocompatible lipid materials, it is preferred that such lipid materials be what is often referred to as "amphiphilic" in nature (i.e., polar lipid), by which is meant any composition of matter which has, on the one hand, lipophilic, i.e., hydrophobic properties, while on the other hand, and at the same time, having hydrophilic properties.

Hydrophilic groups may be charged moieties or other groups having an affinity for water. Natural and synthetic phospholipids are examples of lipids useful in preparing the stabilized microspheres used in the present invention. They contain charged phosphate "head" groups which are hydrophilic, attached to long hydrocarbon tails, which are hydrophobic. This structure allows the phospholipids to achieve a single bilayer (unilamellar) arrangement in which all of the water-insoluble hydrocarbon tails are in contact with one another, leaving the highly charged phosphate head regions free to interact with a polar aqueous environment. It will be appreciated that a series of concentric bilayers are possible, i.e., oligolamellar and multilamellar, and such arrangements are also contemplated to be an aspect of the present invention. The ability to form such bilayer arrangements is one feature of the lipid materials useful in the present invention.

The lipid may alternatively be in the form of a monolayer, and the monolayer lipids may be used to form a single monolayer (unilamellar) arrangement. Alternatively, the monolayer lipid may be used to form a series of concentric monolayers, i.e., oligolamellar or multilamellar, and such arrangements are also considered to be within the scope of the invention.

It has also been found important to achieving the stabilized microspheres used in preparing the topical or subcutaneous delivery agents of the present invention that they be prepared at a temperature below the gel to liquid crystalline phase transition temperature of a lipid used as the stabilizing compound. This phase transition temperature is the temperature at which a lipid bilayer will convert from a gel state to a liquid crystalline state. See, for example, Chapman et al., *J. Biol. Chem.* 1974 249, 2512–2521.

It is believed that, generally, the higher the gel state to liquid crystalline state phase transition temperature, the more impermeable the gas and gaseous precursor filled microspheres are at any given temperature. See Derek Marsh, CRC *Handbook of Lipid Bilayers* (CRC Press, Boca Raton, Fla. 1990), at p. 139 for main chain melting transitions of saturated diacyl-sn-glycero-3-phosphocholines. The gel state to liquid crystalline state phase transition temperatures of various lipids will be readily apparent to those skilled in the art and are described, for example, in Gregoriadis, ed., *Liposome Technology*, Vol. I, 1–18 (CRC Press, 1984). The following table lists some of the representative lipids and their phase transition temperatures:

TABLE 2

Saturated Diacyl sn-Glycero (3) Phosphocholines:
Main Chain Phase Transition Temperatures*

| Carbons in Acyl Chains | Main Phase Transition Temperature °C. |
|---|---|
| 1,2-(12:0) | −1.0 |
| 1,2-(13:0) | 13.7 |
| 1,2-(14:0) | 23.5 |
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

*Derek Marsh "CRC Handbook of Lipid Bilayers" CRC Press, Boca Raton, Florida 1990 page 139.

It has been found possible to enhance the stability of the microspheres used in the present invention by incorporating at least a small amount, i.e., about 1 to about 10 mole percent of the total lipid, of a negatively charged lipid into the lipid from which the gas and gaseous precursor filled microspheres are to be formed. Suitable negatively charged lipids include, e.g., phosphatidylserine, phosphatidic acid, and fatty acids. Such negatively charged lipids provide added stability by counteracting the tendency of the microspheres to rupture by fusing together, i.e., the negatively charged lipids tend to establish a uniform negatively charged layer on the outer surface of the microsphere, which will be repulsed by a similarly charged outer layer on the other microspheres. In this way, the microspheres will tend to be prevented from coming into touching proximity with each other, which would often lead to a rupture of the membrane or skin of the respective microspheres and consolidation of the contacting microspheres into a single, larger microsphere. A continuation of this process of consolidation will, of course, lead to significant degradation of the microspheres and foam.

The lipid material or other stabilizing compound used to form the microspheres is also preferably flexible, by which is meant, in the context of gas and gaseous precursor filled microspheres, the ability of a structure to alter its shape, for example, in order to pass through an opening having a size smaller than the microsphere.

In selecting a lipid for preparing the stabilized microspheres used in the present invention, a wide variety of lipids will be found to be suitable for their construction. Particularly useful are any of the materials or combinations thereof known to those skilled in the art as suitable for liposome preparation. The lipids used may be of either natural, synthetic or semi-synthetic origin.

Lipids which may be used to prepare the gas and gaseous precursor filled microspheres used in the present invention include but are not limited to: lipids such as fatty acids, lysolipids, phosphatidylcholine with both saturated and unsaturated lipids including dioleoylphosphatidylcholine; dimyristoylphosphatidylcholine; dipentadecanoylphosphatidylcholine; dilauroylphosphatidylcholine; dipalmitoylphosphatidylcholine (DPPC); distearoylphosphatidylcholine (DSPC); phosphatidylethanolamines such as dioleoylphosphatidylethanolamine and dipalmitoylphosphatidylethanolamine (DPPE); phosphatidylserine; phosphatidylglycerol; phosphatidylinositol; sphingolipids such as sphingomyelin; glycolipids such as ganglioside GM1 and GM2; glucolipids; sulfatides; glycosphingolipids; phosphatidic acids such as dipalymitoylphosphatidic acid (DPPA); palmitic acid; stearic acid; arachidonic acid; oleic acid; lipids bearing polymers such as polyethyleneglycol, i.e., PEGylated lipids, chitin, hyaluronic acid or polyvinylpyrolidone; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of 6–8 carbons in length; synthetic phospholipids with asymmetric acyl chains (e.g., with one acyl chain of 6 carbons and another acyl chain of 12 carbons); ceramides; non-ionic liposomes including niosomes such as polyoxyethylene fatty acid esters, polyoxyethylene fatty alcohols, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oil, polyoxyethylene-polyoxypropylene polymers, and polyoxyethylene fatty acid stearates; sterol aliphatic acid esters including cholesterol sulfate, cholesterol butyrate, cholesterol iso-butyrate, cholesterol palmitate, cholesterol stearate, lanosterol acetate, ergosterol palmitate, and phytosterol n-butyrate; sterol esters of sugar acids including cholesterol glucuroneide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid, accharic acid, and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; longchain alcohols including n-decyl alcohol, lauryl alcohol, myristyl alcohol, cetyl alcohol, and n-octadecyl alcohol; 6-(5-cholesten-3β-yloxy)-1 -thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylaminocoumarin-3-yl)carbonyl)methylamino)-octadecanoic acid; N-[12-(((7'-diethylaminocoumarin-3-yl)carbonyl)methyl-amino) octadecanoyl]-2-aminopalmitic acid; cholesteryl)4'-trimethylammonio)butanoate; N-succinyldioleoylphosphatidylethanolamine; 1,2-dioleoyl-sn-glycerol;1,2-dipalmitoyl-sn-3-succinylglycerol; 1,3-dipalmitoyl-2-succinylglycerol;1-hexadecyl-2-palmitoyl-glycerophosphoethanolamine and palmitoylhomocysteine, and/or combinations thereof.

If desired, a variety of cationic lipids such as DOTMA, N-[1-(2,3-dioleoyloxy)propyl]-N,N,N-trimethylammoium chloride; DOTAP, 1,2-dioleoyloxy-3-(trimethylammonio)propane; and DOTB, 1,2-dioleoyl-3-(4'-trimethyl-ammonio) butanoyl-sn-glycerol may be used. In general the molar ratio of cationic lipid to non-cationic lipid in the liposome may be, for example, 1:1000, 1:100, preferably, between 2:1 to 1:10, more preferably in the range between 1:1 to 1:2.5 and most preferably 1:1 (ratio of mole amount cationic lipid to mole amount non-cationic lipid, e.g., DPPC). A wide variety of lipids may comprise the non-cationic lipid when cationic lipid is used to construct the microsphere. Preferably, this non-cationic lipid is dipalmitoylphosphatidylcholine, dipalmitoylphosphatidylethanolamine or dioleoylphosphatidylethanolamine. In lieu of cationic lipids as described above, lipids bearing cationic polymers such as polylysine or polyarginine, as well as alkyl phosphonates, alkyl phosphinates, and alkyl phosphites, may also be used to construct the microspheres.

The most preferred lipids are phospholipids, preferably DPPC, DPPE, DPPA and DSPC, and most preferably DPPC.

In addition, examples of saturated and unsaturated fatty acids that may be used to prepare the stabilized microspheres used in the present invention, in the form of gas and gaseous precursor filled mixed micelles, may include molecules that may contain preferably between 12 carbon atoms and 22 carbon atoms in either linear or branched form. Hydrocarbon groups consisting of isoprenoid units and/or prenyl groups can be used as well. Examples of saturated fatty acids that are suitable include, but are not limited to, lauric, myristic, palmitic, and stearic acids; examples of unsaturated fatty acids that may be used are, but are not limited to, lauroleic, physeteric, myristoleic, palmitoleic, petroselinic, and oleic acids; examples of branched fatty acids that may be used are, but are not limited to, isolauric, isomyristic, isopalmitic, and isostearic acids. In addition, to the saturated and unsaturated groups, gas and gaseous precursor filled mixed micelles can also be composed of 5 carbon isoprenoid and prenyl groups.

Biocompatible Polymers

The biocompatible polymers useful as stabilizing compounds for preparing the gas and gaseous precursor filled microspheres used in the present invention can be of either natural, semi-synthetic or synthetic origin. As used herein, the term polymer denotes a compound comprised of two or more repeating monomeric units, and preferably 10 or more repeating monomeric units. The term semi-synthetic polymer, as employed herein, denotes a natural polymer that has been chemically modified in some fashion. Exemplary natural polymers suitable for use in the present invention include naturally occurring polysaccharides. Such polysaccharides include, for example, arabinans, fructans, fucans, galactans, galacturonans, glucans, mannans, xylans (such as, for example, inulin), levan, fucoidan, carrageenan, galatocarolose, pectic acid, pectin, amylose, pullulan, glycogen, amylopectin, cellulose, dextran, pustulan, chitin, agarose, keratan, chondroitan, dermatan, hyaluronic acid, alginic acid, xanthan gum, starch and various other natural homopolymer or heteropolymers such as those containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Exemplary semi-synthetic polymers include carboxymethylcellulose, hydroxymethylcellulose, hydroxypropylmethylcellulose, methylcellulose, and methoxycellulose. Exemplary synthetic polymers suitable for use in the present invention include polyethylenes (such as, for example, polyethylene glycol, polyoxyethylene, and polyethylene terephthlate), polypropylenes (such as, for example, polypropylene glycol), polyurethanes (such as, for example, polyvinyl alcohol (PVA), polyvinylchloride and polyvinylpyrrolidone), polyamides including nylon, polystyrene, polylactic acids, fluorinated hydrocarbons, fluorinated carbons (such as, for example, polytetrafluoroethylene), and polymethylmethacrylate, and derivatives thereof. Methods for the preparation of such polymer-based microspheres will be readily apparent to those skilled in the art, once armed with the present disclosure, when the present disclosure is coupled with information known in the art, such as that described and referred to in Unger, U.S. Pat. No. 5,205,290, the disclosures of which are hereby incorporated herein by reference, in their entirety.

Other and Auxiliary Stabilizing Compounds

It is also contemplated to be a part of the present invention to prepare stabilized gas and gaseous precursor filled microspheres and foam using compositions of matter in addition to the biocompatible lipids and polymers described above, provided that the microspheres so prepared meet the stability and other criteria set forth herein. These compositions may be basic and fundamental, i.e., form the primary basis for creating or establishing the stabilized gas and gaseous precursor filled microspheres. On the other hand, they may be auxiliary, i.e., act as subsidiary or supplementary agents which either enhance the functioning of the basic stabilizing compound or compounds, or else contribute some desired property in addition to that afforded by the basic stabilizing compound.

However, it is not always possible to determine whether a given compound is a basic or an auxiliary agent, since the functioning of the compound in question is determined empirically, i.e., by the results produced with respect to producing stabilized microspheres. As examples of how these basic and auxiliary compounds may function, it has been observed that the simple combination of a biocompatible lipid and water or saline when shaken will often give a cloudy solution subsequent to autoclaving for sterilization. Such a cloudy solution may function as a topical or subcutaneous delivery agent, but is aesthetically objectionable and may imply instability in the form of undissolved or undispersed lipid particles. Thus, propylene glycol may be added to remove this cloudiness by facilitating dispersion or dissolution of the lipid particles. The propylene glycol may also function as a thickening agent which improves microsphere formation and stabilization by increasing the surface tension on the microsphere membrane or skin. It is possible that the propylene glycol further functions as an additional layer that coats the membrane or skin of the microsphere, thus providing additional stabilization.

As examples of such further basic or auxiliary stabilizing compounds, there are conventional surfactants which may be used; see D'Arrigo U.S. Pat. Nos. 4,684,479 and 5,215,680.

Additional auxiliary and basic stabilizing compounds include such agents as peanut oil, canola oil, olive oil, safflower oil, corn oil, or any other oil commonly known to be ingestible which is suitable for use as a stabilizing compound in accordance with the requirements and instructions set forth in the instant specification.

In addition, compounds used to make mixed micelle systems may be suitable for use as basic or auxiliary stabilizing compounds, and these include, but are not limited to: lauryltrimethylammonium bromide (dodecyl-), cetyltrimethylammonium bromide (hexadecyl-), myristyltrimethylammonium bromide (tetradecyl-), alkyldimethylbenzylammonium chloride (alkyl=$C_{12}, C_{14}, C_{16}$), benzyldimethyldodecylammonium bromide/chloride, benzyldimethyl hexadecylammonium bromide/chloride, benzyldimethyl tetradecylammonium bromide/chloride, cetyldimethylethylammonium bromide/chloride, or cetylpyridinium bromide/chloride.

It has been found that the gas and gaseous precursor filled microspheres and foam used in the present invention may be controlled according to size, solubility and heat stability by choosing from among the various additional or auxiliary stabilizing agents described herein. These agents can affect these parameters of the microspheres not only by their physical interaction with the lipid coatings, but also by their ability to modify the viscosity and surface tension of the surface of the gas and gaseous precursor filled microsphere. Accordingly, the gas and gaseous precursor filled microspheres used in the present invention may be favorably modified and further stabilized, for example, by the addition of one or more of a wide variety of (a) viscosity modifiers, including, but not limited to carbohydrates and their phosphorylated and sulfonated derivatives; and polyethers, preferably with molecular weight ranges between 400 and 100,000; di- and trihydroxy alkanes and their polymers, preferably with molecular weight ranges between 200 and 50,000; (b) emulsifying and/or solubilizing agents may also be used in conjunction with the lipids to achieve desired modifications and further stabilization; such agents include, but are not limited to, acacia, cholesterol, diethanolamine, glyceryl monostearate, lanolin alcohols, lecithin, mono- and di-glycerides, mono-ethanolamine, oleic acid, oleyl alcohol, poloxamer (e.g., poloxamer 188, poloxamer 184, and poloxamer 181), polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax; (c) suspending and/or viscosity-increasing agents that may be used with the lipids include, but are not limited to, acacia, agar, alginic acid, aluminum mono-stearate, bentonite, magma, carbomer 934P, carboxymethylcellulose, calcium and sodium and sodium 12, carrageenan, cellulose, dextran, gelatin, guar gum, locust bean gum, veegum, hydroxyethyl cellulose, hydroxypropyl methylcellulose, magnesium-aluminum-silicate, methylcellulose, pectin, polyethylene oxide, povidone, propylene glycol alginate, silicon dioxide, sodium alginate, tragacanth, xanthum gum, α-d-gluconolactone, glycerol and mannitol; (d) synthetic suspending agents may also be utilized such as polyethyleneglycol (PEG), polyvinylpyrrolidone (PVP), polyvinylalcohol (PVA), polypropylene glycol, and polysorbate; and (e) tonicity raising agents may be included; such agents include but are not limited to sorbitol, propyleneglycol and glycerol.

Preferred embodiments of the present invention include microspheres and foams wherein the stabilizing compound from which the stabilized gas and gaseous precursor filled microspheres are formed comprises three components: (1) a neutral (e.g., nonionic or zwitterionic) lipid, (2) a negatively charged lipid, and (3) a lipid bearing a hydrophilic polymer. Preferably, the amount of said negatively charged lipid will be greater than 1 mole percent of total lipid present, and the amount of lipid bearing a hydrophilic polymer will be greater than 1 mole percent of total lipid present. It is also preferred that said negatively charged lipid be a phosphatidic acid. The lipid bearing a hydrophilic polymer will desirably be covalently bound to said polymer, and said polymer will preferably have a weight average molecular weight of from about 400 to about 100,000. Said hydrophilic polymer is preferably selected from the group consisting of polyethyleneglycol, polypropyleneglycol, polyvinylalcohol, and polyvinylpyrrolidone and copolymers thereof. Where the hydrophilic polymer is polyethyleneglycol, a lipid bearing such a polymer will be said to be "PEGylated", which has reference to the abbreviation for polyethyleneglycol: "PEG". Said lipid bearing a hydrophilic polymer is preferably dipalmitoylphosphatidylethanolamine-polyethyleneglycol 5000, i.e., a polyethyleneglycol having a mean weight average molecular weight of about 5000; or distearoyl-phosphatidylethanolamine-polyethyleneglycol 5000.

Preferred embodiments of the microsphere and foam based topical and subcutaneous delivery agents contemplated by the present invention would include, e.g., 77.5 mole percent dipalmitoylphophatidylcholine (DPPC), with 12.5 mole percent of dipalmitoylphosphatidic acid (DPPA), and with 10 mole percent of dipalmitoylphosphatidylethanolamine-polyethyleneglycol-5000 (DPPE/PEG5000), i.e., a polyethyleneglycol having a mean weight average molecular weight of about 5000. These compositions in a 82/10/8 ratio of mole percentages, respectively, is also preferred. The DPPC component is effectively neutral, since the phosphtidyl portion is negatively charged and the choline portion is positively charged. Consequently, the DPPA component, which is negatively charged, is added to enhance stabilization in accordance with the mechanism described further above regarding negatively charged lipids as an additional agent. The third component, DPPE/PEG, provides a PEGylated material bound to the lipid membrane or skin of the microsphere by the DPPE moiety, with the PEG moiety free to surround the microsphere membrane or skin, and thereby form a physical barrier to various enzymatic and other endogenous agents in the body whose function is to degrade such foreign materials. It is also theorized that the PEGylated material, because of its structural similarity to water, is able to defeat the action of the macrophages of the human immune system, which would otherwise tend to surround and remove the foreign object. The result is an increase in the time during which the stabilized microspheres can function as foam based topical and subcutaneous delivery agents.

Aqueous Diluents

As already mentioned above, where the microspheres are lipid in nature, particularly a bilayer, an essential component of the stabilized microspheres is an aqueous environment of some kind, which induces the lipid, because of its hydrophobic/hydrophilic nature, to form microspheres, the most stable configuration which it can achieve in such an environment. The diluents which can be employed to create such an aqueous environment include, but are not limited to water, either deionized or containing any number of dissolved salts which will not interfere with creation and maintenance of the stabilized microspheres or their use as topical and subcutaneous delivery agents; and normal saline and physiological saline.

Active Ingredients

The present invention provides gas or gaseous precursor filled microspheres and a method of using those microspheres for the topical or subcutaneous delivery to a selected tissue of a patient of any one or more of a variety of active ingredients. The general term "active ingredient" has been used herein for the purpose of including a number of functionally different categories of materials that might be employed. By the term "active ingredient", as used herein, it is meant a compound or composition that is intended to provide a therapeutic or cosmetic benefit. For example, in addition to a variety of therapeutic agents (e.g., drugs) which might be used, there are a number of treatment agents that may be considered to be cosmetics that can be topically or subcutaneously applied using the microspheres or foam of the present invention. These include, without any intended limitation of the present invention, various vitamins and other agents having skin restorative and anti-wrinkling properties, sunblocking agents, and insect repellants. The effective amount of an active ingredient to be employed in the compositions of the invention will vary, as one skilled in the art will recognize, based upon such factors as the age, size, and type of patient to which the compositions of the invention are to be administered, the manner in which administration is to be effected (topically, subcutaneously; with/without a depot), the particular therapeutic, cosmetic or other application intended, and the desired therapeutic, cosmetic or other effect sought. Once armed with the foregoing information, one skilled in the art will be readily able to determine the effective amount of active agent to be employed.

The microspheres may also be designed so that there is a distribution of the active ingredient inside and/or outside of the microsphere. The distribution may be both inside and outside, and may be symmetric or asymmetric.

The particular chemical structure of the active ingredient may be selected or modified to achieve the desired solubility, such that the active ingredient may either be encapsulated within the internal gas and gaseous precursor filled space of the microsphere, attached to the outside of the microsphere (covalently or otherwise), enmeshed in the microsphere wall, or simply associated with (that is, not encapsulated in or attached to) the microsphere. For example, the surface-bound active ingredient may bear one or more acyl chains such that, when the microsphere is burst by the topical application, heated, or ruptured via cavitation produced by the application of ultrasound, microwave, light, or magnetic induction energy, as described in detail further below, the acylated active ingredient may then leave the surface and/or the active ingredient may be cleaved from, e.g., the acyl chains of the chemical group to which it is bound. Similarly, other active ingredients may be formulated with a hydrophobic group which is, e.g., aromatic or sterol in structure, to incorporate them into the surface skin or membrane of the microsphere.

Cosmetic Agents

The various types of cosmetic formulations to which the gas and gaseous precursor filled microspheres of the present invention are applicable, and to which they may be advantageously adapted, include, among others, cosmetic creams, ointments, lotions, skin softeners, gels, blush, eye-liners, mascaras, acne-medications, cold creams, cleansing creams, and oleaginous foams. Cosmetic agents which may be incorporated into the microspheres and foam of the present invention include but are not limited to: Vitamin A, Vitamin C, Vitamin D, Vitamin E, Vitamin K, Beta Carotene, collagen, elastin, retinoic acid, retinol palmitate, aloe vera, lanolin, hyaluronic acid, and nucleosides.

The gas and gaseous precursor filled microspheres are quite useful for delivering sunscreen agents to a selected tissue. Such sunscreen agents include but are not limited to: 4% benzyl salicylate and benzyl cinnamate (2% each); 5% cycloform (isobutyl-p-aminobenzoate); 5% diallyl trioleate; 2.5% monoglyceryl p-aminobenzoate; 4% propylene glycol p-aminobenzoate; and other photoabsorptive compounds.

Therapeutic Agents

Among the therapeutic agents which may be applied topically or subcutaneously to a selected tissue of a patient using the microspheres of the present invention are antifungal agents such as ketoconazole, nystatin, griseofulvin, flucytosine (5-fc), miconazole, and amphotericin B; hormones such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide and fludrocortisone acetate; vitamins such as cyanocobalamin neinoic acid, retinoids and derivatives such as retinol palmitate, and α-tocopherol; peptides, such as manganese super oxide dismutase; enzymes such as alkaline phosphatase; antiallergic agents such as amelexanox; anti-coagulation agents such as phenprocoumon and heparin; anti-tuberculars such as para-aminosalicylic acid, isoniazid, capreomycin sulfate cycloserine, ethambutol hydrochloride ethionamide, pyrazinamide, rifampin, and streptomycin sulfate; antivirals such as acyclovir, amantadine, azidothymidine (AZT or Zidovudine), ribavirin and vidarabine monohydrate (adenine arabinoside, ara-A); antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin rifampin and tetracycline; antiinflammatories such as diflunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; growth factors such as Epidermal Growth Factor(EGF), acidic Fibroblast Growth Factor (aFGF), Basic Fibroblast Growth Factor (bFGF), Insulin-Like Growth Factors (IGF) types I and II, Nerve Growth Factor (NGF), Platelet-Derived Growth Factor (PDGF), Stem Cell Factor (SCF) and Transforming Growth Factor (TGF) of either the α or β families; cardiovascular agents such as clonidine, propranolol, lidocaine, nicardipine and nitroglycerin; diuretics such as mannitol and urea; and radioactive particles or ions such as strontium, iodine, rhenium and yttrium; along with many others such as scopolamine, nicotine, methylnicotinate, mechlorisone dibutyrate, naloxone, methanol, caffeine, salicylic acid and 4-cyanophenol.

These microspheres, in addition, are particularly suitable for delivery of peptides to a selected tissue. As examples not meant to limit the scope of the present invention, the following peptides may be incorporated into the microspheres and foam for the purposes of topical or subcutaneous application and delivery: melanin concentrating hormone, melanin stimulating hormone, trypsin inhibitor, Bowman Burk inhibitor, luteinizing hormone releasing hormone (LHRH), bombesin, cholecystokinin, insulin, gastrin, endorphins, enkephalins, growth hormone, prolactin, oxytocin, follicle stimulating hormone (FSH), human chorionic gonadotropin, corticotropin, β and lipotropin, calcitonin, glucagon, thyrotropin, elastin, cyclosporin, and collagen. In addition, all of the available antagonists to the abovementioned peptides may be used as well. Further, factors such as hyaluronic acid, heparin, and heparin sulfate may be utilized.

In certain preferred embodiments, the therapeutic agent is a monoclonal antibody, such as a monoclonal antibody capable of binding to melanoma antigen. Such monoclonal antibodies may also be used in targeting other therapeutic agents to which they are bound to form an adduct or composite. The very precise recognition attributes of the monoclonal antibody are used to advantage to carry the therapeutic agent to which it is attached, to the specific site in which the therapeutic agent will function. Such targeting is of great value, e.g., in the chemotherapy of malignant tumors where the toxicity of the chemotherapeutic agent prevents its systemic use in high concentrations.

Other preferred therapeutics include genetic material such as nucleic acids, RNA, and DNA, of either natural or synthetic origin, including recombinant RNA and DNA and antisense RNA and DNA. Types of genetic material that may be used include, for example, genes carried on expression vectors such as plasmids, phagemids, cosmids, yeast artificial chromosomes (YACs), and defective or helper viruses, antigene nucleic acids, both single and double stranded RNA and DNA and analogs thereof, such as phosphorothioate, phosphoroamidate, and phosphorodithioate oligodeoxynucleotides. Additionally, the genetic material may be combined, for example, with proteins or other polymers.

Examples of genetic therapeutics that may be applied using the microspheres and foam of the present invention include DNA encoding at least a portion of an HLA gene, DNA encoding at least a portion of dystrophin, DNA encoding at least a portion of CFTR, DNA encoding at least a portion of IL-2, DNA encoding at least a portion of TNF, an antisense oligonucleotide capable of binding the DNA encoding at least a portion of Ras.

DNA encoding certain proteins may be used in the treatment of many different types of diseases. For example, adenosine deaminase may be provided to treat ADA deficiency; tumor necrosis factor and/or interleukin-2 may be provided to treat advanced cancers; HDL receptor may be provided to treat liver disease; thymidine kinase may be provided to treat ovarian cancer, brain tumors, or HIV infection; HLA-B7 may be provided to treat malignant melanoma; interleukin-2 may be provided to treat neuroblastoma, malignant melanoma, or kidney cancer; interleukin-4 may be provided to treat cancer; HIV env may be provided to treat HIV infection; antisense ras/p53 may be provided to treat lung cancer; and Factor VIII may be provided to treat Hemophilia B. See, for example, Thompson, L., Science, 1992, 258, 744–746.

Anti-sense peptides and anti-sense oligonucleotides may be used for the purposes of topical or subcutaneous application and delivery to a selected tissue. As an example, the anti-sense sequence to basic fibroblast growth factor (bFGF) for the treatment of cheloids in a selected tissue may be used. Antisense peptides which de-activate, i.e., turn-off the cascade response of endogenous cytokines involved in inflammation is another example of a topical or subcutaneous drug delivery within the scope of the present invention. Other applications for topically and subcutaneously applied gas and gaseous precursor filled microspheres and foam include, e.g., that of the gene encoding melanocyte stimulating hormone activity for the management of skin disorders involving hypopigmentation, e.g., vitiligo or albinism. Alternatively, topical or subcutaneous application of the gene encoding melanin concentrating hormone activity could be used for the treatment of diseases involving hyperpigmentation, e.g., in "Cafe Aulait" spots, or for the removal of hyperpigmented areas from a selected tissue, e.g., "moles" or "beauty spots".

Further, peptide analogs with either membrane spanning capabilities, or pore-forming peptides such as cyclosporin and neomycin, may be incorporated into the gas and gaseous precursor filled microspheres for topical or subcutaneous application as both antibiotic ointments and immunosuppressants. As well, peptides with N-terminal aliphatic or cyclic acyl chains may be used to enhance delivery of other peptides or active ingredients. In addition, side chain acylated analogs or N-Methyl amino acid analogs may also be incorporated into these peptides in order to make them more lipophilic and thereby facilitate drug delivery.

Still other applications for topically or subcutaneously applied gas and gaseous precursor filled microspheres include topical or subcutaneous delivery of chelants and chelating agents in order to treat various diseases susceptible to treatment with chelants, e.g., psoriasis and psoriatic lesions, and Wilsons's disease. Suitable chelants and chelating agents include, but are not limited to: penicillamine; citrate; ascorbate; diethylenetriaminepentaacetic acid (DTPA), and derivatives and salts thereof; dihydroxypropylethylenediamine (DPEA), and derivatives and salts thereof; cyclohexanediaminetetraacetic acid (CHTA), and derivatives and salts thereof; ethylenediaminetetraacetic acid (EDTA), and derivatives and salts thereof; ethylene glycolbis(β-aminoethyl ether)N,N,N',N',-tetraacetic acid (EGTA), and derivatives and salts thereof; etidronic acid (EHDP), and derivatives and salts thereof; dimethylsulfoxide (DMSO), and derivatives and salts thereof; dipyridoxylethylenediaminediacetate-bisphosphate (DPDP), and derivatives and salts thereof; N,N'-(1,2-ethanedivinylbis(oxy-2,1-phenylene))bis(N-(carboxymethyl) (BAPTA), and derivatives and salts thereof; aminophenol-triacetic acid (APTRA), and derivatives and salts thereof; tetrakis(2-pyridylmethyl)ethylenediamine (TPEN), and derivatives and salts thereof; 1,4,7,10-tetraazacyclodecane (DOTA) and derivatives and salts thereof; and cyanins and their derivatives.

Furthermore, immunosuppressants or anti-inflammatory preparations can be incorporated into the gas and gaseous precursor filled microspheres of the present invention and used topically or subcutaneously in the vicinity of bone joints, to manage pain and inflammation and other symptoms due to any of a number of inflammatory and autoimmune diseases, e.g., arthritic conditions such as rheumatoid arthritis or degenerative joint disease.

If desired, more than one therapeutic may be applied using the microspheres or foam of the present invention. For example, a single microsphere may contain more than one therapeutic, or microspheres containing different therapeutics may be co-administered. By way of example, a monoclonal antibody capable of binding to melanoma antigen and an oligonucleotide encoding at least a portion of IL-2 may be administered at the same time. The phrase "at least a portion of," as used herein, means that the entire gene need not be represented by the oligonucleotide, so long as the portion of the gene represented provides an effective block to gene expression.

Prodrugs

Similarly, prodrugs may be encapsulated in the microspheres, and are included within the ambit of the term therapeutic agent, as used herein. Prodrugs are well known in the art and include inactive drug precursors which, when exposed to high temperature or different pH, metabolizing enzymes, cavitation and/or pressure, in the presence of oxygen or otherwise, or when released from the microspheres, will form active drugs. Such prodrugs can be activated from, or released from, gas-filled microspheres in the method of the present invention, upon the application of ultrasound or radiofrequency microwave energy to the prodrug-containing microspheres with the resultant cavitation, heating, pressure, and/or release from the microspheres. Suitable prodrugs will be apparent to those skilled in the art, and are described, for example, in Sinkula et al., *J. Pharm. Sci.* 1975, 64, 181–210, the disclosure of which is hereby incorporated herein by reference in its entirety.

Prodrugs, for example, may comprise inactive forms of the active therapeutic agents wherein a chemical group is present on the prodrug which renders it inactive and/or confers solubility or some other property to the drug. In this form, the prodrugs are generally inactive, but once the chemical group has been cleaved from the prodrug, by heat, pH change, cavitation, pressure, and/or by enzymes in the surrounding environment or otherwise, the active drug is generated. Such prodrugs are well described in the art, and comprise a wide variety of drugs bound to chemical groups through bonds such as esters to short, medium or long chain aliphatic carbonates, hemiesters of organic phosphate, pyrophosphate, sulfate, amides, amino acids, azo bonds, carbamate, phosphamide, glucosiduronate, N-acetylglucosamine and β-glucoside.

Examples of therapeutic agents with the parent molecule and the reversible modification or linkage are as follows: convallatoxin with ketals, hydantoin with alkyl esters, chlorphenesin with glycine or alanine esters, acetaminophen with caffeine complex, acetylsalicylic acid with THAM salt, acetylsalicylic acid with acetamidophenyl ester, naloxone with sulfate ester, 15-methylprostaglandin $F_{2\alpha}$ with methyl ester, procaine with polyethylene glycol, erythromycin with alkyl esters, clindamycin with alkyl esters or phosphate esters, tetracycline with betaine salts, 7-acylaminocephalosporins with ring-substituted acyloxybenzyl esters, nandrolone with phenylproprionate decanoate esters, estradiol with enol ether acetal, methylprednisolone with acetate esters, testosterone with n-acetylglucosaminide glucosiduronate(trimethylsilyl)ether, cortisol or prednisolone or dexamethasone with 21-phosphate esters.

Prodrugs may also be designed as reversible drug derivatives and utilized as modifiers to enhance drug transport to site-specific tissues. Examples of parent molecules with reversible modifications or linkages to influence transport to a site specific tissue and for enhanced therapeutic effect include isocyanate with haloalkyl nitrosurea, testosterone with propionate ester, methotrexate (3-5'-dichloromethotrexate) with dialkyl esters, cytosine arabinoside with 5'-acylate, nitrogen mustard (2,2'-dichloro-N-methyldiethylamine), nitrogen mustard with aminomethyl tetracycline, nitrogen mustard with cholesterol or estradiol or dehydroepiandrosterone esters and nitrogen mustard with azobenzene.

As one skilled in the art would recognize, a particular chemical group to modify a given therapeutic agent may be selected to influence the partitioning of the therapeutic agent into either the outer skin or membrane of the microsphere, or the internal space or cavity of the microsphere. The bond selected to link the chemical group to the therapeutic agent may be selected to have the desired rate of metabolism, e.g., hydrolysis in the case of ester bonds in the presence of serum esterases after release from the gas and gaseous precursor filled microspheres. Additionally, the particular chemical group may be selected to influence the biodistribution of the therapeutic agent employed in the gas and gaseous precursor filled, therapeutic agent carrying, microsphere of the present invention, e.g., N,N-bis(2-chloroethyl)-phosphorodiamidic acid with cyclic phosphoramide for ovarian adenocarcinoma.

Additionally, the prodrugs employed within the gas and gaseous precursor filled microspheres may be designed to contain reversible derivatives which are utilized as modifiers of duration of activity to provide prolonged or depot action effects. For example, nicotinic acid may be modified with dextran and carboxymethlydextran esters, streptomycin with alginic acid salt, dihydrostreptomycin with pamoate salt, cytarabine (ara-C) with 5'-adamantoate ester, ara-adenosine (ara-A) with 5'-palmitate and 5'-benzoate esters, amphotericin B with methyl esters, testosterone with 17-β-alkyl esters, estradiol with formate ester, prostaglandin with 2-(4-imidazolyl)ethylamine salt, dopamine with amino acid amides, chloramphenicol with mono- and bis(trimethylsilyl) ethers, and cycloguanil with pamoate salt. In this form, a depot or reservoir of long-acting drug may be released in vivo from the gas and gaseous precursor filled prodrug bearing microspheres.

Additionally, the prodrugs employed within the gas and gaseous precursor filled microspheres may be designed to contain reversible derivatives which are utilized as modifiers of duration of activity to provide, prolong or depot action effects. For example, nicotinic acid may be modified with dextran and carboxymethlydextran esters, streptomycin with alginic acid salt, dihydrostreptomycin with pamoate salt, cytarabine (ara-C) with 5'-adamantoate ester, ara-adenosine (ara-A) with 5-palmitate and 5'-benzoate esters, amphotericin B with methyl esters, testosterone with 17-β-alkyl esters, estradiol with formate ester, prostaglandin with 2-(4-imidazolyl)ethylamine salt, dopamine with amino acid amides, chloramphenicol with mono- and bis(trimethylsilyl) ethers, and cycloguanil with pamoate salt. In this form, a depot or reservoir of long-acting drug may be released in vivo from the gas and gaseous precursor filled prodrug bearing microspheres.

In addition, compounds which are generally thermally labile may be utilized to create toxic free radical compounds useful, e.g., in chemotherapy. Compounds with azolinkages, peroxides and disulfide linkages which decompose with high temperature are preferred. With this form of prodrug, azo, peroxide or disulfide bond containing compounds are activated by cavitation and/or increased heating caused by the interaction of high energy sound with the gas and gaseous precursor filled microspheres to create cascades of free radicals from these prodrugs entrapped therein. A wide variety of drugs or chemicals may constitute these prodrugs, such as azo compounds, the general structure of such compounds being R—N=N—R, wherein R is a hydrocarbon chain, where the double bond between the two nitrogen atoms may react to create free radical products in vivo.

Exemplary drugs or compounds which may be used to create free radical products include azo containing compounds such as azobenzene, 2,2'-azobisisobutyronitrile, azodicarbonamide, azolitmin, azomycin, azosemide, azosulfamide, azoxybenzene, aztreonam, sudan III, sulfachrysoidine, sulfamidochrysoidine and sulfasalazine, compounds containing disulfide bonds such as sulbentine, thiamine disulfide, thiolutin, thiram, compounds containing peroxides such as hydrogen peroxide and benzoylperoxide, 2,2'-azobisisobutyronitrile, 2,2'-azobis(2-amidopropane) dihydrochloride, and 2,2'-azobis(2,4-dimethylvaleronitrile).

A gas and gaseous precursor filled microsphere filled with oxygen gas should create extensive free radicals with cavitation. Also, metal ions from the transition series, especially manganese, iron and copper, can increase the rate of formation of reactive oxygen intermediates from oxygen. By encapsulating metal ions within the microspheres, the formation of free radicals in vivo can be increased. These metal ions may be incorporated into the microspheres as free salts, as complexes, e.g., with EDTA, DTPA, DOTA or desferrioxamine, or as oxides of the metal ions. Additionally, derivatized complexes of the metal ions may be bound to lipid head groups, or lipophilic complexes of the ions may be incorporated into a lipid bilayer, for example. When exposed to thermal stimulation, e.g., cavitation, these metal ions then will increase the rate of formation of reactive oxygen intermediates. Further, radiosensitizers such as metronidazole and misonidazole may be incorporated into the gas and gaseous precursor filled microspheres to create free radicals on thermal stimulation.

By way of an example of the use of prodrugs, an acylated chemical group may be bound to a drug via an ester linkage which would readily cleave in vivo by enzymatic action in serum. The acylated prodrug is incorporated into the gas and gaseous precursor filled microsphere of the present invention. The derivatives, in addition to hydrocarbon and substituted hydrocarbon alkyl groups, may also be composed of halo substituted and perhalo substituted groups, such as perfluoroalkyl groups. Perfluoroalkyl groups should possess the ability to stabilize the emulsion from which the microspheres and foam are derived. When the gas and gaseous precursor filled microsphere is burst by the sonic pulse from ultrasound which is applied, as described in detail further below, the prodrug encapsulated by the microsphere will then be exposed to the serum. The ester linkage is then cleaved by esterases in the serum, thereby generating the therapeutic agent.

Other Additives

In addition to the active ingredients, e.g., therapeutic agents and cosmetic agents, there may be added to the gas and gaseous precursor filled microspheres of the present invention, for topical or subcutaneous delivery to a selected tissue of a patient, any one or more of a number of additional compositions which will favorably affect the performance of the microspheres or of the active ingredient which they contain. These compositions may enhance absorbance of the active ingredient, preserve the stabilized microspheres and foam, or add desired color or scent. A number of these additives are described in detail below. Others not mentioned, would readily occur to the skilled artisan and their inclusion, therefore, is contemplated as a part of the present invention.

Bacteriostatic agents may be included with the microspheres to prevent bacterial degradation on storage. Suitable bacteriostatic agents include but are not limited to benzalkonium chloride, benzethonium chloride, benzoic acid, benzyl alcohol, butylparaben, cetylpyridinium chloride, chlorobutanol, chlorocresol, methylparaben, phenol, potassium benzoate, potassium sorbate, sodium benzoate and sorbic acid. One or more antioxidants or oxygen scavengers may further be included with the gas and gaseous precursor filled microspheres to prevent oxidation of the lipid. Suitable antioxidants include tocopherol, ascorbic acid (Vitamin C) and ascorbyl palmitate. Suitable oxygen scavengers include glucose oxidase.

One or a number of preservatives may also be included with the gas and gaseous precursor filled microsphere preparations. Such preservatives include but are not limited to: parabens and quaternary ammonium compounds, various alcohols such as ethyl and isopropyl, phenols such as p-chloro-m-cresol, and essential oils such as citrus and menthol.

The foregoing bacteriostatic agents, antioxidants, oxygen scavengers and preservatives assist in prolonging the shelf life of the microspheres of foams of the invention, which otherwise might be affected by bacterial degradation, oxidative effects or other degradative phenomenon.

Acids, alkalis, buffers and neutralizers may also be included in the formulation. These include but are not limited to compounds such as: citric acid, ammonium carbonate, ammonium bicarbonate, calcium carbonate and tartaric acid. In general the gas and gaseous precursor filled microsphere formulations are stabilized at a pH between 3.0 and pH 10.0. The desired pH range is from pH 4 to pH 9 and even more desirably or preferable between pH 5 and pH 8. The most preferred pH is from pH 6.0 to pH 7.0.

Moisture content control agents or humectants may also be included to prevent the gas and gaseous precursor filled microspheres from drying out. In addition, ointment bases may be used with the gas and gaseous precursor filled microspheres. These ointment bases may include, but are by no means limited to lanolin, lanolin anhydrous, hydrophilic ointment, white ointment, yellow ointment, polyethylene glycol ointment, petrolatum, hydrophilic petrolatum, white petrolatum, rose water ointment, and squalene. Suspending and/or viscosity-increasing agents may be used in conjunction with the gas and gaseous precursor filled microspheres and these may include but are by no means limited to acacia, agar, alginic acid, aluminum monostearate, bentonite, purified bentonite, magma bentonite, carbomer 934P, carboxymethylcellulose calcium, carboxymethylcellulose sodium 12, carboxymethylcellulose sodium, carrageenan, microcrystalline cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, silicon dioxide, colloidal, zinc oxide, sodium alginate tragacanth, and xanthan gum. Other useful agents include but are not limited to: glycerin, hexylene glycol, sorbitol, and propylene glycol. In addition, in some instances it may be useful to prevent excessive moisture formation in the gas and gaseous precursor filled microsphere bilayers. In this case calcium silicate may be added. Other bases and stiffening agents may also be used. These may include cocoa butter, hard fat, hydrogenated castor oil, cetostearyl alcohol, Cetyl alcohol, cetyl esters wax, hard fat, paraffin, polyethylene excipient, stearyl alcohol, emulsifying wax, white wax, and yellow wax. In addition, the gas and gaseous precursor filled microspheres may also be compatible with oleaginous vehicles as almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, and squalene.

For applications of cosmetics and to a lesser extent for therapeutic agents, particularly topical applications, a coloring agent may be useful. Useful coloring agents include: Violet 1, FD&C Blue #1, FD&C Green #33 as well as FD&C Red #44. Natural colors may also be used in cosmetic formulations of the gas and gaseous precursor filled microspheres and these include, but are not limited to: alkanet, annatto, carotene, chlorophyll, cochineal, saffron and tumeric.

Processing aides may be incorporated into the gas and gaseous precursor filled microsphere formulations to influence the smoothness, volume and uniformity of the preparation. Useful agents include, for example, sodium lauryl sulfate and alumina gel, sodium sulfonate, acacia and foaming agents such as dodecylbenzene sulfonic acid.

A skin absorption enhancing agent may also be incorporated into the gas and gaseous precursor filled microspheres or into the aqueous media surrounding the gas and gaseous precursor filled microsphere structures. Such skin absorption enhancers include but are not limited to the following: pyrrolidones such as 2pyrrolidone, N-methyl-2-pyrrolidone (NMP), 1-methyl-2-pyrrolidone, 5-methyl-2-pyrrolidone, 1-ethyl-2-pyrrolidone, 2-pyrrolidone-5-carboxylic acid, N-hydroxyethylpyrrolidone (HEP), N-cyclohexylpyrrolidone (CHP), N-dimethylaminopropylpyrrolidone (DAPP), N-cocalyklpyrrolidone (CAP), N-tallowalkylpyrrolidone (TAP), 1-lauryl-2-pyrrolidone (LP), and 1-hyxyl-2-pyrrolidone (HP); fatty acids such as oleic acid, linoleic acid, heptanoic acid, caproic acid, lauric acid, stearic acid, octadecenoic acid, palmitoleic acid, myristic acid and palmitelaidic acid; sulfoxides such as dimethylsulfoxide (DMSO), dimethylacetamide (DMAC), dimethylformamide (DMF), N-methylformamide (NMF) and decylmethylsulfoxide (DCMS); amines and derivatives such as N,N-diethyl-m-toluamide, dodecylamine, ethoxylated amine, N,N-bis(2-hydroxyethyl)oleylamine, dodecyl-N,N-dimethyl-amino acetate, sodium pryoglutaminate and N-hydroxylethalacetamide; terpenes and terpenoids such as α-pinenes, δ-limonene, 3-carene, α-terpineol, terpinen-4-ol, careol, abisabolol, carvone, pulegone, piperitone, menthone, fenchone, cyclohexene oxide, limonene oxide, pinene oxide, cyclopentene oxide, ascaridol, 7-oxabicyclo(2.2.1)heptane, 1,8-cineole, safrole, 1-carvone, terpenoid cyclohexanone derivatives, acyclic terpenehydrocarbon chains, hydrocarbon terpenes, cyclic ether terpenes, cardamon seed extract, monoterpene terpineol and acetyl terpineol; essential oils of eucalyptus, chenopodium and yang ylang; surfactants whether anionic-sodiumlaurylsulfate (SLS), phenylsulfurate CA, calciumdodecylbenzene sulfonate, empicol ML26/F and magnesiumlaurylsulfate; cationic-cetyltrimethylammonium bromide; nonionic-synperonic NP series and PE series and the polysorbates; or zwiterionic-N-dodecyl-N,N-dimethylbetaine; alcohols such as ethanol, lauryl alcohol, linolenyl alcohol, 1-octanol, 1-propanol and 1-butanol; urea, cyclic unsaturated urea analogs, glycols, azone, n-alkanols, n-alkanes, orgelase, alphaderm cream and water. These may or may not be in a base which can be composed of various substances including but not limited to the following: glycerol, propylene glycol (PG); isopropyl myristate (1PM); urea in propylene glycol, ethanol and water; and polyethylene glycol (PEG).

Various materials which comprise the active ingredients or any of the various additives and other materials used in the present invention may be incorporated into the internal gas and gaseous precursor filled space of the gas and gaseous precursor filled microspheres, particularily liposomes, during the vortexing, gas instillation, or other processes for preparing the gas and gaseous precursor filled microspheres, or into the wall of or onto the internal or external surface of lipid or polymer compound which forms the microsphere. Incorporation onto the external surface of the microspheres is preferred. For example, active ingredients with a high octanol/water partition coefficient may be incorporated directly into a lipid layer surrounding the gas, but incorporation onto the external surface of the gas and gaseous precursor filled lipid microspheres is preferred. To accomplish this, groups capable of binding the active ingredients are generally incorporated into the lipid layers which will then bind these materials. This may be readily accomplished through the use of cationic lipids or cationic polymers which may be incorporated into the dried lipid starting materials. Incorporation of the active ingredient or other additives or materials in the milieu surrounding the microspheres is also contemplated.

Methods of Administration and Use

The present invention provides for topical and subcutaneous delivery of active ingredients, especially drugs and cosmetics, to a selected tissue of a patient, especially the skin.

While topical administration will ordinarily and predominantly be to the skin of a patient, it is not limited thereto, but includes application to any and all tissue surfaces of a patient whether internal or external. Thus, in addition to a patient's skin, other sites of topical administration include various mucosal membranes, such as those of the eye, nose, rectum and vagina. Delivery to the tissue surface sites is local (that is, to the place applied), but there may also be further delivery as a result of absorption and transfer to other tissues, especially systemic delivery via the blood, from the local place of topical administration.

Similarily, subcutaneous administration will ordinarily and predominantly be delivery underneath the skin of a patient by way of injection or the like. However, it is also not limited thereto, but includes application below any and all tissue surfaces of a patient whether internal or external. Thus, in addition to administration below a patient's skin, other sites of subcutaneous administration include beneath the various mucosal membranes, such as those of the eye, nose, rectum and vagina. Delivery to these sites is local (that is, to the place applied), but there may also be further delivery as a result of absorption and transfer to other tissues, especially systemic delivery via the blood, from the local place of subcutaneous administration. It should be noted in particular that absorption and transfer of therapeutic and cosmetic agents to other tissues can be achieved for longer periods of time through the use of subcutaneous depot injections. Generally with subcutaenous injections, the injections are typically immediately below the tissue surface, and are generally no more than about 3.0 cm deep. Preferably the subcutaneous injections are between about 0.05 mm deep and about 1.0 cm deep, more preferably between about 0.1 mm deep and about 1 mm deep, even more preferably between about 0.1 and about 0.5 mm deep, and most preferably about 0.2 mm deep.

The microspheres of the invention are typically, and most conveniently, administered in the forms of foams.

A particularly important embodiment of the topical and subcutaneous administration of the microspheres of the present invention is the use of the microspheres in transdermal delivery systems such as transdermal patches, and in the formation by adsorption or alternatively by subcutaneous injection of a subcutaneous depot. Many therapeutic agents are poorly absorbed from the gastrointestinal tract and often fail, therefore, to provide adequate systemic levels when administered orally. While transdermal patches are effective in delivering some therapeutic agents, e.g., nicotine, and may be employed using the microspheres of the present invention, this approach is much less effective for delivery of larger molecules, e.g., peptides. For peptides such as luteinizing hormone releasing hormone (LHRH) antagonists, and bombesin, in accordance with the prior art, the therapeutic agent must be administered every day, which inevitably requires that the patient undergo considerable pain and discomfort from intramuscular injections.

Figure 1B:
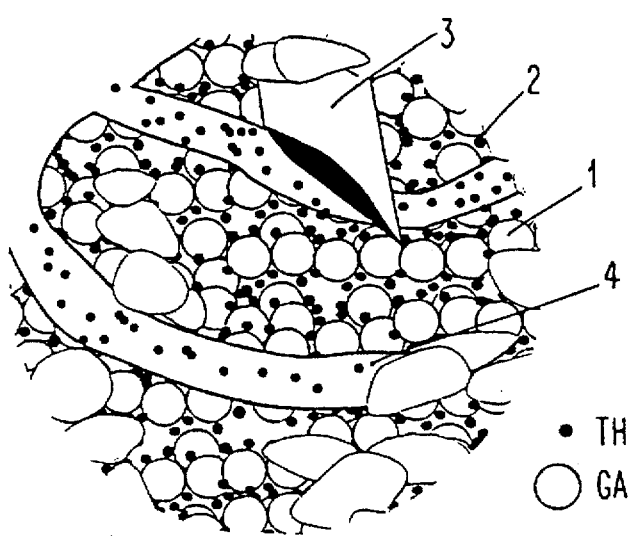
FIG. 1B is an expanded view of the circled area in FIG. 1A.

Thus, a significant benefit of the present invention is the achievement of an alternative route of administration which often reduces the frequency of dosing to once a month or less. As shown in FIG. 1, which depicts the outer and under surfaces of the skin of a patient, shows gas filled microspheres (1) comprising a therapeutic agent (2) being administered subcutaneously by injection with a needle (3), resulting in a subcutaneous depot near blood vessel (4), with some of the therapeutic agent entering the blood stream. In FIG. 1, the therapeutic agent (2) is sequestered within the interstitial spaces between the microspheres, but if desired may also be inside or attached to the individual microspheres. The therapeutic agents may be within the membranes surrounding the microspheres, e.g., within the lipid mono- or bilayers, bound to or adsorbed onto the surface of the microspheres, e.g., through a covalent linkage or van der Waals or electrostatic interaction, or simply found in the thin aqueous spaces surrounding the microspheres which make up the stabilized foam. In any case, the microspheres themselves and the foam which they may collectively comprise act as barriers to the free diffusion of the therapeutic agent. As such, the microspheres and foam acts as a convenient delivery vehicle for subcutaneous administration of the drug.

In conventional sustained release therapeutic agent delivery systems, the therapeutic agents are usually enmeshed within a polymeric matrix such as polylactic acid or polymethacrylate. See, e.g., Kost, J., Leong, K. and Langer, R., "Ultrasonic Modulated Drug Delivery Systems", *Polymers in Medicine* II, Plenum Press, New York and London, pp. 387–396; and Brown, L., and Langer, R. *"Transdermal Delivery of Drugs, Ann. Rev. Med.*, 1988, 39: 221–29. While substantial progress has been achieved in developing sustained release formulations, significant obstacles remain. It is difficult to achieve the desired release kinetics, e.g., release over a period of time in excess of 30 days for a given therapeutic agent. Second, the therapeutic agent may suffer from degradation over the periods of time normally involved in storage. Perhaps most importantly, it has been very difficult to develop sustained delivery systems which are not toxic, e.g., which do not cause local granuloma formation or other tissue damage. It has long been an object in the art to achieve a balance between biodegradability and sustained release. The present invention provides a satisfactory solution to these problems. The microspheres of the present invention permit the artisan to use quite degradable and biocompatible compounds, such as phospholipids and polymers, which act as stabilizing compounds for the gas or gaseous precursors of the microspheres, as sustained delivery depots. In particular, microspheres and foams prepared with perfluorocarbons are quite stable and useful as such delivery systems.

In conventional sustained delivery depots, the release kinetics of the therapeutic agent is mainly due to the composition of the sustaining polymeric matrix, as well as the affinity of the therapeutic agent for the polymer matrix. In the present invention, not only the makeup of the stabilizing compound affects the therapeutic agent release, but also the composition of the gas which is selected to be encapsulated in the microspheres plays a significant role. It has been discovered that relatively soluble gases can be used to make stabilized foam for rapid therapeutic agent delivery. However, highly insoluble gases are preferred for sustained therapeutic agent delivery, e.g., over several weeks. In general, given a comparable stabilizing compound, e.g., using dipalmitoylphosphatidylcholine (DPPC), the microspheres and foam prepared from air, nitrogen, perfluoromethane, perfluoroethane, perfluoropropane, perfluorobutane and perfluoropentane will show increasing stability, respectively, and therapeutic agents included with and encapsulated therein will be released more slowly from the more stable microspheres and foam.

The present invention thus adds a unique capability not obtainable with the delivery systems of the prior art. In the prior art, one could only affect the release of the therapeutic or cosmetic agent by varying the composition of the stabilizing matrix from which the active agent was released. In the present invention, it is possible to select not only the lipid and/or polymer to be employed in the microsphere, but also the gas, and thereby together create the desired stability to the microsphere and foam, and as a result, design the appropriate release kinetics for the drug. As the stabilized microspheres and foam gradually collapse over time, and the gas is released and diffuses away and is eventually dissipated from the patient's body, primarily through the lungs. The gases are preferably inert and the various stabilizing compounds, e.g., a phospholipid, are readily metabolized. The present invention is thus able to provide stable, safe sustained release depots for subcutaneous (including intramuscular or intrahumoral, i.e., within the bone marrow), without the toxicity problems which are present when the systems of the prior art are utilized.

The microspheres and foam of the present invention can be utilized as subcutaneously administered sustained release depot vehicles, and are readily practiced in accordance with the detailed description herein. The therapeutic agent of interest, e.g., a bioactive peptide, is added to the sterile vial used to prepare the microspheres and foam, which contains the stabilizing compound and a head space of gas. The mixture is agitated, e.g., by a Wig-L-Bug™ mechanical shaker, for the desired time, which will typically range from 30 seconds to 2 minutes. The mixture is withdrawn by a syringe and then injected into the patient's body (into the subcutaneous tissues). By varying the concentration of stabilizing compound, e.g., a biocompatible lipid, and by varying the type of gas or gaseous precursor used to make the microspheres, sustained release formulations with different release kinetics can be generated. The present invention has the additional advantage that ultrasound or other energy can be applied to the patient's skin in order to activate and release the therapeutic agent from the depot within the subcutaneous or other tissues where the depot is located. This technique is deemed to be particularly promising for diabetic patients where microspheres and foam containing insulin may be activated using transcutaneous ultrasound following meals and in accordance with the patient's blood sugar levels. By using the microspheres and foam of the present invention in this fashion, subcutaneous injections of the insulin or other therapeutic agent can be avoided and the depot used for both sustained release and sonically augmented release of insulin or other thereapeutic agent.

Also particularly included within the scope of the present invention is topical administration to the lungs, i.e., to the bronchi, bronchioli, and alveoli. For such administration by inhalation to the airways of a patient, the gas and gaseous precursor filled microspheres and foam thereof of the present invention is administered by using a small particle aqueous aerosol generator, e.g., a Collison nebulizer, propelled by air or oxygen-enriched air for formation of the small aqueous particles. See, e.g., Knight et al. U.S. Pat. 5,049,388. As described further herein, the gas and gaseous precursor filled microspheres and foam of the present invention are created by agitation. This agitation can take place prior to placing said microspheres or foam in the aerosol generator, or the aerosol generator can be used as the primary or exclusive source of agitation. Passage through the nebulizer will tend to form gas and gaseous precursor filled microspheres of a desirably reduced size, suitable for entry into the alveoli, the smallest portion of the lung.

Figure 2:
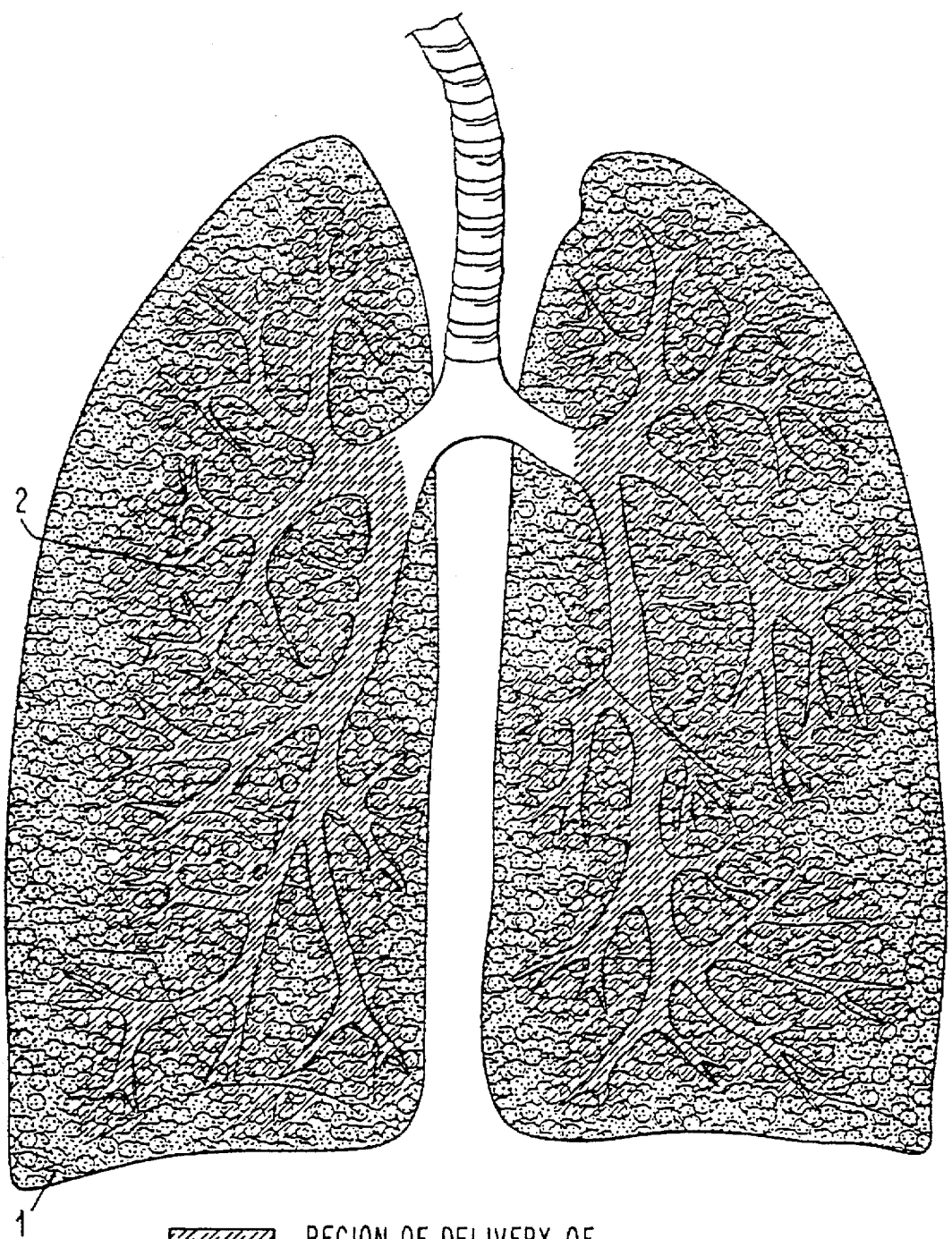
FIG. 2 is a graphic depiction of the topical delivery of the gas filled microspheres and active ingredients of the present invention to the lungs of a patient by inhalation, as compared with the delivery of many conventional microspheres.

Thus, the microspheres of the present invention are useful for the delivery of active agents such as therapeutic agents to the lungs in accordance with the pulmonary delivery described below. As shown in FIG. 2, conventional microspheres (2) and other aerosol compositions deliver the therapeutic agents mainly to the central bronchi and airways and do not reach the terminal bronchioles or alveoli. The gas filled microspheres and active agents (1) may be generally delivered further into the lung, reaching the terminal bronchioles or alveoli. Since conventional liposomes and aerosol compositions are substantially filled with water, they, as essentially water droplets, are substantially more dense than air and their transit into the lungs is limited to the central airways. It is desirable, of course, that the therapeutic agents reach the peripheral airways to treat diseases in the lung, as well as to achieve systemic delivery of pharmaceutically active compounds, e.g., insulin via the pulmonary route. The alveoli provide for such a route of administration primarily because the total surface area of the alveoli is much larger than that of the central airways and hence, the opportunity for therapeutic agents to diffuse into the bloodstream is greatly enhanced. What is required, however, is that therapeutic agents be delivered to these tiny airsacs. The alveoli are circumscribed by thin membranes and are intimately opposed to the capillaries. Conventional aerosols however, fail to reach this most distal part of the lungs. The microspheres and foam of the present invention, however, because they are filled with gas, are much lighter, and thus float, end up being inhaled much further into the deep recesses of the lungs. Additionally, gases which are lighter than air, such as helium, can even be selected to make the microspheres and foam float even further on the air currents during inhalation into the lungs. The microspheres and foam of the present invention which contain therapeutic agents are readily delivered via nebulizers and, in fact, the microspheres tend to be further reduced in size by this process of nebulization, such that very tiny, submicron size microspheres may be achieved and delivery is even more effective. For inhalers and other delivery systems requiring prolonged storage, gases such as perfluorocarbons may be used. For most applications, where the stabilizing compound and therapeutic agent are agitated just prior to administration to produce the microspheres or foam, air or nitrogen as the gas which fills the microspheres will prove adequate.

Gaseous precursors contained in the microspheres of the present invention can, upon activation by temperature, light, or pH, or other properties of the tissues of a patient to which it is administered, undergo a phase transition from a liquid entrapped in the microspheres, to a gaseous state, expanding to create the gas-filled microspheres and foam used in the present invention. Hence, this gaseous precursor filled microsphere is not only a gaseous precursor, but also in a sense, a "foam precursor", and can be used to act essentially as a lathering agent once activated by application to a selected tissue of a patient, where such factors as temperature or pH may be used to cause generation of the gas. Thus, the principle involved in this aspect of the present invention will find particular utility in the preparation of soaps, facial cremes, skin cleansing agents, oleaginous foams, and many other cosmetic vehicles and formulations that are applied topically. These foaming factors provide the lathering necessary to aid in cleansing of a selected tissue and pores.

Thus, in accordance with this particular embodiment of the present invention, there is provided a method for preparing in situ on a selected tissue of a patient, gas filled microspheres comprising an active ingredient, said method comprising the steps of (a) preparing gaseous precursor filled microspheres by agitating an aqueous suspension of a lipid in the presence of one or more gaseous precursors which undergo phase transitions from liquid to gaseous states, optionally in the presence of a gas, whereby microspheres filled with liquid phase gaseous precursor are formed, and wherein said active ingredient is added either before or after said agitation step; and (b) applying said gaseous precursor filled microsphere prepared in the preceding step to a selected tissue of a patient wherein said gaseous precursor is activated by said tissue so as to undergo transition to the gaseous phase. The microspheres become the matrix which establishes a foam. When this method is carried out in the presence of a gas, that gas will preferably be nitrogen. It is further preferred that this method is one wherein the gaseous precursors undergo phase transitions from liquid to gaseous states at or near the normal body temperature of said patient, and are thereby activated by the temperature of said patient skin so as to undergo transition to the gaseous phase thereon. More preferably still, this method is one wherein the patient tissue is human skin having a normal temperature of about 37° C., and wherein the gaseous precursors undergo phase transitions from liquid to gaseous states at or near 37° C.

The method described above also forms an integral part of another aspect of the present invention, a method for the topical delivery of an active ingredient to a selected tissue of a patient comprising the steps of (a) applying to said tissue of said patient a gaseous precursor filled microsphere prepared by agitating an aqueous suspension of a lipid in the presence of one or more gaseous precursors which undergo phase transitions from liquid to gaseous states, optionally in the presence of a gas, whereby microspheres filled with liquid phase gaseous precursor are formed, wherein said active ingredient is added either before or after said agitation; and (b) allowing said gaseous precursor to be activated by said patient tissue so as to undergo transition to the gaseous phase, the resulting expansion providing gas and gaseous precursor filled microspheres containing said active ingredient; and (c) moving said gas and gaseous precursor filled microspheres containing said active ingredient into said patient tissue (e.g., through pores or otherwise). The moving of the microspheres or active ingredients into the said patient tissue will usually be accomplished by rubbing or similar mechanical forcing of the microspheres or active ingredients thereof into said tissue. However, it is also within the scope of the present invention to simply allow the microspheres to remain on a selected tissue, which then absorbs the active ingredients, which are selected from therapeutic agents and cosmetics, over a longer period of time.

As has already been mentioned further above, it is also within the scope of the present invention to dispense with the need for an active ingredient, and to take advantage of the inherent properties of the lipid from which the microspheres and foam are prepared, in order to confer desirable properties to a selected tissue of a patient to which said microspheres and foam are applied. Thus, the present invention also concerns a method for improving the conditioning properties of a selected tissue of a patient comprising topical application to said tissue of gas and gaseous precursor filled microspheres, wherein said lipid possesses skin conditioning (skin improving) properties, especially moisturizing, lubricity, and overall general health.

This aspect of the present invention also has applicability to the microspheres which are prepared using the gaseous precursors, as also described further above. Thus, the present invention includes a method for improving the conditioning properties of a selected tissue of a patient, such as skin, comprising (a) topically applying to said tissue a gaseous precursor filled microsphere prepared by agitating an aqueous suspension of a lipid in the presence of one or more gaseous precursors which undergo phase transitions from liquid to gaseous states, optionally in the presence of a gas, whereby microspheres filled with liquid phase gaseous precursor is formed; (b) allowing said gaseous precursor to be activated by said patient tissue so as to undergo transition to the gaseous phase, the resulting expansion providing gas and gaseous precursor filled microspheres; and (c) moving said microspheres into said tissue of said patient; wherein said lipid possesses tissue conditioning improving properties, especially moisturizing and lubricity. Other tissue conditioning properties which it is desirable to affect positively are feel and lack of tackiness.

It is also within the scope of the present invention to apply the compositions thereof to exposed internal tissues, such as those of the heart during the course of open heart surgery. Further, it is within the scope of the present invention to utilize a sustained-delivery depot route of administration via exposure of internal tissues or absorption of the microspheres into the tissue. All of these contemplated uses are subsumed within the term "topical administration" as used herein.

Ultrasound may be utilized in the present invention to both rupture the gas and gaseous precursor filled microspheres and to cause thermal effects which may increase the rate of the chemical cleavage and the release of the active therapeutic agent from the prodrug. The rupturing of the microspheres of the present invention and the cleavage of prodrugs is carried out in a surprisingly easy manner by applying ultrasound of a certain frequency to the region of the patient where therapy is desired, after the microspheres of the invention have been administered to or has otherwise reached that region. When ultrasound is applied at a frequency corresponding to the peak resonant frequency of the therapeutic agent containing gas and gaseous precursor filled microspheres, the microspheres may rupture and release their contents and the prodrug may cleavage releasing the active therapeutic agent from the prodrug.

The peak resonant frequency can be determined either in vivo or in vitro, but preferably in vivo, by exposing the microspheres to ultrasound, receiving the reflected resonant frequency signals and analyzing the spectrum of signals received to determine the peak, using conventional means. The peak, as so determined, corresponds to the peak resonant frequency, or fundamental frequency (first harmonic), as it is sometimes termed. The second harmonic (or the 2× multiple of the fundamental frequency) may also be determined.

Preferably, the microspheres of the present invention have a peak resonant frequency of between about 0.5 mHz and about 10 mHz. Of course, the peak resonant frequency of the gas and gaseous precursor filled microspheres of the present invention will vary depending on the outside diameter and, to some extent, the elasticity or flexibility of the microspheres, with the larger and more elastic or flexible microspheres having a lower resonant frequency than the smaller and less elastic or flexible microspheres.

The therapeutic agent containing gas and gaseous precursor filled microspheres may also rupture and the prodrugs may be cleaved when exposed to non-peak resonant frequency ultrasound in combination with a higher intensity (wattage) and duration (time). This higher energy, however, results in greatly increased heating, which may not be desirable. By adjusting the frequency of the energy to match the peak resonant frequency, the efficiency of rupture and therapeutic agent release is improved, appreciable tissue heating does not generally occur (frequently no increase in temperature above about 2° C.), and less overall energy is required. Thus, application of ultrasound at the peak resonant frequency, while not required, is most preferred.

Any of the various types of diagnostic ultrasound imaging devices may be employed in the practice of the present invention, the particular type or model of the device not being critical to the method use of the present invention. Also suitable are devices designed for administering ultrasonic hyperthermia, such devices being described in U.S. Pat. Nos. 4,620,546; 4,658,828; and 4,586,512, the disclosures of each of which are hereby incorporated herein by reference in their entirety. Preferably, the device employs a resonant frequency (RF) spectral analyzer. The transducer probes may be applied externally or may be implanted. Ultrasound is generally initiated at lower intensity and duration, and then intensity, time, and/or resonant frequency are increased until the microspheres rupture.

Although application of the various principles described above will be readily apparent to one skilled in the art, viewed in light of the present disclosure, by way of general guidance it is noted that for gas and gaseous precursor filled microspheres of about 1.5 to about 10 microns in mean outside diameter, the resonant frequency will generally be in the range of about 1 to about 10 megahertz. By adjusting the focal zone to the center of the target tissue, the gas and gaseous precursor filled microspheres can be visualized under real time ultrasound as they accumulate within the target tissue. Using the 7.5 megahertz curved array transducer as an example, adjusting the power delivered to the transducer to maximum and adjusting the focal zone within the target tissue, the spatial peak temporal average (SPTA) power will then be a maximum of approximately 5.31 mW/cm$^2$ in water. This power will cause some release of therapeutic agent from the gas and gaseous precursor filled microspheres, but much greater release can be accomplished by using higher power.

By switching the transducer to the doppler mode, higher power outputs are available, up to 2.5 watts per cm$^2$ from the same transducer. With the machine operating in doppler mode, the power can be delivered to a selected focal zone within the target tissue and the gas and gaseous precursor filled microspheres can be made to release their therapeutic agents. Selecting the transducer to match the resonant frequency of the gas and gaseous precursor filled microspheres will make this process of therapeutic agent release even more efficient.

For larger diameter gas and gaseous precursor filled microspheres, e.g., greater than 3 microns in mean outside diameter, a lower frequency transducer may be more effective in accomplishing therapeutic agent release. For example, a lower frequency transducer of 3.5 megahertz, e.g., a 20 mm curved array model, may be selected to correspond to the resonant frequency of the gas and gaseous precursor filled microspheres. Using this transducer, 101.6 milliwatts per cm$^2$ may be delivered to the focal spot, and switching to doppler mode will increase the power output (SPTA) to 1.02 watts per cm$^2$.

To use the phenomenon of cavitation to release and/or activate the therapeutic agents/prodrugs within the gas and gaseous precursor filled microspheres, lower frequency energies may be used, as cavitation occurs more effectively at lower frequencies. Using a 0.757 megahertz transducer driven with higher voltages (as high as 300 volts) cavitation of solutions of gas and gaseous precursor filled microspheres will occur at thresholds of about 5.2 atmospheres.

Table 3 shows the ranges of energies transmitted to tissues from diagnostic ultrasound on commonly used instruments such as the Piconics Inc. (Tyngsboro, Mass.) Portascan general purpose scanner with receiver pulser 1966 Model 661; the Picker (Cleveland, Ohio.) Echoview 8L Scanner including 80C System or the Medisonics (Mountain View, Calif.) Model D-9 Versatone Bidirectional Doppler. In general, these ranges of energies employed in pulse repetition are useful for monitoring the gas and gaseous precursor filled microspheres, but are insufficient to rupture the microspheres of the present invention.

TABLE 3

Power and Intensities Produced by Diagnostic Equipment*

| Pulse repetition rate (Hz) | Total ultrasonic power output P (mW) | Average Intensity at transducer face $I_{ID}$ (W/m$^2$) |
|---|---|---|
| 520 | 4.2 | 32 |
| 676 | 9.4 | 71 |
| 806 | 6.8 | 24 |
| 1000 | 14.4 | 51 |
| 1538 | 2.4 | 8.5 |

*Values obtained from Carson et al., Utlrasound in Med. & Biol. 1978, 3, 341–350, the disclosures of which are hereby incorporated herein by reference in their entirety.

Higher energy ultrasound such as commonly employed in therapeutic ultrasound equipment is preferred for activation of the therapeutic agent containing gas and gaseous precursor filled microspheres. In general, therapeutic ultrasound machines employ as much as 50% to 100% duty cycles dependent upon the area of tissue to be heated by ultrasound. Areas with larger amounts of muscle mass (i.e., backs, thighs) and highly vascularized tissues such as heart may require the larger duty cycle, e.g., 100%.

In diagnostic ultrasound, one or several pulses of sound are used and the machine pauses between pulses to receive the reflected sonic signals. The limited number of pulses used in diagnostic ultrasound limits the effective energy which is delivered to the tissue which is being imaged.

In therapeutic ultrasound, continuous wave ultrasound is used to deliver higher energy levels. In using the microspheres of the present invention, the sound energy may be pulsed, but continuous wave ultrasound is preferred. If pulsing is employed, the sound will preferably be pulsed in echo train lengths of at least about 8 and preferably at least about 20 pulses at a time.

Either fixed frequency or modulated frequency ultrasound may be used. Fixed frequency is defined wherein the frequency of the sound wave is constant over time. A modulated frequency is one in which the wave frequency changes over time, for example, from high to low (PRICH) or from low to high (CHIRP). For example, a PRICH pulse with an initial frequency of 10 MHz of sonic energy is swept to 1 MHz with increasing power from 1 to 5 watts. Focused, frequency modulated, high energy ultrasound may increase the rate of local gaseous expansion within the microspheres and rupturing to provide local delivery of therapeutic agents.

The frequency of the sound used may vary from about 0.025 to about 100 megahertz. Frequency ranges between about 0.75 and about 3 megahertz are preferred and frequencies between about 1 and about 2 megahertz are most preferred. Commonly used therapeutic frequencies of about 0.75 to about 1.5 megahertz may be used. Commonly used diagnostic frequencies of about 3 to about 7.5 megahertz may also be used. For very small microspheres, e.g., below 0.5 micron in mean outside diameter, higher frequencies of sound may be preferred as these smaller microspheres will absorb sonic energy more effectively at higher frequencies of sound. When very high frequencies are used, e.g., over 10 megahertz, the sonic energy will generally have limited depth penetration into fluids and tissues. External application will be preferred for the skin and other superficial tissues.

Although the use of ultasound as a means of rupturing or otherwise deforming the microspheres and foam of the present invention, so as to cause release of the active ingredient contained therein, especially a therapeutic agent, is a preferred embodiment, it will be apparent to the artisan in light of the instant disclosure, that other means and forms of energy can be utilized to accomplish the same objective. For example, microwave and other forms of radiofrequency energy, magnetic induction oscillating energy, and light energy in its various forms, can be used to induce release of the active ingredient from the microspheres and foam of the present invention.

Where the gas and gaseous precursor filled microspheres are used for active agent delivery, the active agent to be delivered may be embedded within the wall of the microsphere, encapsulated in the microsphere and/or attached to the internal or external wall of the microsphere, as desired. The active agent may also be found in the milieu surrounding the microspheres. The phrase "attached to" or variations thereof, as used herein in connection with the location of the active agent, means that the active agent is linked in some manner to the inside and/or the outside wall of the microsphere, such as through a covalent or ionic bond or other means of chemical or electrochemical linkage or interaction. The phrase "encapsulated in variations thereof" as used in connection with the location of the active agent denotes that the active agent is located in the internal microsphere void. The phrase "embedded within" or variations thereof as used in connection with the location of the active agent, signifies the positioning of the active agent within the microsphere wall. The phrase "in admixture with" as used in conjunction with the active agent denotes that the active agent is located in the milieu surrounding the microspheres, but is not attached thereto. The phrase "comprising an active" denotes all of the varying types of active agent positioning in connection with the microspheres. Thus, the active agent can be positioned variably, such as, for example, entrapped within the internal void of the gas and gaseous precursor filled microsphere, situated between the gas or gaseous precursor and the internal wall of the gas and gaseous precursor filled microsphere, incorporated onto the external surface of the gas and gaseous precursor filled microsphere and/or enmeshed within the microsphere structure itself. It may also be found in the surrounding milieu.

If desired, more than one active agent may be applied using the microspheres and foam of the present invention. For example, a single microsphere may contain more than one active agent, or microspheres containing different active agents may be co-administered. Similarly, prodrugs may be encapsulated in the microspheres, and are included within the ambit of the phrases active agent or therapeutic agent, as used herein.

Any of a variety of active agents in addition to those set out above, may be encapsulated in the gas and gaseous precursor filled microspheres of the present invention.

The microspheres and foam of the invention may be administered topically or subcutaneously to a patient. The patient may be any type of animal, and is preferably a vertebrate, more preferably a mammal and most preferably a human. The useful dosage to be administered, as one skilled in the art will recognize, will vary based upon such factors as the age, size, and type of patient to which the compositions of the invention are to be administered, the manner in which administration is to be effected (topically, subcutaneously; with/without a depot), the particular therapeutic, cosmetic or other application intended, and the desired therapeutic, cosmetic or other effect sought. Once armed with the foregoing information, one skilled in the art will be readily able to dosage levels. Typically, dosage is initiated at lower, even homeopathic, levels and increased until the desired therapeutic, cosmetic or other effect is achieved.

The stable, gas and gaseous precursor filled microspheres and foam of the present invention have a number of desirable qualities for use in skin care products. First, the fact that they are gas and gaseous precursor filled, they may be useful in protecting therapeutic agents, cosmetics and other materials. Although the microspheres of the prior art may be stored under nitrogen, they will generally be exposed to gases such as oxygen when the bottle is opened. If the therapeutic or other agents in said microspheres are easily oxidized, then this may result in degradation of the product and loss of potency. Because the microspheres and foam of the present invention are filled with gas, a specific gas may be selected to minimize degradation of the product. For example, microspheres filled with nitrogen gas are generally preferred for topical or subcutaneous delivery of compounds which otherwise might be readily oxidized. Microspheres and foam filled with argon also represent a preferred embodiment of the present invention, since argon is heavier than air and will tend to prevent migration of air into the microspheres, with the attendant advantages already described. The use of a perfluorocarbon gas or gases is likewise advantageous in that it has been found that the microspheres produced using them are much more durable, and require significantly less stabilizing compound, e.g., a biocompatible lipid to stabilize the gas filled microsphere. Additionally, the microspheres and foam may be prepared from degassed water to remove trace concentrations of oxygen from the aqueous solvent used to prepare the microspheres and foam.

Methods of Preparation

The stabilized gas and gaseous precursor filled microspheres and foams used in the present invention may be prepared by a number of suitable methods. These are described below separately for the case where the microspheres are gas filled, and where they are gaseous precursor filled, although microspheres having both a gas and gaseous precursor are part of the present invention.

Utilizing a Gas

A preferred embodiment comprises the steps of agitating an aqueous solution containing a stabilizing compound, preferably a lipid, in the presence of a gas at a temperature below the gel to liquid crystalline phase transition temperature of the lipid to form gas and gaseous precursor filled microspheres. The term agitating, and variations thereof, as used herein, means any motion that shakes an aqueous solution such that gas is introduced from the local ambient environment into the aqueous solution. The shaking must be of sufficient force to result in the formation of microspheres, particularily stabilized microspheres. The shaking may be by swirling, such as by vortexing, side-to-side, or up-anddown motion. Different types of motion may be combined. Also, the shaking may occur by shaking the container holding the aqueous lipid solution, or by shaking the aqueous solution within the container without shaking the container itself.

Further, the shaking may occur manually or by machine. Mechanical shakers that may be used include, for example, a shaker table such as a VWR Scientific (Cerritos, Calif.) shaker table, or a Wig-L-Bug® Shaker from Crescent Dental Mfg. Ltd., Lyons, Ill., which has been found to give excellent results. It is a preferred embodiment of the present invention that certain modes of shaking or vortexing be used to make stable microspheres within a preferred size range. Shaking is preferred, and it is preferred that this shaking be carried out using the Wig-L-Bug® mechanical shaker. In accordance with this preferred method, it is preferred that a reciprocating motion be utilized to generate the gas and gaseous precursor filled microspheres. It is even more preferred that the motion be reciprocating in the form of an arc. It is still more preferred that the motion be reciprocating in the form of an arc between about 2° and about 20°, and yet further preferred that the arc be between about 5° and about 8°. It is most preferred that the motion is reciprocating between about 6° and about 7°, most particularly about 6.5°. It is contemplated that the rate of reciprocation, as well as the arc thereof, is critical to determining the amount and size of the gas and gaseous precursor filled microspheres formed. It is a preferred embodiment of the present invention that the number of recipreciprocations, i.e., full cycle oscillations, be within the range of about 1000 and about 20,000 per minute. More preferably, the number of reciprocations or oscillations will be between 2500 and 8000. The Wig-L-Bug®, referred to above, is a mechanical shaker which provides 2000 pestle strikes every 10 seconds, i.e., 6000 oscillations every minute. Of course, the number of oscillations is dependent upon the mass of the contents being agitated, with the larger the mass, the fewer the number of oscillations).

Another means for producing shaking includes the action of gas emitted under high velocity or pressure. It will also be understood that preferably, with a larger volume of aqueous solution, the total amount of force will be correspondingly increased. Vigorous shaking is defined as at least about 60 shaking motions per minute, and is preferred. Vortexing at least 60–300 revolutions per minute is more preferred. Vortexing at 300–1800 revolutions per minute is most preferred. The formation of gas and gaseous precursor filled microspheres upon shaking can be detected visually. The concentration of lipid required to form a desired stabilized microsphere level will vary depending upon the type of lipid used, and may be readily determined by routine experimentation. For example, in preferred embodiments, the concentration of 1,2-dipalimitoyl-phosphatidylcholine (DPPC) used to form stabilized microspheres according to the methods of the present invention is about 0.1 mg/ml to about 30 mg/ml of saline solution, more preferably from about 0.5 mg/ml to about 20 mg/ml of saline solution, and most preferably from about 1 mg/ml to about 10 mg/ml of saline solution. The concentration of distearoylphosphatidylcholine (DSPC) used in preferred embodiments is about 0.1 mg/ml to about 30 mg/ml of saline solution, more preferably from about 0.5 mg/ml to about 20 mg/ml of saline solution, and most preferably from about 1 mg/ml to about 10 mg/ml of saline solution.

In addition to the simple shaking methods described above, more elaborate, but for that reason less preferred, methods can also be employed, e.g., liquid crystalline shaking gas instillation processes, and vacuum drying gas instillation processes, such as those described in U.S. Ser. No. 076,250, filed Jun. 11, 1993, which is incorporated herein by reference, in its entirety. When such processes are used, the stabilized microspheres which are to be gas and gaseous precursor filled, may be prepared prior to gas installation using any one of a variety of conventional liposome preparatory techniques which will be apparent to those skilled in the art. These techniques include freeze-thaw, as well as techniques such as sonication, chelate dialysis, homogenization, solvent infusion, microemulsification, spontaneous formation, solvent vaporization, French pressure cell technique, controlled detergent dialysis, and others, each involving preparing the microspheres in various fashions in a solution containing the desired active ingredient so that the therapeutic, cosmetic or other agent is encapsulated in, enmeshed in, or attached the resultant polar-lipid based microsphere. See, e.g., Madden et al., *Chemistry and Physics of Lipids*, 1990 53, 37–46, the disclosure of which is hereby incorporated herein by reference in its entirety.

Alternatively, active ingredients may be loaded into the microspheres using pH gradient techniques which, as those skilled in the art will recognize, is particularly applicable to therapeutics or cosmetics which either proteinate or deproteinate at a particular pH.

The gas and gaseous precursor filled microspheres prepared in accordance with the methods described above range in size from below a micron to over 100μ in size. In addition, it will be noted that after the extrusion and sterilization procedures, the agitation or shaking step yields gas and gaseous precursor filled microspheres with little to no residual anhydrous lipid phase (Bangham, A. D., Standish, M. M, & Watkins, J. C. (1965) *J. Mol. Biol.* 13, 238–252) present in the remainder of the solution. The resulting gas and gaseous precursor filled microspheres remain stable on storage at room temperature for a year or even longer.

The size of gas and gaseous precursor filled microspheres can be adjusted, if desired, by a variety of procedures including microemulsification, vortexing, extrusion, filtration, sonication, homogenization, repeated freezing and thawing cycles, extrusion under pressure through pores of defined size, and similar methods. However, generally, it is most desirable to use the microspheres and foam of the present invention as they are formed, as described further below, without any attempt at further modification of the size thereof.

The gas and gaseous precursor filled microspheres may be sized by a simple process of extrusion through filters; the filter pore sizes control the size distribution of the resulting gas and gaseous precursor filled microspheres. By using two or more cascaded, i.e., a stacked set of filters, e.g. 10μ followed by 8μ, the gas and gaseous precursor filled microspheres have a very narrow size distribution centered around 2–9 μm. After filtration, these stabilized gas and gaseous precursor filled microspheres remain stable for over 24 hours.

In preferred embodiments, the stabilizing compound solution or suspension is extruded through a filter and the said solution or suspension is heat sterilized prior to shaking. Once gas and gaseous precursor filled microspheres are formed, they may be filtered for sizing as described above. These steps prior to the formation of gas and gaseous precursor filled microspheres provide the advantages, for example, of reducing the amount of unhydrated stabilizing compound, and thus providing a significantly higher yield of gas and gaseous precursor filled microspheres, as well as and providing sterile gas and gaseous precursor filled microspheres ready for administration to a patient. For example, a mixing vessel such as a vial or syringe may be filled with a filtered stabilizing compound, especially lipid suspension, and the suspension may then be sterilized within the mixing vessel, for example, by autoclaving. Gas may be instilled into the lipid suspension to form gas and gaseous precursor filled microspheres by shaking the sterile vessel. Preferably, the sterile vessel is equipped with a filter positioned such that the gas and gaseous precursor filled microspheres pass through the filter before contacting a patient.

The first step of this preferred method, extruding the stabilizing, especially lipid, solution through a filter, decreases the amount of unhydrated compound by breaking up the dried compound and exposing a greater surface area for hydration. Preferably, the filter has a pore size of about 0.1 to about 5 μm, more preferably, about 0.1 to about 4 μm, even more preferably, about 0.1 to about 2 μm, and most preferably, about 1 μm. Unhydrated compound, especially lipid, appears as amorphous clumps of non-uniform size and is undesirable.

The second step, sterilization, provides a composition that may be readily administered to a patient. Preferably, sterilization is accomplished by heat sterilization, preferably, by autoclaving the solution at a temperature of at least about 100° C., and more preferably, by autoclaving at about 100° C. to about 130° C., even more preferably, about 110° C. to about 130° C., even more preferably, about 120° C. to about 130° C., and most preferably, about 130° C. Preferably, heating occurs for at least about 1 minute, more preferably, about 1 to about 30 minutes, even more preferably, about 10 to about 20 minutes, and most preferably, about 15 minutes.

If desired, alternatively the first and second steps, as outlined above, may be reversed, or only one of the two steps employed.

Where sterilization occurs by a process other than heat sterilization at a temperature which would cause rupture of the gas and gaseous precursor filled microspheres, sterilization may occur subsequent to the formation of the gas and gaseous precursor filled microspheres, and is preferred. For example, gamma radiation may be used before and/or after gas and gaseous precursor filled microspheres are formed.

The formation of gas and gaseous precursor filled microspheres upon shaking can be detected by the presence of a foam on the top of the aqueous solution. This is coupled with a decrease in the volume of the aqueous solution upon the formation of foam. Preferably, the final volume of the foam is at least about four times the initial volume of the aqueous solution; and most preferably, all of the aqueous lipid solution is converted to foam.

The required duration of shaking time may be determined by detection of the formation of foam. For example, 10 ml of lipid solution in a 50 ml centrifuge tube may be vortexed for approximately 15–20 minutes. At this time, the foam may cause the solution containing the gas and gaseous precursor filled microspheres to rise to a level of 30 to 35 ml.

The concentration of lipid required to form a preferred foam level will vary depending upon the type of lipid used, and may be readily determined by routine experimentation. For example, in preferred embodiments, the concentration of 1,2-dipalimitoyl-phosphatidylcholine (DPPC) used to form a stabilized foam according to the methods of the present invention is about 20 mg/ml to about 30 mg/ml of saline solution, more preferably from about 10 mg/ml to about 20 mg/ml of saline solution, and most preferably from about 1 mg/ml to about 10 mg/ml of saline solution. The concentration of distearoylphosphatidylcholine (DSPC) used in preferred embodiments is about 20 mg/ml to about 30 mg/ml of saline solution.

Specifically, DPPC in a concentration of 20 mg/ml to 30 mg/ml, upon shaking with or in air, yields a total suspension and entrapped gas volume four times greater than the suspension volume alone. DSPC in a concentration of 10 mg/ml, upon shaking, yields a total volume completely devoid of any liquid suspension volume and contains entirely stabilized foam. Perfluorocarbons (PFC's) can also be used to yield large volumes of stabilized foam with the advantage of using much less stabilizing compound, e.g., biocompatible lipid to stabilize the foam. For example, in some instances, the amount of lipid required has been estimated at one (1) to two (2) orders of magnitude less than would otherwise be the case.

Utilizing Gaseous Precursors

In addition to the aforementioned embodiments, one can also use gaseous precursors contained in the microspheres that can, upon activation by temperature, light, or pH, or other properties of the tissues of a patient to which it is administered, undergo a phase transition from a liquid entrapped in the microspheres, to a gaseous state, expanding to create the stabilized, gas-filled microspheres used in the present invention. This technique is described in detail in copending patent applications Ser. Nos. 160,232 and 159,687, both filed Nov. 30, 1993, each of which are incorporated herein by reference in their entirety.

The preferred method of activating the gaseous precursor is by temperature. Activation or transition temperature, and like terms, refer to the boiling point of the gaseous precursor, the temperature at which the liquid to gaseous phase transition of the gaseous precursor takes place. Useful gaseous precursors are those gases which have boiling points in the range of about −100° C. to 70° C. The activation temperature is particular to each gaseous precursor. An activation temperature of about 37° C., or human body temperature, is preferred for gaseous precursors of the present invention. Thus, a liquid gaseous precursor is activated to become a gas at 37° C. However, the gaseous precursor may be in liquid or gaseous phase for use in the methods of the present invention. The methods of preparing the microsphere or foam topical or subcutaneous delivery agents used in the present invention may be carried out below the boiling point of the gaseous precursor such that a liquid is incorporated into a microsphere. In addition, the said methods may be performed at the boiling point of the gaseous precursor such that a gas is incorporated into a microsphere. For gaseous precursors having low temperature boiling points, liquid precursors may be emulsified using a microfluidizer device chilled to a low temperature. The boiling points may also be depressed using solvents in liquid media to utilize a precursor in liquid form. Further, the methods may be performed where the temperature is increased throughout the process, whereby the process starts with a gaseous precursor as a liquid and ends with a gas.

The gaseous precursor may be selected so as to form the gas in situ in the targeted tissue or fluid, in vivo upon entering the patient or animal, prior to use, during storage, or during manufacture. The methods of producing the temperature-activated gas and gaseous precursor filled microspheres may be carried out at a temperature below the boiling point of the gaseous precursor. In this embodiment, the gaseous precursor is entrapped within a microsphere such that the phase transition does not occur during manufacture. Instead, the gas and gaseous precursor filled microspheres are manufactured in the liquid phase of the gaseous precursor. Activation of the phase transition may take place at any time as the temperature is allowed to exceed the boiling point of the precursor. Also, knowing the amount of liquid in a droplet of liquid gaseous precursor, the size of the microspheres upon attaining the gaseous state may be determined.

Alternatively, the gaseous precursors may be utilized to create stable gas-filled microspheres which are pre-formed prior to use. In this embodiment, the gaseous precursor is added to a container housing a suspending and/or stabilizing medium at a temperature below the liquid-gaseous phase transition temperature of the respective gaseous precursor. As the temperature is then exceeded, and an emulsion is formed between the gaseous precursor and liquid solution, the gaseous precursor undergoes transition from the liquid to the gaseous state. As a result of this heating and gas formation, the gas displaces the air in the head space above the liquid suspension so as to form gas-filled lipid spheres which entrap the gas of the gaseous precursor, ambient gas (e.g. air), or coentrap gas state gaseous precursor and ambient air. This phase transition can be used for optimal mixing and stabilization of the microsphere based foam. For example, the gaseous precursor, perfluorobutane, can be entrapped in the biocompatible lipid or other stabilizing compound, and as the temperature is raised, beyond 4° C. (boiling point of perfluorobutane) stabilizing compound entrapped fluorobutane gas results. As an additional example, the gaseous precursor fluorobutane, can be suspended in an aqueous suspension containing emulsifying and stabilizing agents such as glycerol or propylene glycol and vortexed on a commercial vortexer. Vortexing is commenced at a temperature low enough that the gaseous precursor is liquid and is continued as the temperature of the sample is raised past the phase transition temperature from the liquid to gaseous state. In so doing, the precursor converts to the gaseous state during the microemulsification process. In the presence of the appropriate stabilizing agents, surprisingly, stable gas-filled microspheres result.

Accordingly, the gaseous precursors may be selected to form a gas-filled microsphere in vivo or may be designed to produce the gas-filled microsphere in situ, during the manufacturing process, on storage, or at some time prior to use.

As a further embodiment of this invention, by pre-forming the liquid state of the gaseous precursor into an aqueous emulsion and maintaining a known size, the maximum size of the microbubble may be estimated by using the ideal gas law, once the transition to the gaseous state is effectuated. For the purpose of making gas-filled microspheres from gaseous precursors, the gas phase is assumed to form instantaneously and no gas in the newly formed microsphere has been depleted due to diffusion into the liquid, which is generally aqueous in nature. Hence, from a known liquid volume in the emulsion, one would be able to predict an upper limit to the size of the gas-filled microsphere.

Pursuant to the present invention, an emulsion of a stabilizing compound such as a lipid, and a gaseous precursor, containing liquid droplets of defined size may be formulated, such that upon reaching a specific temperature, the boiling point of the gaseous precursor, the droplets will expand into gas-filled microspheres of defined size. The defined size represents an upper limit to the actual size because factors such as gas diffusion into solution, loss of gas to the atmosphere, and the effects of increased pressure are factors for which the ideal gas law cannot account.

The ideal gas law and the equation for calculating the increase in volume of the gas bubbles on transition from the liquid to gaseous states is as follows:

$$PV=nRT$$

where

P=pressure in atmospheres

V=volume in liters n=moles of gas

T=temperturs in °K

R=ideal gas constant=22.4 L atmospheres $deg^{-1}$ $mole^{-1}$

With knowledge of volume, density, and temperature of the liquid in the emulsion of liquids, the amount (e.g. number of moles) of liquid precursor as well as the volume of liquid precursor, a priori, may be calculated, which when converted to a gas, will expand into a microsphere of known volume. The calculated volume will reflect an upper limit to the size of the gas-filled microsphere, assuming instantaneous expansion into a gas-filled microsphere and negligible diffusion of the gas over the time of the expansion.

Thus, for stabilization of the precursor in the liquid state in an emulsion wherein the precursor droplet is spherical, the volume of the precursor droplet may be determined by the equation:

$$\text{Volume (sphere)}=4/3\ \pi r^3$$

where r=radius of the sphere

Thus, once the volume is predicted, and knowing the density of the liquid at the desired temperature, the amount of liquid (gaseous precursor) in the droplet may be determined. In more descriptive terms, the following can be applied:

$$V_{gas}=4/3\ \pi(r_{gas})^3$$

by the ideal gas law, $$PV=nRT$$

substituting reveals, $$V_{gas}=nRT/P_{gas}$$

or, (A) $n=4/3[\pi r_{gas}^3]P/RT$ amount $n=4/3[\pi r_{gas}^3 P/RT]*MW_n$

Converting back to a liquid volume (B) $V_{liq}=[4/3[\pi r_{gas}^3]P/RT]*\ MW_n/D]$ where D=the density of the precursor Solving for the diameter of the liquid droplet, (C) $\text{diameter}/2=[3/4\ \ \pi[4/3*[\pi r_{gas}^3]P/RT]MW_n/D]^{1/3}$ which reduces to $\text{Diameter}=2[[r_{gas}^3]P/RT\ [MW_n/D]]^{1/3}$ As a further means of preparing microspheres of the desired size for use as stabilized foam topical or subcutaneous delivery agents, and with a knowledge of the volume and especially the radius of the stabilizing compound/precursor liquid droplets, one can use appropriately sized filters in order to size the gaseous precursor droplets to the appropriate diameter sphere.

An emulsion of a particular size could be easily achieved by the use of an appropriately sized filter. In addition, as seen by the size of the filter necessary to form gaseous precursor droplets of defined size, the size of the filter would also suffice to remove any possible bacterial contaminants and, hence, can be used as a sterile filtration as well.

This embodiment for preparing gas-filled microspheres used as topical or subcutaneous delivery agents in the methods of the present invention may be applied to all gaseous precursors activated by temperature. In fact, depression of the freezing point of the solvent system allows the use gaseous precursors which would undergo liquid-to-gas phase transitions at temperatures below 0° C. The solvent system can be selected to provide a medium for suspension of the gaseous precursor. For example, 20% propylene glycol miscible in buffered saline exhibits a freezing point depression well below the freezing point of water alone. By increasing the amount of propylene glycol or adding materials such as sodium chloride, the freezing point can be depressed even further.

The selection of appropriate solvent systems may be determined by physical methods as well. When substances, solid or liquid, herein referred to as solutes, are dissolved in a solvent, such as water based buffers for example, the freezing point is lowered by an amount that is dependent upon the composition of the solution. Thus, as defined by Wall, one can express the freezing point depression of the solvent by the following equation:

$$lnx_a = ln(1-x_b) = \Delta H_{fus}/R(1/T_o - 1/T)$$

where:

$x_a$=mole fraction of the solvent $x_b$=mole fraction of the solute $\Delta H_{fus}$=heat of fusion of the solvent $T_o$=Normal freezing point of the solvent The normal freezing point of the solvent results from solving the equation. If $x_b$ is small relative to $x_a$, then the above equation may be rewritten:

$$x^b = \Delta H_{fus}/R[T-T_o/T_oT] = \Delta H_{fus}\Delta T/RT_o^2$$

The above equation assumes the change in temperature $\Delta T$ is small compared to $T_2$. The above equation can be simplified further assuming the concentration of the solute (in moles per thousand grams of solvent) can be expressed in terms of the molality, m. Thus, $$X_b = m/[m+1000/m_a] = mMa/1000$$

where:

Ma=Molecular weight of the solvent, and m=molality of the solute in moles per 1000 grams.

Thus, substituting for the fraction $X_b$:

$$\Delta T = [M_aRT_o^2/1000\Delta H_{fus}]m$$

or $\Delta T = K_f m$, where $$K_f = M_aRT_o^2/1000\Delta H_{fus}$$

$K_f$ is referred to as the molal freezing point and is equal to 1.86 degrees per unit of molal concentration for water at one atmosphere pressure. The above equation may be used to accurately determine the molal freezing point of gaseous-precursor filled microsphere solutions used in the present invention.

Hence, the above equation can be applied to estimate freezing point depressions and to determine the appropriate concentrations of liquid or solid solute necessary to depress the solvent freezing temperature to an appropriate value.

Methods of preparing the temperature activated gas and gaseous precursor filled microspheres include:

(a) vortexing an aqueous suspension of gaseous precursor-filled microspheres used in the present invention; variations on this method include optionally autoclaving before shaking, optionally heating an aqueous suspension of gaseous precursor and lipid, optionally venting the vessel containing the suspension, optionally shaking or permitting the gaseous precursor microspheres to form spontaneously and cooling down the gaseous precursor filled microsphere suspension, and optionally extruding an aqueous suspension of gaseous precursor and lipid through a filter of about 0.22μ, alternatively, filtering may be performed during in vivo administration of the resulting microspheres such that a filter of about 0.22μ is employed;

(b) a microemulsification method whereby an aqueous suspension of gas and gaseous precursor filled microspheres of the present invention is emulsified by agitation and heated to form microspheres prior to administration to a patient; and (c) forming a gaseous precursor in lipid suspension by heating, and/or agitation, whereby the less dense gas and gaseous precursor filled microspheres float to the top of the solution by expanding and displacing other microspheres in the vessel and venting the vessel to release air; and (d) in any of the above methods, utilizing a sealed vessel to hold the aqueous suspension of gaseous precursor and stabilizing compound such as biocompatible lipid, said suspension being maintained at a temperature below the phase transition temperature of the gaseous precursor, followed by autoclaving to move the temperature above the phase transition temperature, optionally with shaking, or permitting the gaseous precursor microspheres to form spontaneously, whereby the expanded gaseous precursor in the sealed vessel increases the pressure in said vessel, and cooling down the gas-filled microsphere suspension, after which shaking may also take place.

Freeze drying is useful to remove water and organic materials from the stabilizing compounds prior to the shaking gas instillation method. Drying-gas instillation methods may be used to remove water from microspheres. By pre-entrapping the gaseous precursor in the dried microspheres (i.e. prior to drying) after warming, the gaseous precursor may expand to fill the microsphere. Gaseous precursors can also be used to fill dried microspheres after they have been subjected to vacuum. As the dried microspheres are kept at a temperature below their gel state to liquid crystalline temperature, the drying chamber can be slowly filled with the gaseous precursor in its gaseous state, e.g. perfluorobutane can be used to fill dried microspheres composed of dipalmitoylphosphatidylcholine (DPPC) at temperatures between 4° C. (the boiling point of perfluorobutane) and below 40° C., the phase transition temperature of the biocompatible lipid. In this case, it would be most preferred to fill the microspheres at a temperature about 4° C. to about 5° C.

Preferred methods for preparing the temperature activated gaseous precursor filled microspheres comprise shaking an aqueous solution having a stabilizing compound such as a biocompatible lipid in the presence of a gaseous precursor at a temperature below the gel state to liquid crystalline state phase transition temperature of the lipid, and below the liquid state to gas state phase transition temperature of the gaseous precursor. Heating of the mixture to a temperature above the liquid state to gas state phase transition temperature of the gaseous precursor then causes the precursor to expand. Heating is then discontinued, and the temperature of the mixture is then allowed to drop below the liquid state to gas state phase transition temperature of the gaseous precursor. Shaking of the mixture may take place during the heating step, or subsequently after the mixture is allowed to cool.

The present invention also contemplates the use of a method for preparing gaseous precursor filled microspheres comprising shaking an aqueous solution comprising a stabilizing compound such as a biocompatible lipid in the presence of a gaseous precursor, and separating the resulting gas and gaseous precursor filled microspheres for topical or subcutaneous delivery of active ingredients. Microspheres prepared by the foregoing methods are referred to herein as gaseous precursor filled microspheres prepared by a gel state shaking gaseous precursor instillation method.

Conventional, aqueous-filled liposomes of the prior art are routinely formed at a temperature above the phase transition temperature of the lipids used to make them, since they are more flexible and thus useful in biological systems in the liquid crystalline state. See, for example, Szoka and Papahadjopoulos, *Proc. Natl. Acad. Sci.* 1978, 75, 4194–4198. In contrast, the microspheres made according to preferred embodiments described herein are gaseous precursor filled, which imparts greater flexibility, since gaseous precursors after gas formation are more compressible and compliant than an aqueous solution. Thus, the gaseous precursor filled microspheres may be utilized in biological systems when formed at a temperature below the phase transition temperature of the lipid, even though the gel phase is more rigid.

The methods contemplated by the present invention provide for agitating an aqueous solution comprising a stabilizing compound, such as a biocompatible lipid, in the presence of a temperature activated gaseous precursor. Shaking, as used herein, is defined as a motion that agitates an aqueous solution such that gaseous precursor is introduced from the local ambient environment into the aqueous solution. Any type of motion that agitates the aqueous solution and results in the introduction of gaseous precursor may be used for the shaking. The shaking must be of sufficient force to allow the formation of foam after a period of time. Preferably, the shaking is of sufficient force such that foam is formed within a short period of time, such as 30 minutes, and preferably within 20 minutes, and more preferably, within 10 minutes. The shaking may be by microemulsifying, by microfluidizing, for example, swirling, such as by vortexing, side-to-side, or up-and-down motion. In the case of the addition of gaseous precursor in the liquid state, sonication may be used in addition to the shaking methods set forth above. Further, different types of motion may be combined. Also, the shaking may occur by shaking the container holding the aqueous lipid solution, or by shaking the aqueous solution within the container without shaking the container itself. Further, the shaking may occur manually or by machine. Mechanical shakers that may be used include, for example, a shaker table, such as a VWR Scientific (Cerritos, Calif.) shaker table, a microfluidizer, Wig-L-Bug™ (Crescent Dental Manufacturing, Inc., Lyons, Ill.), which has been found to give particularly good results, and a mechanical paint mixer, as well as other known machines. Another means for producing shaking includes the action of gaseous precursor emitted under high velocity or pressure. It will also be understood that preferably, with a larger volume of aqueous solution, the total amount of force will be correspondingly increased. Vigorous shaking is defined as at least about 60 shaking motions per minute, and is preferred. Vortexing at least 1000 revolutions per minute, an example of vigorous shaking, is more preferred. Vortexing at 1800 revolutions per minute is most preferred.

The formation of gaseous precursor filled microspheres upon shaking can be detected by the presence of a foam on the top of the aqueous solution. This is coupled with a decrease in the volume of the aqueous solution upon the formation of foam. Preferably, the final volume of the foam is at least about two times the initial volume of the aqueous lipid solution; more preferably, the final volume of the foam is at least about three times the initial volume of the aqueous solution; even more preferably, the final volume of the foam is at least about four times the initial volume of the aqueous solution; and most preferably, all of the aqueous lipid solution is converted to foam.

The required duration of shaking time may be determined by detection of the formation of foam. For example, 10 ml of lipid solution in a 50 ml centrifuge tube may be vortexed for approximately 15–20 minutes or until the viscosity of the gas and gaseous precursor filled microspheres becomes sufficiently thick so that it no longer clings to the side walls as it is swirled. At this time, the foam may cause the solution containing the gas and gaseous precursor filled microspheres to raise to a level of 30 to 35 ml.

The concentration of stabilizing compound, especially lipid required to form a preferred foam level will vary depending upon the type of stabilizing compound such as biocompatible lipid used, and may be readily determined by one skilled in the art, once armed with the present disclosure. For example, in preferred embodiments, the concentration of 1,2-dipalimitoylphosphatidylcholine (DPPC) used to form gas and gaseous precursor filled microspheres according to methods contemplated by the present invention is about 0.1 mg/ml to about 30 mg/ml saline solution. The concentration of distearoylphosphatidylcholine (DSPC) used in preferred embodiments is about 0.1 mg/ml to about 10 mg/ml saline solution.

Specifically, DPPC in a concentration of 20 mg/ml to 30 mg/ml, upon shaking, yields a total suspension and entrapped gaseous precursor volume four times greater than the suspension volume alone. DSPC in a concentration of 10 mg/ml, upon shaking, yields a total volume completely devoid of any liquid suspension volume and contains entirely foam.

It will be understood by one skilled in the art, once instructed by the present disclosure, that the lipids and other stabilizing compounds used as starting materials, or the microsphere final products, may be manipulated prior and subsequent to being subjected to the methods contemplated by the present invention. For example, the stabilizing compound such as a biocompatible lipid may be hydrated and then lyophilized, processed through freeze and thaw cycles, or simply hydrated. In preferred embodiments, the lipid is hydrated and then lyophilized, or hydrated, then processed through freeze and thaw cycles and then lyophilized, prior to the formation of gas and gaseous precursor filled microspheres. According to the methods contemplated by the present invention, the presence of gas, such as and not limited to air, may also be provided by the local ambient atmosphere. The local ambient atmosphere may be the atmosphere within a sealed container, or in an unsealed container, may be the external environment. Alternatively, for example, a gas may be injected into or otherwise added to the container having the aqueous lipid solution or into the aqueous lipid solution itself in order to provide a gas other than air. Gases that are not heavier than air may be added to a sealed container while gases heavier than air may be added to a sealed or an unsealed container. Accordingly, the present invention includes co-entrapment of air and/or other gases along with gaseous precursors.

As already described above in the section dealing with the stabilizing compound, the preferred methods contemplated by the present invention are carried out at a temperature below the gel state to liquid crystalline state phase transition temperature of the lipid employed. By "gel state to liquid crystalline state phase transition temperature", it is meant the temperature at which a lipid bilayer will convert from a gel state to a liquid crystalline state. See, for example, Chapman et al., *J. Biol. Chem.* 1974, 249, 2512–2521.

Hence, the stabilized microsphere precursors described above, can be used in the same manner as the other stabilized microspheres used in the present invention, once activated by application to the tissues of a patient, where such factors as temperature or pH may be used to cause generation of the gas. It is preferred that this embodiment is one wherein the gaseous precursors undergo phase transitions from liquid to gaseous states at near the normal body temperature of said patient, and are thereby activated by the temperature of said patient tissues so as to undergo transition to the gaseous phase therein. More preferably still, this method is one wherein the patient tissue is human tissue having a normal temperature of about 37° C., and wherein the gaseous precursors undergo phase transitions from liquid to gaseous states near 37° C.

All of the above embodiments involving preparations of the stabilized gas and gaseous precursor filled microspheres used in the present invention, may be sterilized by autoclave or sterile filtration if these processes are performed before either the gas instillation step or prior to temperature mediated gas conversion of the temperature sensitive gaseous precursors within the suspension. Alternatively, one or more anti-bactericidal agents and/or preservatives may be included in the formulation of the stabilized foam, such as sodium benzoate, all quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, will be necessary where the stabilized foam of microspheres is used for topical delivery under what would be characterized as invasive circumstances. The appropriate means of sterilization will be apparent to the artisan instructed by the present description of the stabilized gas and gaseous precursor filled microspheres and their use. The stabilized foam is generally stored as an aqueous suspension but in the case of dried microspheres or dried lipidic spheres the stabilized foam may be stored as a dried powder ready to be reconstituted prior to use.

The stabilized foams comprising the microspheres of the present invention should be prepared from as impermeable a material as possible, given the other requirements set forth herein. An impermeable material is one that does not permit the passage of a substantial amount of the contents of the microsphere in typical storage conditions or in use before induced release occurs, usually by the pressure and friction attendant the action of the patient in rubbing the foam into his or her skin. Substantial as used in connection with impermeability is defined as greater than about 50% of the contents, the contents being both the gas and the active agent. Preferably, no more than about 25%, more preferably no more than about 10%, and most preferably no more than about 1% of the gas and active agent are released. The temperature of storage is preferably below the phase transition temperature of the material forming the microspheres.

The stability of the gas and gaseous precursor filled microspheres of the invention is of significant practical importance; they tend to have greater stability during storage than other gas and gaseous precursor filled microspheres produced via known procedures such as pressurization or other techniques. At 72 hours after formation, for example, conventionally prepared gas-containing microspheres often are essentially devoid of gas, the gas having diffused out of the microspheres and/or the microspheres having ruptured and/or fused. In comparison, active ingredient containing gas and gaseous precursor filled, polar microspheres of the present invention generally have a shelf life stability of greater than about three weeks, often greater than three months or even much longer, such as over twelve months or even two years.

The stabilized foams of the present invention, prepared from the materials and in accordance with the methods described above, have a very creamy consistency which is ideal for coating a selected tissue. The stabilized foam has a smooth velvety feel. Moreover, the stabilized foams of the present invention have unusual properties which enable them to act as potentiation vehicles to facilitate application of active ingredients such as therapeutic agents and cosmetics to a selected tissue, and to promote absorption of those active ingredients by a selected tissue.

The present invention is further demonstrated in the following examples, which illustrate the preparation and testing of the stabilized foams comprising gas and gaseous precursor filled microspheres. In the following examples, Examples 1–6, 11, 13, 14, 17, 18, 26–30, 32 and 33 were actually carried out. The remaining examples are prophetic. These examples are not in any way intended to limit the scope of the present invention.

EXAMPLE OF PREFERRED EMBODIMENTS

Example 1

Preparation of Gas and Gaseous Precursor Filled Microspheres

Fifty mg of 1,2-dipalmitoyl-sn-glycero-3-phosphocholine (MW: 734.05, powder, Lot No. 160pc-183) (Avanti-Polar Lipids, Alabaster, Ala.) is weighed and hydrated with 5.0 ml of saline solution (0.9% NaCl) or phosphate buffered saline (0.8% sodium chloride, 0.02% potassium chloride, 0.115% dibasic sodium phosphate and 0.2% monobasic potassium phosphate, pH adjusted to 7.4) in a centrifuge tube. The hydrated suspension is then shaken on a vortex machine (Scientific Industries, Bohemia, N.Y.) for 10 minutes at an instrument setting of 6.5. A total volume of 12 ml should then noted. The saline solution should decrease from 5.0 ml to about 4 ml.

The gas and gaseous precursor filled microspheres made by the method described above can then be sized by optical microscopy. It should be determined that the largest size of the microspheres ranges from about 50 to about 60 μm and the smallest size detected should be about 8 μm. The average size should range from about 15 to 20 μm.

The gas and gaseous precursor filled microspheres are then filtered through an 8, 10 or 12 μm "NUCLEPORE" membrane using a Swin-Lok Filter Holder, (Nuclepore Filtration Products, Costar Corp., Cambridge, Mass.) and a 20 cc syringe (Becton Dickinson & Co., Rutherford, N.J.). The membrane is a 10 or 12 μm "NUCLEPORE" membrane (Nuclepore Filtration Products, Costar Corp., Cambridge, Mass.). The 10.0 μm filter is placed in the Swin-Lok Filter Holder and the cap tightened down securely. The lipid-based microsphere solution is shaken up and it is transferred to the 20 cc syringe via an 18 gauge needle. Approximately 12 ml of gas filled foam solution is placed in the syringe, and the syringe is screwed onto the Swin-Lok Filter Holder. The syringe and the filter holder assembly are inverted so that the larger of the gas and gaseous precursor filled microspheres can rise to the top. Then the syringe is gently pushed up and the gas and gaseous precursor filled microspheres are filtered in this manner.

The survival rate (the amount of the gas and gaseous precursor filled microspheres that are retained after the extrusion process) of the gas and gaseous precursor filled microspheres after the extrusion through the 10.0 µm filter is about 83–92%. Before hand extrusion, the volume of foam is about 12 ml and the volume of aqueous solution is about 4 ml. After hand extrusion, the volume of foam is about 10–11 ml and the volume of aqueous solution is about 4 ml.

The optical microscope is used again to determine the size distribution of the extruded gas and gaseous precursor filled microspheres. It is determined that the largest size of the microspheres ranges from about 25 to about 30 µm and the smallest size detected is about 5 µm. The average size ranges from about 8 to about 15 µm.

It is found that after filtering, greater than 90% of the gas and gaseous precursor filled microspheres are smaller than 15 µm.

Example 2

Preparation of Gas and Gaseous Precursor Filled Microspheres Incorporating Lyophilization Fifty mg of 1,2-dipalmitoyl-sn-glycero-3-phosphocholine, (MW: 734.05, powder) (Avanti-Polar Lipids, Alabaster, Ala.) is weighed and placed into a centrifuge tube. The lipid is then hydrated with 5.0 ml of saline solution (0.9% NaCl). The lipid suspension is then vortexed for 10 minutes at an instrument setting of 6.5. After vortexing, the entire solution is frozen in liquid nitrogen. Then the sample is put on the lyophilizer for freeze drying; the sample is kept on the lyophilizer for 18 hours. The dried lipid is taken off the lyophilizer and rehydrated in 5 ml of saline solution and vortexed for ten minutes at a setting of 6.5. A small sample of this solution is pipetted onto a slide and the solution is viewed under a microscope. The size of the gas and gaseous precursor filled microspheres is then determined. It is determined that the largest size of the microspheres is about 60 µm and the smallest size detected is about 20 µm. The average size ranges from about 30 to 40 µm.

Example 3

Example of the Inability to Prepare a Gas and Gaseous Precursor Filled Microsphere Preparation Above The Phase Transition Temperature of the Lipid Fifty mg of 1,2-dipalmitoyl-sn-glycero-3-phosphocholine, (MW: 734.05, powder) (Avanti-Polar Lipids, Alabaster, Ala.) is weighed and placed into a centrifuge tube. Approximately two feet of latex tubing (0.25 in. inner diameter) is wrapped around a conical centrifuge tube in a coil like fashion. The latex tubing is then fastened down to the centrifuge tube with electrical tape. The latex tubing is then connected to a constant temperature circulation bath (VWR Scientific Model 1131). The temperature of the bath is set to 60° C. and the circulation of water is set to high speed to circulate through the tubing. A thermometer is placed in the lipid solution and found to be between 42° and 50° C.

The lipid suspension is vortexed for a period of 10 minutes at vortex instrument setting of 6.5. It is noted that very little foaming of the lipid (phase transition temp.=41° C.) takes place and that it does not appreciably form gas and gaseous precursor filled microspheres. Optical microscopy reveals large lipidic particles in the solution. The number of gas and gaseous precursor filled microspheres that forms at this temperature is less than 3% of the number that form at a temperature below the phase transition temperature. The suspension is allowed to sit for 15 minutes until the suspension temperature equilibrated to room temperature (25° C.). The suspension is then vortexed for a duration of 10 minutes. After 10 minutes, it is noted that gas and gaseous precursor filled microspheres form.

The above demonstrates the necessity of performing the vortexing with the lipid in the gel state in order to make stable foams.

Example 4

Preparation of Gas and Gaseous Precursor Filled Microspheres Incorporating a Freeze-Thaw Procedure Fifty mg of 1,2-dipalmitoyl-sn-glycero-3-phosphocholine, (MW: 734.05, powder) (Avanti-Polar Lipids, Alabaster, Ala.) is placed into a centrifuge tube. The lipid is then hydrated with 5.0 ml of 0.9% NaCl added. The aqueous lipid suspension is vortexed for 10 minutes at an instrument setting of 6.5. After vortexing, the entire suspension is then heated in a water bath at a temperature of about 45° C. followed by freezing. The heating and freezing (freeze-thaw) procedure is then repeated eight times. The hydrated suspension is then vortexed for 10 minutes at an instrument setting of 6.5. Gas and gaseous precursor filled microspheres are then detected as described in Example 1.

Example 5

Preparation of Gas and Gaseous Precursor Filled Microspheres Using a Solvent Mixture of Aqueous Buffer and Propylene Glycol Ten mg of 1,2-dipalmitoyl-sn-glycero-3-phosphocholine, (MW: 734.05, powder) (Avanti-Polar Lipids, Alabaster, Ala.) is placed into a centrifuge tube. The lipid is then hydrated with a mixture of 0.9% NaCl and propylene glycol (9:1 or 7:1, v:v) (Spectrum Chemical Mfg. Corp., Gardena, Calif.). The aqueous lipid suspension is vortexed for 10 minutes at an instrument setting of 6.5. The gas and gaseous precursor filled microspheres which form are then sized on an Accusizer Model 770 optical sizer (Particle Sizing Systems, Santa Barbara, Calif.) where the median size $\leq 10$ µm.

Experiments using other propylene glycol suspensions to prepare the gas and gaseous precursor filled microspheres will indicate that the foam has a smaller mean diameter and appears to be more stable than without propylene glycol. The foam height (foam volume) per milligram lipid is larger with, than without propylene glycol. An additional benefit of using the propylene glycol is that it may improve a selected tissue penetration enhancing properties of the lipid-based foam for cosmetics and dermal drug delivery purposes.

Example 6

Preparation of Vitamin E Encapsulated Gas and Gaseous Precursor Filled Microspheres The same preparation as in Example 1 is made except that prior to vortexing, 100 mg Vitamin E acetate, U.S.P./N.F. (212 µmoles, Spectrum Chemical Mfg. Corp., Gardena, Calif.) is added followed by vigorous vortexing. This yields an identical volume of foam; however, now containing Vitamin E.

Example 7

Preparation of Vitamin $D_2$ or $D_3$ Encapsulated Gas and Gaseous Precursor Filled Microspheres The same preparation as in Example 1 is made except that prior to vortexing, 100 mg Vitamin $D_2$ (Ergocalciferol), U.S.P./N.F.(252 µmoles, Spectrum Chemical Mfg. Corp., Gardena, Calif.) or 100 mg Vitamin D3 (cholecalciferol), U.S.P./N.F. (260 µmoles, Spectrum Chemical Mfg. Corp., Gardena, Calif.) is added followed by vigorous vortexing. This yields an identical volume of foam; however, now containing Vitamin $D_2$ or $D_3$ respectively.

Example 8
Preparation of Vitamin A Encapsulated Gas and Gaseous Precursor Filled Microspheres The same preparation as in Example 1 is made except that prior to vortexing, 100 mg Vitamin A (Retinyl Acetate), U.S.P./N.F.(304 µmoles, Spectrum Chemical Mfg. Corp., Gardena, Calf.) is added followed by vigorous vortexing. This yields an identical volume of foam; however, now containing Vitamin A.

Example 9
Preparation of a Gas and Gaseous Precursor Filled Microsphere Cream for Topical Delivery Gas and gaseous precursor filled microspheres are prepared according to the methods described in copending application U.S. Ser. No. 717,084 and U.S. Ser. No. 717,899, both of which were filed on Jun. 18, 1991.

To a small mixing bowl is added 60 mL of gas and gaseous precursor filled microspheres and 10 mL of glycerin. The mixture is then gently folded together along with 2 grams of lanolin. This mixture is set aside. In a separate container is then added 2 grams of cetyl alcohol and 1 gram of cholesterol base. To this is then added 2 grams of sodium carbomer 941 and the mixture once again folded together. To this mixture is then added 50 mg methylparaben, 50 mg propylparaben, and 50 mg Quaternium 15 previously dissolved in 1 mL of ethanol. The second mixture is then levigated to uniformity and the two mixtures are added together and once again folded. To this mixture is then added 120 grams of hydrophilic ointment and the entire contents are folded together to yield a smooth, creamy, emollient.

Example 10
Preparation of Gas and Gaseous Precursor Filled Microspheres in a Mixed Vehicle Ten mg of 1,2-dipalmitoyl-sn-glycero-3-phosphocholine (Avanti Polar Lipids, Alabaster, Ala.) is placed in a centrifuge tube. The lipid is then hydrated with a mixture of 0.9% aqueous sodium chloride, glycerol, and propylene glycol (8:1:1, v:v:v) (Spectrum Chemical Co., Gardena, Calif.). The suspension is vortexed for 10 minutes on an instrument setting of 6.5. The resultant gas and gaseous precursor filled lipid bilayers are then sized on an Accusizer Model 770 optical sizer (Particle Sizing Systems, Santa Barbara, Calif.) where the median size is approximately 10 µm. The total foam and liquid volume will increase to approximately 35 mLs.

Example 11
Preparation of Gas and Gaseous Precursor Filled Microspheres with Essentially No Aqueous Residual Volume The same procedure as in Example 10 is utilized except that 25 mg $mL^{-1}$ to 50 mg $mL^{-1}$ of lipid is used. Upon vortexing, there is formed approximately 45 mL to 50 mL of foam volume, and significantly, the formulation is essentially devoid of residual liquid.

Example 12
Preparation of Gas and Gaseous Precursor Filled Microspheres with Cholesterol Sulfate The formulation as described in Example 10 is utilized except that 1–5 mole % cholesterol sulfate (Sigma, St. Louis, Mo.) is added. The suspension is then vortexed to yield a foam similar to that described in Example 10.

Example 13
Preparation of Gas and Gaseous Precursor Filled Microspheres with PEGylated Lipid The formulation prepared in accordance with Example 10 is utilized except that 1–5 mole % of 1,2 dipamitoyl-sn-glycero-3-phosphoethanolamine-N-[poly(ethylene glycol) 5000] (purity 99%, Avanti Polar Lipids, Alabaster, Ala.) is included in the formulation. The suspension is then vortexed as described in Example 10 to yield a foam similar to that described in Example 10.

Example 14
Preparation of Gas and Gaseous Precursor Filled Microspheres with Phosphatidic Acid The formulation prepared as described in Example 10 is utilized except that 1–5 mole % of phosphatidic acid (purity 99%, Avanti Polar Lipids, Alabaster, Ala.) is included in the formulation. The suspension is then vortexed as described in example 10 to yield a foam similar to that described in Example 10.

Example 15
Preparation of Gas and Gaseous Precursor Filled Microspheres with 1,2 Dipamitoyl-sn-Glycero-3-Phosphatidylglycerol (DPPG)

The formulation prepared as described in Example 10 is utilized except that 1–10 mole % of 1,2 dipamitoyl-sn-glycero-3-phosphatidylglycerol (DPPG) (purity 99%, Avanti Polar Lipids, Alabaster, Ala.) is included in the formulation. The suspension is then vortexed as described in Example 10 to yield a foam similar to that described in Example 10.

Example 16
Preparation of Gas and Gaseous Precursor Filled Microspheres with 1,2 Dipamitoyl-sn-Glycero-3-Phosphatidylglycerol (DPPG) and Phosphatidic Acid The formulation as prepared described in Example 10 is utilized except that 1–10 mole % of 1,2 dipamitoyl-sn-glycero-3-phosphatidylglycerol (DPPG) (purity 99%, Avanti Polar Lipids, Alabaster, Ala.) and 1–5 mole % of phosphatidic acid (purity 99%, Avanti Polar Lipids, Alabaster, Ala.) is included in the formulation. The suspension is then vortexed as described in Example 10 to yield a foam similar to that described in Example 10.

Example 17
Preparation of Gas and Gaseous Precursor Filled Microspheres with a Water Soluble Vitamin (Ascorbic Acid)

The formulation prepared as described in Example 10 is utilized except that 0.5–5.0 mole % of Ascorbic Acid (USP-FCC Roche Vitamins and Fine Chemicals, Nutley, N.J.) is included in the formulation. The suspension is then vortexed as described in Example 10 to yield a rather creamy foam similar to that described in Example 10. A similar formulation is made with argon, nitrogen, and neon gases with similar results.

Example 18
Preparation of Gas and Gaseous Precursor Filled Microspheres with a Water Soluble Vitamin (Ascorbic Acid)

The formulation prepared as described in Example 10 is utilized except that 5.0–50.0 mole % of Ascorbic Acid (USP-FCC Roche Vitamins and Fine Chemicals, Nutley, N.J.) is included in the formulation. The suspension is then vortexed as described in Example 10 to yield a rather creamy foam similar to that described in Example 10. A similar formulation is made with argon, nitrogen, and neon gases with similar results.

Example 19
Preparation of Gas and Gaseous Precursor Filled Microspheres From a pH Sensitive Gaseous Precursor Egg phosphatidyl choline, 1 gram, is suspended in 100 cc of physiological saline at room temperature to form a dispersion of multilamellar microsphere vesicles. The microspheres are then placed in the vessel to which is added sodium bicarbonate (Mallinckrodt, St. Louis Mo.) and an ionophore (A231 87) resulting in bicarbonate encapsulated microspheres contacting that ionophore. Acid is added to the external aqueous phase in order to lower the pH within the vesicles. The bicarbonate entrapped within the vesicles is found to form $CO_2$ gas and water.

Example 20
Preparation of Gas and Gaseous Precursor Filled Microspheres From a Temperature Sensitive Gaseous Precursor Gas and gaseous precursor filled microspheres are prepared as in Example 1 except that the gaseous precursor 2-methyl-2-butene is added. The subsequent emulsion/ suspension is then filtered through a Nuclepore (Costar, Pleasanton, Calif.) 0.22 µm membrane at room temperature (20° C.). Upon raising of the temperature to approximately 39° C., gas bubbles are noted to form, yielding gas and gaseous precursor filled microspheres.

Example 21
Preparation of Gas and Gaseous Precursor Filled Microspheres Activated by Light Gas and gaseous precursor filled microspheres are prepared as in Example 1 except for the addition of a photosensitive diazonium compound. The sample is filtered through a Nucleopore (Costar, Pleasanton, Calif.) 0.22 µm membrane at room temperature (20° C.). Upon shining of light on the sample, it is noted that gas bubble formation commences, yielding gas and gaseous precursor filled microspheres.

Example 22
Preparation of Gas and Gaseous Precursor Filled Microspheres Incorporating Chelates for the Management of Psoriasis Gas and gaseous precursor filled microspheres are prepared as described in Example 1, except 250 mg of Penicillamine (Bachem, Gardena, Calif.) is added to the lipid suspension. The suspension is then microfluidized as per Example 1 to yield gas and gaseous precursor filled microspheres with Penicillamine encapsulated. This mixture is applied to a selected tissue to absorb excess copper ions, thereby managing a psoriatic lesion.

Example 23
Preparation of Gas and Gaseous Precursor Filled Microspheres Incorporating Chelates for the Management of Wilson's Disease Gas and gaseous precursor filled microspheres are prepared as described in Example 1, except 250 mg of the lipophilic chelate EDTA-EOEA-DP is added to the lipid suspension. The suspension is then microfluidized as per Example 1 to yield gas and gaseous precursor filled microspheres with Penicillamine encapsulated. This mixture is applied to a selected tissue to absorb excess copper ions, thereby managing the excess and offending copper ion.

Example 24
Preparation of Gas and Gaseous Precursor Filled Microspheres Incorporating Liposoluble Compounds for the Management of Wilson's Disease Gas and gaseous precursor filled microspheres are prepared as described in Example 1, except 250 mg of Penicillamine (Bachem, Gardena, Calif.) is added to the lipid suspension. The suspension is then microfluidized as per Example 1 to yield gas and gaseous precursor filled microspheres with Penicillamine encapsulated. This mixture is applied to a selected tissue to absorb excess copper ions, thereby managing the excess and offending copper ion.

Example 25
Preparation of Gas and Gaseous Precursor Filled Microspheres Incorporating Liposoluble Compounds for the Management of Wilson's Disease Gas and gaseous precursor filled microspheres are prepared as described in Example 1, except 250 mg of desferrioxamine (Aldrich Chemical Co, Milwaukee, Wis.) is added to the lipid suspension. The suspension is then microfluidized as per Example 1 to yield gas and gaseous precursor filled microspheres with Penicillamine encapsulated. This mixture is applied to a selected tissue to absorb excess copper ions, thereby managing the excess and offending copper ion.

Example 26
Preparation of a Soap Comprising Gas and Gaseous Precursor Filled Microspheres with Essentially No Aqueous Residual Volume The same procedure as in Example 10 is utilized except that 25 mg $mL^{-1}$ to 50 mg $mL^{-1}$ of lipid is used. To the formula is added between 250 mg and 1 g of xanthan gum (Kelco, San Diego, Calif.) and between 250 mg and 2 g of Duponol C (sodium dodecyl sulfate, Witco, Houston, Tex.). The mixture is vortexed for from 10 to 20 seconds to yield a creamy foam, which upon application to a selected tissue, gives a sensation of softness and creaminess, but which, upon application of water, readily forms a soapy lather.

Example 27
Formation of Perfluoropropane Gas-filled Microspheres with Lipid Bilayers Microspheres comprising gas-filled lipid bilayers are prepared in two 20 mL vials with 6 mLs of a diluent containing normal (physiological) saline: propylene glycol:glycerol (8:1:1, v:v:v). To this is added in a final concentration of lipid varying between 0.25 mg $mL^{-1}$ and a maximum of 50 mg $mL^{-1}$, a mixture of dipalmitoylphosphatidylcholine (DPPC):phosphatidic acid:dipalmitoylphosphatidylethanolamine-PEG 5000 in a weight ratio of 82:10:8, (w:w:w). The samples are then sealed with airtight and pressure maintaining septum caps. They are then purged and evacuated at least three times with perfluoropropane gas (99.99%, Scott Medical Gases, Plumbsteadville, Pa.). The samples are then either autoclaved for 15 minutes at 121° C. in a Barnstead Model C57835 Steam Sterilizer (Barnstead/Thermolyne Corporation, Dubuque, Iowa) or sterile filtered from one to three times through a Nuclepore 0.22 m filter (Costar, Pleasanton, Calif.). The samples are then removed from the autoclave and allowed to cool to approximately 40° C. The samples are thereafter vortexed on a Wig-L-Bug vortexer (Crescent Dental Mfg. Co., Lyons, Ill.) for a duration of two minutes. The resultant mixtures are significant for the formation of gas-filled microspheres which resembled a foam. The microspheres comprising gas-filled lipid bilayers are then sized by three methods on a Particle Sizing Systems Model 770 light obscuration detector (Particle Sizing Systems, Santa Barbara, Calif.); a Reichert-Jung Model 150 Optical Microscope equipped with a calibration eyepiece (Cambridge Instruments, Buffalo, N.Y.); and a Coulter Model (Coulter Industries, Luton Beds, England). Samples display an average number weighted size of approximately 5–7μ, with at least 95% of the particles smaller than 10μ.

Example 28
Formation of Perfluorobutane Microspheres Comprising Gas-filled Lipid Bilayers The same procedure as in Example 27 is utilized except that perfluoropropane is replaced with identical volumes of perfluorobutane (97+% purity, Flura Corporation, Nashville Tenn.). This yields perfluorobutane gas-filled microspheres of essentially the same dimensions.

Example 29
Formation of Microspheres Comprising Perfluoropentane Gas-Filled Lipid Bilayers The same procedure as in Example 27 is utilized except that perfluoropropane is replaced with approximately 100 μL of perfluoropentane (Flura Corp., Nashville, Tenn.) and air. Foam similar to that described in the Example 27 is observed.

Example 30
Formation of Microspheres Comprising Perfluoroethane Gas-Filled Lipid Bilayers The same procedure as in Example 27 is utilized except that perfluoropropane is replaced with an identical volume of perfluoroethane (Canadian Liquid Air, Ltd., Montreal, Canada). Foam similar to that described in the Example 27 is observed.

Example 31
Preparation of Progesterone Encapsulated Perfluoropropane Gas-Filled Microspheres The same procedure as in Example 27 is utilized except that 4 mg of progesterone is added to the formulation. Foam similar to that described in Example 27 is observed. Two (2) mLs of the mixture, shaken prior to drawing into a syringe, is then drawn and injected subcutaneously on the volar surface of the forearm of a human (gender female) volunteer. The subcutaneous administration is repeated once every two to six months.

Example 32
Preparation of Gas-Filled Microspheres With An Antioxidant and Oxygen Scavenger To a 50 mL vortex vial is added 4.4 mL of a 27.2 weight % aqueous mixture of ascorbic acid (Vitamin C, Spectrum Pharmaceutical, Gardena, Calif.) (an antioxidant). To this is added 100 μL of a solution containing 55,000 units of glucose oxidase (Sigma Chemicals, St. Louis, Mo.) (an oxygen scavenger) and 4125 units of catalase (Sigma Chemical, St. Louis, Mo.). To this solution is then added 500 μL of a 5% (wt:vol) aqueous solution of dextrose (Spectrum Pharmaceutical, Gardena, Calif.). The resulting mixture is purged with nitrogen gas and 500 mg of dry distearoylphosphatidylchloine (Avanti Polar Lipids, Alabaster, Ala.) is added. The resulting formulation is then purged with a nitrogen blanket. Next one mL of a 1% aqueous cetyl alcohol solution is added, purged again with nitrogen, and finally vortexed on a vortex mixer (VWR Scientific, Cerritos, Calif.) for 15 minutes to yield a thick, creamy white, foam of gas-filled microspheres.

Example 33
Preparation of Gas-Filled Microspheres With An Antioxidant and Oxygen Scavenger To a 50 mL vortex vial is added 4.4 mL of a 22.5 weight % aqueous mixture of ascorbic acid (Vitamin C, Spectrum Pharmaceutical, Gardena, Calif.) (an antioxidant). To this is added 100 μL of a solution containing 55,000 units of glucose oxidase (Sigma Chemicals, St. Louis, Mo.) (an oxygen scavenger) and 4125 units of catalase (Sigma Chemical, St. Louis, Mo.). To this solution is then added 500 μL of a 5% (wt:vol) aqueous solution of dextrose (Spectrum Pharmaceutical, Gardena, Calif.). The resulting mixture is purged with nitrogen gas and 500 mg of dry distearoylphosphatidylchloine (Avanti Polar Lipids, Alabaster, Ala.) is added. The resulting formulation is then purged with a perfluorobutane blanket (Flura Corporation, Newport, Tenn.), and is vortexed on a vortex mixer (VWR Scientific, Cerritos, Calif.) for 15 minutes to yield a thick, creamy white, foam of gas-filled microspheres.

The disclosures of each patent, patent application and publication cited or described in this document are hereby incorporated herein by reference, in their entirety.

Various modification of the invention, in addition to those described herein, will be apparent to those skilled in the art from the foregoing description. Such modifications are also intended to fall within the scope of the appended claims.

What is claimed is:

1. A composition comprising a gas filled lipid-containing microsphere comprising at least about 50% gas in the interior thereof and an effective amount of a therapeutic agent or a cosmetic for topical or subcutaneous application to a selected tissue of a patient, wherein said therapeutic agent is selected from the group consisting of anti-fungal agents, hormones, vitamins, peptides, enzymes, anti-allergic agents, anti-coagulation agents, antituberculars, antivirals, antibiotics, antibacterials, antiinflammatory agents, antiprotozoans, local anesthetics, growth factors, cardiovascular agents, diuretics, and radioactive compounds.

2. A composition according to claim 1 wherein the therapeutic agent is selected from the group consisting of scopolamine, nicotine, methylnicotinate, mechlorisone dibutyrate, naloxone, methanol, caffeine, salicylic acid, and 4-cyanophenol.

3. A composition according to claim 1 wherein anti-fungal agents are selected from the group consisting of ketoconazole, nystatin, griseofulvin, flucytosine, miconazole, and amphotericin B; wherein the hormones are selected from the group consisting of growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide and fludrocortisone acetate; wherein the vitamins are selected from the group consisting of cyanocobalamin neinoic acid, retinoids, retinol palmitate, ascorbic acid, and α-tocopherol; wherein the peptides and enzymes are selected from the group consisting of manganese super oxide dismutase and alkaline phosphatase; wherein the anti-allergic agent is amelexanox; wherein the anti-coagulation agents are selected from the group consisting of phenprocoumon and heparin; wherein the antituberculars are selected from the group consisting of paraminosalicylic acid, isoniazid, capreomycin sulfate cycloserine, ethambutol hydrochloride ethionamnide, pyrazinamide, rifampin, and streptomycin sulfate; wherein the antivirals are selected from the group consisting of acyclovir, amantadine azidothymidine, ribavirin and vidarabine monohydrate; wherein the antibiotics are selected from the group consisting of dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin rifampin and tetracycline; wherein the antiinflammatories are selected from the group consisting of diflunisal, ibuprofen, indomethacin, meclofenamate, mefenamic acid, naproxen, oxyphenbutazone, phenylbutazone, piroxicam, sulindac, tolmetin, aspirin and salicylates; wherein the antiprotozoans are selected from the group consisting of chloroquine, hydroxychloroquine, metronidazole, quinine and meglumine antimonate; wherein the local anesthetics are selected from the group consisting of bupivacaine hydrochloride, chloroprocaine hydrochloride, etidocaine hydrochloride, lidocaine hydrochloride, mepivacaine hydrochloride, procaine hydrochloride and tetracaine hydrochloride; wherein the growth factors are selected from the group consisting of Epidermal Growth Factor, acidic Fibroblast Growth Factor, Basic Fibroblast Growth Factor, Insulin-Like Growth Factors, Nerve Growth Factor, Platelet-Derived Growth Factor, Stem Cell Factor, Transforming Growth Factor of the $\alpha$ family and Transforming Growth Factor of the $\beta$ family; wherein the cardiovascular agents are selected from the group consisting of clonidine, propranolol, lidocaine, nicardipine and nitroglycerin; wherein the diuretics are selected from the group consisting of mannitol and urea; and wherein the radioactive particles are selected from the group consisting of strontium, iodine, rhenium and yttrium.

4. A composition according to claim 1 wherein said therapeutic agent is selected from the group consisting of:
 (1) peptides selected from the group consisting of melanin concentrating hormone, melanin stimulating hormone, trypsin inhibitor, Bowman Burk inhibitor, luteinizing hormone releasing hormone, bombesin, cholecystokinin, insulin, gastrin, endorphins, enkephalins, growth hormone, prolactin, oxytocin, follicle stimulating hormone, human chorionic gonadotropin, corticotropin, $\beta$-lipotropin, $\gamma$-lipotropin, calcitonin, glucagon, thyrotropin, elastin, cyclosporin, and collagen;
 (2) monoclonal antibodies;
 (3) factors selected from the group consisting of hyaluronic acid, heparin, mad heparin sulfate;
 (4) anti-sense peptides and anti-sense oligonucleotides selected from the group consisting of an antisense oligonucleotide capable of binding the DNA encoding at least a portion of Ras, an antisense oligonucleotide capable of binding the DNA encoding at least a portion of basic fibroblast growth factor, and the antisense ras/p53 peptide;
 (5) immunosuppressants and anti-inflammatory agents;
 (6) chelants and chelating agents selected from the group consisting of penicillamine, citrate, ascorbate, diethylenetriaminepentaacetic acid, dihydroxypropylethylenediamine, cyclohexanediaminetetraacetic acid, ethylenediaminetetraacetic acid, ethylene glycol-bis($\beta$-aminoethyl ether)N,N,N',N',-tetraacetic acid, etidronic acid, dimethylsulfoxide, dipyridoxylethylenediaminediacetate-bisphosphate, N,N'-(1,2-ethanediylbis(oxy-2,1-phenylene))bis(N-(carboxymethyl), aminophenoltriacetic acid, tetrakis(2-pyridylmethyl)ethylenediamine, cyanins, and salts thereof; and
 (7) DNA encoding at least a portion of the following genes: HLA, dystrophin, CFTR, interleukin-2, tumor necrosis factor, adenosine deaminase, HDL receptor, thymidine kinase, HLA-B7, interleukin-4, melanocyte stimulating hormone gene, and melanin concentrating hormone gene.

5. A composition according to claim 1 wherein the cosmetic is selected from the group consisting of Vitamin A, Vitamin C, Vitamin D, Vitamin E, Vitamin K, beta carotene, collagen, elastin, retinoic acid, aloe vera, lanolin, hyaluronic acid, and nucleosides.

6. A composition according to claim 1 wherein said cosmetic is a sunscreen agent, said sunscreen agent selected from the group consisting of 5% isobutyl-p-aminobenzoate, 5% diallyl trioleate, 2.5% monoglyceryl p-aminobenzoate, 4% propylene glycol p-aminobenzoate, and a composition comprising 2% benzyl salicylate and 2% benzyl cinnamate.

7. A composition according to claim 1 comprising a cosmetic wherein said composition takes the form of a cosmetic cream, ointment, lotion, skin softener, gel, blush, eye-liner, mascara, acne-medication, cold cream, cleansing cream, or oleaginous foam.

8. A composition according to claim 1 further comprising one or more compounds selected from the following:
 (1) bacteriostatic agents selected from the group consisting of benzalkonium chloride, benzethonium chloride, benzoic acid, benzyl alcohol, butylparaben, cetylpyridinium chloride, chlorobutanol, chlorocresol, methylparaben, phenol, potassium benzoate, potassium sorbate, sodium benzoate and sorbic acid;
 (2) antioxidants selected from the group consisting of tocopherol, ascorbic acid and ascorbyl palmitate;
 (3) preservatives selected from the group consisting of parabens, quaternary ammonium compounds, alcohols, phenols, and essential oils;
 (4) buffers and neutralizers;
 (5) moisture content control agents and humectants;
 (6) ointment bases selected from the group consisting of lanolin, lanolin anhydrous, hydrophilic ointment, white ointment, yellow ointment, polyethylene glycol ointment, petrolatum, hydrophilic petrolatum, white petrolatum, rose water ointment, and squalene;
 (7) suspending and viscosity-increasing agents selected from the group consisting of acacia, agar, alginic acid, aluminum monostearate, bentonite, purified bentonite, magma bentonite, carbomer 934P, carboxymethylcellulose calcium, carboxymethylcellulose sodium 12, carboxymethylcellulose sodium, carrageenan, microcrystalline cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, silicon dioxide, zinc oxide, sodium alginate tragacanth, and xanthan gum;
 (8) skin absorption enhancing agents selected from the group consisting of pyrrolidones, fatty acids, sulfoxides, amines, terpenoids, terpenes, surfactants, alcohols, urea, glycols, azone, n-alkanols, n-alkanes, orgelase, and alphaderm cream;

(9) bases selected from the group consisting of glycerol, propylene glycol, isopropyl myristate, urea in propylene glycol, ethanol and water, and polyethylene glycol;

(10) other agents selected from the group consisting of glycerin, hexylene glycol, sorbitol, propylene glycol, and calcium silicate;

(11) oleaginous vehicles;

(12) coloring agents; and

(13) foaming agents.

9. A composition according to claim 1 wherein the microsphere is prepared from at least one biocompatible lipid.

10. A composition according to claim 9 wherein the biocompatible lipid is selected from the group consisting of fatty acids, lysolipids, phosphatidylcholines, phosphatidylethanolamines, phosphatidylserines, phosphatidylglycerols, phosphatidylinositols, sphingolipids, glycolipids, glucolipids, sulfatides, glycosphingolipids, lipids bearing polymers, lipids bearing sulfonated monosaccharides, lipids bearing sulfonated disaccharides, lipids bearing sulfonated oligosaccharides, cholesterols, tocopherols, lipids with ether-linked fatty acids, lipids with ester-linked fatty acids, polymerized lipids, diacetyl phosphates, dicetyl phosphates, stearylamines, cardiolipin, phospholipids with fatty acids of 6–8 carbons in length, synthetic phospholipids with asymmetric acyl chains, ceramides, non-ionic lipids, sterol aliphatic acid esters, sterol esters of sugar acids, esters of sugar acids, esters of sugar alcohols, esters of sugars, esters of aliphatic acids, saponins, glycerol, alcohols of 10–30 carbons in length, 6-(5-cholesten-3β-yloxy)-1-thio-β-D-galactopyranoside, digalactosyldiglyceride, 6-(5-cholesten-3β-yloxy)hexyl-6-amino-6-deoxy-1-thio-β-D-galactopyranoside, 6-(5-cholesten-3β-yloxy)hexyl-6-amino-6-deoxyl-1-thio-α-D-mannopyranoside, 12-(((7'-diethylaminocoumarin-3-yl)carbonyl)methylamino)-octadecanoic acid, N-[12-(((7'-diethylaminocoumarin-3-yl)carbonyl)methyl-amino) octadecanoyl]-2-aminopalmitic acid, cholesteryl(4'-trimethyl-ammonio)butanoate, N-succinyldioleoylphosphatidylethanol-amine, 1,2-dioleoyl-sn-glycerol, palmitoylhomocysteine, cationic lipids, N-[1-(2,3-diolcoyloxy)propyl]-N,N,N-trimethylammoium chloride, 1,2-dioleoyloxy-3-(trimethylammonio)propane, 1,2-dioleoyl-3-(4'-trimethyl-ammonio)butanoyl-sn-glycerol, alkyl phosphonates, alkyl phosphinates, and alkyl phosphites.

11. A composition according to claim 10, wherein the phosphatidylcholine is selected from the group consisting of dioleoylphosphatidylcholine, dimyristoylphosphatidylcholine, dipentadecanoylphosphatidylcholine, dilauroylphosphatidylcholine, dipalmitoylphosphatidylcholine, and distearoylphosphatidylcholine; wherein the phosphatidylethanolamine is dioleoylphosphatidylethanolamine; wherein the sphingolipid is sphingomyelin; wherein the glycolipid is selected from the group consisting of ganglioside GM1 and ganglioside GM2; wherein in the lipids bearing polymers the polymer is selected from the group consisting of polyethyleneglycol, chitin, hyaluronic acid, and polyvinylpyrrolidone, and cationic polymers, wherein said cationic polymers are selected from the group consisting of polylysine and polyarginine; wherein the sterol aliphatic acid esters are selected from the group consisting of cholesterol sulfate, cholesterol butyrate, cholesterol isobutyrate, cholesterol palmitate, cholesterol stearate, lanosterol acetate, ergosterol palmitate, and phytosterol n-butyrate; wherein the sterol esters of sugar acids are selected from the group consisting of cholesterol glucuronide, lanosterol glucuronide, 7-dehydrocholesterol glucuronide, ergosterol glucuronide, cholesterol gluconate, lanosterol gluconate, and ergosterol gluconate; wherein the esters of sugar acids and the esters of sugar alcohols are selected from the group consisting of lauryl glucuronide, stearoyl glucuronide, myristoyl glucuronide, lauryl gluconate, myristoyl gluconate, and stearoyl gluconate; wherein the esters of sugars and the esters of aliphatic acids are selected from the group consisting of sucrose laurate, fructose laurate, sucrose palmitate, sucrose stearate, glucuronic acid, gluconic acid, accharic acid, and polyuronic acid; wherein the saponins are selected from the group consisting of sarsasapogenin, smilagenin, hederagenin, oleanolic acid, and digitoxigenin; wherein the glycerol esters are selected from the group consisting of glycerol tripalmitate, glycerol distearate, glycerol tristearate, glycerol dimyristate, and glycerol trimyristate; wherein the alcohols of 10–30 carbon length are selected from the group consisting of n-decyl alcohol, lauryl alcohol, myristyl alcohol, cetyl alcohol, and n-octadecyl alcohol.

12. A composition according to claim 1 wherein the microsphere is prepared from at least one biocompatible polymer selected from the group consisting of polysaccharides, semisynthetic polymers and synthetic polymers.

13. A composition according to claim 12 wherein the polysaccharide is selected from the group consisting of arabinans, fructans, fucans, galactans, galacturonans, glucans, mannans, xylans, levan, fucoidan, carrageenan, galatocarolose, pectic acid, pectin, amylose, pullulan, glycogen, amylopectin, cellulose, dextran, pustulan, chitin, agarose, keratan, chondroitan, dermatan, hyaluronic acid, alginic acid, xanthan gum, starch, natural homopolymers and heteropolymers containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid.

14. A composition according to claim 12 wherein the semisynthetic polymer is selected from the group consisting of carboxymethylcellulose, hydroxymethylcellulose, hydroxypropylmethylcellulose, methylcellulose, and methoxycellulose.

15. A composition according to claim 12 wherein the synthetic polymer is selected from the group consisting of polyethylenes, polypropylenes, polyurethanes, polyamides, polystyrene, polylactic acids, fluorinated hydrocarbons, fluorinated carbons, and polymethylmethacrylate.

16. A composition according to claim 15 wherein the polyethylene is selected from the group consisting of polyethylene glycol, polyoxyethylene and polyethylene terephthlate; wherein the polypropylene is polypropylene glycol; wherein the polyurethane is selected from the group consisting of polyvinyl alcohol, polyvinylchloride and polyvinylpyrrolidone; wherein the polyamide is nylon; and wherein the fluorinated carbon is polytetrafluoroethylene.

17. A composition according to claim 1 additionally further comprising compounds selected from the group consisting of ingestible oils, viscosity modifiers, emulsifying and/or solubilizing agents, suspending and/or viscosity-increasing agents, synthetic suspending agents, and tonicity-raising agents.

18. A composition according to claim 17 wherein the ingestible oils are selected from the group consisting of peanut oil, canola oil, olive oil, safflower oil, and corn oil; wherein compounds for the mixed micelle systems are selected from lauryltrimethylammonium bromide, cetyltrimethylammonium bromide, myristyltrimethylammonium bromide, alkyldimethylbenzylammonium chloride (alkyl= $C_{12},C_{14},C_{16}$,), benzyldimethyldodecylammonium bromide/chloride, benzyldimethyl hexadecylammonium bromide/chloride, benzyl-dimethyltetradecylammonium bromide/chloride, cetyldimethylethylammonium bromide/chloride, and cetylpyridinium bromide/chloride; wherein the viscosity modifiers are selected from the group consisting of carbohydrates, polyethers having a molecular weight in the range of between 400 and 100,000, di- and trihydroxy alkanes and their polymers having a molecular weight in the range of between 200 and 50,000; wherein the emulsifying and/or solubilizing agents are selected from the group consisting of acacia, cholesterol, diethanolamine, glyceryl monostearate, lanolin alcohols, lecithin, mono- and di-glycerides, mono-ethanolamine, oleic acid, oleyl alcohol, poloxamer, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax; wherein the suspending and/or viscosity-increasing agents are selected from the group consisting of acacia, agar, alginic acid, aluminum monostearate, bentonite, purified bentonite, magma bentonite, carbomer 934P, carboxymethylcellulose calcium, carboxymethylcellulose sodium 12, carboxymethylcellulose sodium, carrageenan, microcrystalline cellulose, dextran, gelatin, guar gum, veegum, hydroxyethyl cellulose, hydroxypropyl cellulose, hydroxypropyl methylcellulose, magnesium-aluminum-silicate, methylcellulose, pectin, polyethylene oxide, polyvinyl alcohol, povidone, propylene glycol alginate, silicon dioxide, silicon dioxide, colloidal, zinc oxide, sodium alginate tragacanth, xanthan gum, α-d-gluconolactone, glycerol and mannitol; wherein the synthetic suspending agents are selected from the group consisting of polyethyleneglycol, polyvinylpyrrolidone, polyvinylalcohol, polypropylene glycol, and polysorbate; and wherein the tonicity-raising agents are selected from the group consisting of sorbitol, propyleneglycol and glycerol.

19. A composition according to claim 1 wherein the microsphere is prepared from a composition comprising dipalmitoylphosphatidylcholine, glycerol and propylene glycol.

20. A composition according to claim 1 wherein the microsphere is prepared from a composition comprising dipalmitoylphosphatidylethanolamine and phosphatidic acid in an amount of from 0.5 to 30 mole percent.

21. A composition according to claim 1 wherein the microsphere is prepared from a composition comprising dipalmitoylphosphatidylcholine and distearoylphosphatidyl-choline in an amount of from 70 to 100 mole percent.

22. A composition according to claim 1 wherein the microsphere is prepared from a composition comprising: (I) a neutral lipid, (ii) a negatively charged lipid, and (iii) a lipid bearing a hydrophilic polymer; wherein the amount of said negatively charged lipid is greater than 1 mole percent of total lipid present, and the amount of lipid bearing a hydrophilic polymer is greater than 1 mole percent of total lipid present.

23. A composition according to claim 22 wherein the negatively charged lipid is phosphatidic acid; wherein the polymer in the lipid bearing a hydrophilic polymer has a weight average molecular weight of from about 400 to about 100,000 and is covalently bound to said lipid.

24. A composition according to claim 23 wherein said hydrophilic polymer of said lipid bearing hydrophilic polymer is selected from the group consisting of polyethyleneglycol, polypropyleneglycol, polyvinylalcohol, and polyvinyl-pyrrolidone and copolymers thereof, and wherein said lipid of said lipid bearing a hydrophilic polymer is selected from the group consisting of dipalmitoylphosphatidylethanolamine, and distearoylphosphatidylethanolamine.

25. A composition according to claim 24 wherein the microsphere is prepared from about 77.5 mole percent dipalmitoylphophatidylcholine, about 12.5 mole percent of dipalmitoylphosphatidic acid, and about 10 mole percent of dipalmitoylphosphatidylethanolamnine-polyethyleneglycol 5000.

26. A composition according to claim 24 wherein the microsphere comprises about 82 mole percent dipalmitoylphophatidylcholine, about 10 mole percent of dipalmitoylphosphatidic acid, and about 8 mole percent of dipalmitoylphosphatidylethanolamine-polyethyleneglycol 5000.

27. A composition according to claim 1 wherein the gas is selected from the group consisting of hexafluoro acetone, isopropyl acetylene, allene, tetrafluoro-allene, boron trifluoride, isobutane, 1,2-butadiene, 2,3-butadiene, 1,3-butadiene, 1,2,3-trichloro-2-fluoro-1,3-butadiene, 2-methyl-1,3-butadiene, hexafluoro-1,3-butadiene, butadiyne, 1-fluorobutane, 2-methyl-butane, decafluorobutane, 1-butene, 2-butene, 2-methyl-1-butene, 3-methyl-1-butene, perfluoro-1-butene, perfluoro-2-butene, 4-phenyl-3-butene-2-one, 2-methyl-1-butene-3-yne, butyl nitrate, 1-butyne, 2-butyne, 2-chloro-1,1,1,4,4,4-hexafluoro-butyne, 3-methyl-1-butyne, perfluoro-2-butyne, 2-bromo-butyraldehyde, carbonyl sulfide, crotononitrile, cyclobutane, methyl-cyclobutane, octafluoro-cyclobutane, perfluoro-cyclobutene, 3-chlorocyclopentene, octafluorocyclopentene, cyclopropane, 1,2-dimethyl-cyclopropane, 1,1-dimethylcyclopropane, 1,2-dimethyl-cyclopropane, ethylcyclopropane, methylcyclopropane, diacetylene, 3-ethyl-3-methyl diaziridine, 1,1,1-trifluorodiazoethane, dimethyl amine, hexafluorodimethylamine, dimethylethylamine, bis-(dimethylphosphine)amine, perfluorohexane, 2,3-dimethyl-2-norbornane, perfluorodimethylamine, dimethyloxonium chloride, 1,3-dioxolane-2-one, 4-methyl-1,1,1,2-tetrafluoroethane, 1,1,1-trifluoroethane, 1,1,2,2-tetrafluoroethane, 1,1,2-trichloro-1,2,2-trifluoroethane, 1,1-dichloroethane, 1,1-dichloro-1,2,2,2-tetrafluoroethane, 1,2-difluoroethane, 1-chloro-1,1,2,2,2-pentafluoroethane, 2-chloro-1,1-difluoroethane, 1,1-dichloro-2-fluoroethane, 1-chloro-1,1,2,2-tetrafluoroethane, 2-chloro-1,1-difluoroethane, chloroethane, chloropentafluoroethane, dichlorotrifluoroethane, fluoroethane, hexafluoroethane, nitropentafluoroethane, nitrosopentafluoroethane, perfluoroethylamine, ethyl vinyl ether, 1,1-dichloroethane, 1,1-dichloro-1,2-difluoroethane, 1,2-difluoroethane, methane, trifluoromethanesulfonylchloride, trifluoromethanesulfonylfluoride, bromodifluoronitrosomethane, bromofluoromethane, bromochlorofluoromethane, bromotrifluoromethane, chlorodifluoronitromethane, chlorodinitromethane, chlorofluoromethane, chlorotrifluoromethane, chlorodifluoromethane, dibromodifluoromethane, dichlorodifluoromethane, dichlorofluoromethane, difluoromethane, difluoroiodomethane, disilanomethane, fluoromethane, iodomethane, iodotrifluoromethane, nitrotrifluoromethane, nitrosotrifluoromethane, tetrafluoromethane, trichlorofluoromethane, trifluoromethane, 2-methylbutane, methyl ether, methyl isopropyl ether, methyllactate, methylnitrite, methylsulfide, methyl vinyl ether, neopentane, nitrous oxide, 1,2,3-nonadecane-tricarboxylic acid-2-hydroxytrimethylester, 1-nonene-3-yne, 1,4-pentadiene, n-pentane, perfluoropentane, 4-amino-4-methylpentan-2-one, 1-pentene, 2-pentene(cis), 2-pentene(trans), 3-bromopent-1-ene, perfluoropent-1-ene, tetrachlorophthalic acid, 2,3,6-trimethylpiperidine, propane, 1,1,1,2,2,3-hexafluoropropane, 1,2-epoxypropane, 2,2-difluoropropane, 2-aminopropane, 2-chloropropane, heptafluoro-1-nitropropane, heptafluoro-1-nitrosopropane, perfluoropropane, propene, hexafluoropropane, 1,1,1,2,3,3-hexafluoro-2,3 dichloropropane, 1-chloropropane, chloropropane-(trans), 2-chloropropane, 3-fluoropropane, propyne, 3,3,3-trifluoropropyne, 3-fluorostyrene, sulfur hexafluoride, sulfur (di)-decafluoride($S_2F_{10}$), 2,4-diaminotoluene, trifluoroacetonitrile, trifluoromethyl peroxide, trifluoromethyl sulfide, tungsten hexafluoride, vinyl acetylene, vinyl ether, tetrafluoromethane, hexafluoroethane, octafluoropropane, decafluorobutane, dodecafluoropentane, perfluorohexane, perfluoroheptane, hexafluorocyclopropane, octafluorocyclobutane, air, nitrogen, carbon dioxide, oxygen, argon, fluorine, xenon, neon, helium.

28. A composition according to claim 1 wherein the gas is selected from the group consisting of perfluorocarbon gases, fluorohydrocarbon gases, and sulfur hexafluoride.

29. A composition according to claim 1 wherein the gas is selected from the group consisting of sulfur hexafluoride, unsaturated perfluorocarbons, saturated perfluorocarbons of the formula $C_nF_{2n+2}$, where n is from 1 to 12, and cyclic perfluorocarbons of the formula $C_nF_{2n}$, where n is from 3 to 8.

30. A composition according to claim 1 wherein the gas is derived from a gaseous precursor.

31. A composition according to claim 1 wherein the gas filled microsphere is stabilized.

32. A composition according to claim 1 wherein the gas filled microsphere is in the form of a foam.

33. A composition according to claim 32 wherein the foam is stabilized.

34. A composition of claim 1 wherein said microsphere comprises a monolayer.

35. A composition of claim 34 wherein said monolayer comprises a phospholipid.

36. A composition of claim 35 wherein said gas is selected from the group consisting of perfluoropropane, perfluorobutane, perfluoropentane, perfluorohexane, and sulfur hexafluoride.

37. A composition of claim 34 wherein said monolayer comprises a phospholipid and said gas is perfluoropentane.

38. A composition of claim 34 wherein said monolayer comprises a phospholipid and said gas is sulfur hexafluoride.

39. A composition of claim 34 wherein said monolayer comprises a phospholipid and said gas is perfluoropropane.

40. A method of claim 1 wherein said microsphere comprises a polymer.

41. A method of claim 40 wherein said polymer comprises an acrylate.

42. A method of claim 41 wherein said gas is air.

43. A composition of claim 1 wherein said microsphere comprises a polysaccharide.

44. A composition of claim 43 wherein said polysaccharide comprises galactose.

45. A composition of claim 44 wherein said gas is nitrogen.

46. A composition of claim 10 wherein said biocompatible lipid is a polymerized lipid.

47. A composition of claim 10 wherein said microsphere further comprises polyethylene glycol.

48. A composition of claim 10 wherein said fatty acids are selected from the group consisting of phosphatidic acid, palmitic acid, stearic acid, arachidonic acid, and oleic acid.

49. A composition of claim 1 wherein said compounds form a mixed micelle system.

50. A composition of claim 1 wherein said microsphere comprises a surfactant.

51. A composition of claim 50 wherein said gas is a perfluorocarbon.

52. A composition of claim 50 wherein said gas is selected from the group consisting of nitrogen, perfluoromethane, perfluoroethane, perfluoropropane, perfluorobutane, perfluoropentane, perfluorohexane, perfluoroheptane, hexafluorocyclopropane, octafluorocyclobutane, decafluorocyclopentane and sulfur hexafluoride.

53. A composition of claim 52 wherein said gas is perfluorohexane.

54. A composition of claim 52 wherein said gas is perfluoropentane.

55. A composition of claim 52 wherein said gas is perfluorobutane.

56. A composition of claim 52 wherein said gas is perfluoropropane.

57. A composition of claim 52 wherein said gas is a combination of nitrogen and perfluorohexane.

58. A composition of claim 52 wherein said gas is a combination of nitrogen and perfluoropropane.

59. A composition of claim 50 wherein said microsphere is lyophilized.

60. A composition of claim 1 wherein said therapeutic agent is selected from the group consisting of anti-fungal agents, hormones, vitamins, peptides, enzymes, anti-allergic agents, anti-coagulation agents, antituberculars, antivirals, antibiotics, anti-inflammatory agents, antiprotozoans, local anesthetics, growth factors, cardiovascular agents, diuretics, and radioactive compounds.

* * * * *

UNITED STATES PATENT AND TRADEMARK OFFICE
CERTIFICATE OF CORRECTION

PATENT NO. : 5,733,572
DATED : Mar. 31, 1998
INVENTOR(S) : Unger et al.

It is certified that error appears in the above-identified patent and that said Letters Patent is hereby corrected as shown below:

Title page, item [73] under "OTHER PUBLICATIONS", at Miller, third line thereof, please delete "2274." and insert --224.--.

On page 2, first column, under "U.S. PATENT DOCUMENTS", at "4,569,836", following "Gordon", please insert -- . . . . . . . . . . . . . . . . . . . . . . 424/1.1--.

On page 3, second column, under "OTHER PUBLICATIONS", please delete "Ter-Pogossia *Tomography*, Kee, et al., n. "Physical Principles and Instrumentation", *Computed Body* eds., Raven Press, New York, Chapter 1, pp. 1-7 (1988)."

On page 3, second column, under "OTHER PUBLICATIONS", at "Aronberg," second line thereof, please delete "Kee" and insert --Lee--.

On page 4, second column, under "OTHER PUBLICATIONS", at "Shiina", please delete " 'Hyperthermiaby" and insert --"Hyperthermia by--.

On page 5, first column, under "OTHER PUBLICATIONS", at "Poznansky", please delete " 'Biologica" and insert --"Biological--.

On page 5, second column, under "OTHER PUBLICATIONS", at "Ter-Pogossian", following "Tomography", please insert --Lee, et al., eds., Raven Press, New York,--.

On page 5, second column, under "OTHER PUBLICATIONS", at "Ter-Pogossian", following "1-7", please insert --(1988)--.

UNITED STATES PATENT AND TRADEMARK OFFICE
CERTIFICATE OF CORRECTION

PATENT NO. : 5,733,572
DATED : Mar. 31, 1998
INVENTOR(S) : Unger et al.

It is certified that error appears in the above-identified patent and that said Letters Patent is hereby corrected as shown below:

In column 6, line 51, please delete "biocompatable" and insert --biocompatible--.

In column 6, line 64, please delete "conglomoration)" and insert --conglomeration)--.

In column 8, line 31, please delete "gasesous" and insert --gaseous--.

In column 8, lines 50-51, please delete "diffusability" and insert --diffusibility--.

In column 22, line 7, please delete "abovementioned" and insert --above-mentioned--.

In column 28, line 18, please delete "N-cocalyklpyrrolidone" and insert --N-coalkylpyrrolidone--.

In column 28, line 39, please delete "yang ylang" and insert --ylang ylang--.

In column 28, line 58, please delete "particularily" and insert --particularly--.

In column 29, line 26, please delete "Similarily," and insert --Similarly--.

In column 38, line 66, please delete "particularily" and insert --particularly--.

In column 39, line 29, please delete "recipreciprocations," and insert --reciprocations--.

UNITED STATES PATENT AND TRADEMARK OFFICE
CERTIFICATE OF CORRECTION

PATENT NO. : 5,733,572
DATED : Mar. 31, 1998
INVENTOR(S) : Unger et al.

It is certified that error appears in the above-identified patent and that said Letters Patent is hereby corrected as shown below:

In column 40, line 5, please delete "installation" and insert --instillation--.

In column 41, line 59, please delete "1,2-dipalimitoyl-phosphatidylcholine" and insert --1,2-dipalmitoyl-phosphatidylcholine--.

In column 44, line 5, please delete "temperturs" and insert --temperature--.

In column 48, line 21, please delete "with. the" and insert --with the--.

In column 48, line 23, please delete "1,2-dipalimitoylphosphatidylcholine" and insert --1,2-dipalmitoylphosphatidylcholine--.

In column 54, line 8, please delete "dipamitoyl-sn-" and insert -- dipalmitoyl-sn- --.

In column 54, line 27, please delete "Dipamitoyl-sn-Glycero-3-" and insert -- Dipalmitoyl-sn-Glycero-3- --.

In column 54, line 30, please delete "dipamitoyl-sn-" and insert -- dipalmitoyl-sn- --.

In column 54, line 39, please delete "Dipamitoyl-sn-Glycero-3-" and insert -- Dipalmitoyl-sn-Glycero-3- --.

In column 54, line 42, please delete "dipamitoyl-sn-" and insert -- dipalmitoyl-sn- --.

UNITED STATES PATENT AND TRADEMARK OFFICE
CERTIFICATE OF CORRECTION

PATENT NO. : 5,733,572
DATED : March 31, 1998
INVENTOR(S) : Unger et al.

It is certified that error appears in the above-identified patent and that said Letters Patent is hereby corrected as shown below:

In column 55, line 37, please delete "Nucleopore" and insert --Nuclepore--.

In column 58, claim 3, line 49, please delete "bcclomethasone" and insert --beclomethasone--.

In column 59, claim 3, line 6, please delete "ethionamnide," and insert --ethionamide--.

In column 59, claim 4, line 56, please delete "mad" and insert --and--.

In column 61, claim 10, line 46, please delete "(2,3-diolcoyloxy)" and insert --(2,3-dioleoyloxy)--.

UNITED STATES PATENT AND TRADEMARK OFFICE
CERTIFICATE OF CORRECTION

PATENT NO. : 5,733,572
DATED : Mar. 31, 1998
INVENTOR(S) : Unger et al.

It is certified that error appears in the above-identified patent and that said Letters Patent is hereby corrected as shown below:

In column 61, claim 10, line 47, please delete "trimethylammoium" and insert --trimethylammonium--.

In column 61, claim 11, line 62, following "polymers", please insert a comma -- , --.

In column 63, claim 22, line 67, please delete "(I)" and insert --(i)--.

Signed and Sealed this

Thirteenth Day of July, 1999

Attest:

Q. TODD DICKINSON

Attesting Officer

Acting Commissioner of Patents and Trademarks